United States Patent [19]
Gonzalez et al.

[11] Patent Number: 5,891,633
[45] Date of Patent: Apr. 6, 1999

[54] DEFECTS IN DRUG METABOLISM

[75] Inventors: Frank J. Gonzalez, Bethesda, Md.; Jeffrey R. Idle, Troodheim, Norway

[73] Assignee: The United States of America as represented by the Department of Health and Human Services, Washington, D.C.

[21] Appl. No.: 750,703

[22] PCT Filed: Jun. 16, 1995

[86] PCT No.: PCT/US95/07605

§ 371 Date: Apr. 7, 1997

§ 102(e) Date: Apr. 7, 1997

[87] PCT Pub. No.: WO95/34679

PCT Pub. Date: Dec. 21, 1995

[30] Foreign Application Priority Data

Jun. 16, 1994 [GB] United Kingdom ........... 9412054
Feb. 13, 1995 [GB] United Kingdom ........... 9502728
Apr. 12, 1995 [GB] United Kingdom ........... 9507640

[51] Int. Cl.$^6$ ................. C12Q 1/68; C07H 21/02
[52] U.S. Cl. ........................ 435/6; 536/22.1
[58] Field of Search ............... 435/6, 91.2; 536/22.1, 536/23.1

[56] References Cited

U.S. PATENT DOCUMENTS 5,399,346  3/1995  Anderson et al. ........... 424/93.21

FOREIGN PATENT DOCUMENTS

WO 91/01990  2/1991  WIPO.
WO 94/01548  1/1994  WIPO.

OTHER PUBLICATIONS

Fernandez–Salguero, P. et al., "A Genetic Polymorphism in Coumarin 7–Hydroxylation Sequence of the Human CYP2A Genes and Identification of Variant CYP2A6 Alleles", *American Journal of Human Genetics*, vol. 57, Sep. 1995, pp. 651–660.

Tiano, H. et al., Retroviral mediated expression of human cytochrome P450 2A6 in CH3/10T1/2 cell confers transformability by 4–(methylnitrosamino)–1–(3–pyridyl)–1–butanone (NNK), *Carcinogenesis*, vol. 14, No. 7, Jul. 1993, pp. 1421–1427.

Yamano, S. et al., "The CYPA3 Gene Product Catalyses Coumarin Hydroxylation in Human Liver Microsomes", *Biochemistry*, vol. 29, 1990, pp. 1322–1329.

*Primary Examiner*—Eggerton A. Campbell
*Attorney, Agent, or Firm*—Morgan & Finnegan, L.L.P.

[57] ABSTRACT

The invention relates to genetic material, and specifically portions of DNA, for identifying the presence or absence of a mutation in the drug metabolism gene CYP2C9 and CYP2A6. Further, the invention comprises a method for determining such mutations and a kit incorporating the genetic material of the invention for performing the said methods so as to determine the presence or absence of mutations in the drug metabolizing gene CYP2C9 and CYP2A6.

25 Claims, 32 Drawing Sheets

FIG. 1A

```
                  ......exon 2......
IIC1 (C9)          GATCTTGGAGAGGAGTTTTCTGGAAGAGGCATTTTCCCACTGGCT
                   Asp Leu Gly Glu Glu Phe Ser Gly Arg Gly Ile Phe Pro Leu Ala
IIC2 (C8)          GATAATGGAGAGGAGTTTTCTGGAAGAGGCAATTCCCCAATATCT
                   Asp Asn Gly Glu Glu Phe Ser Gly Arg Gly Asn Ser Pro Ile Ser
DIIC2

Clone 4 (hIIc1-4)  GATCTTGGAGAGGAGTTTTCTGGAAGAGGCCATTTCCCACTGGCTG

Clone 18 (hIIc1-18) GATCATGGAGAGGAGTTTTCTGGAAGAGGAAGTTTTCCAGTGGCTG

Clone 3

Clone 16           GATCATGGAGAGGAGTTTTCTGGAAAAGGTATTTTCCCAGTATCCA

Clone 21 (hIIc1-21) GATCTTGGAGAGGAGTTTTCTGGAAGAGGCCATTCCCACTGGCTG

Clone 26 (hIIc1-26) GATCATGGAGAGGAGTTTTCTGGAAGAGGAAGTTTTCCAGTGGCTG
Clone 33
```

FIG. 1B

```
         ........exon 2.................][Start of intron 2........
IIC1     GAAAGAGCTAACAGAGGATTTG
         Glu Arg Ala Asn Arg Gly Phe G
IIC2     CAAAGAATTACTAAAGGACTTG
         Gln Arg Ile Thr Lys Gly Leu G DIIC2                                    CTTGGTAGGTGCACATATTCTGTGTCAGCTTTGGTAAC
Clone 4  AAAGAGCTAACAGAGGATTTGGTAGGTGTGCAAGTGCCTGTTTCAGCATCTGTCTTGG
                                                           Primer HF-18
Clone 18 AAAAAGTTAACAAAGGACTTGGTAAATGTGCATGTATCGTGTGTATGTGTACATGT Clone 16 AAAAAGCTA GTAAGGAGTTGGTACATGTGTGTCAGTGTGTGTGCCTTTGTCTG
Clone 21 AAAGAGCTAACAGAGGATTTGGTAGGTGTGCAAGTGCCTGTTTCAGCATCTGTCTTGG
Clone 26 AAAAAGTTAACAAAGGACTTGGTAAATGTGCATGTATCGTGTATGTGTACATGT
```

FIG. 1C

```
DIIC2     ........intron 2........
          TGGGGTGAGGGGGATGGAAAAACAGAGCCCTAAAAAGCTTCTCAGCAGAGCTTAGC
Clone 4   GGATGGGGAGGATGGAAAAACAGAGACTTACAGAGCTCCTCGGCAGAGCTTGGCCCA
Clone 18  GTATGTACTGGGCAGTGGCTATAGGGATGGGGAGGATGGAAAACAGGCTTGAAAA
Clone 3                        CAGAAGGTGAAT(G)GAAACAACAC(T)TGAA
Clone 16  TATTAGTAATGAGGCAGAAGTGAATGGAAAACAAACACTTGAAGAGCTCCTAAA
Clone 21  GGATGGGGAGGATGGAAAACAGA[       CTA    GCAGAGCT(T)]CTCGGG
Clone 26  GTATGTACTGGGCAGTGGCTATAGAGGGATGGGGAGGATGGAAAACAGGUTTGAAGA
```

FIG. 1D

```
DIIC2    ......intron 2......
         CTATCTGCATGGCTGCCAAGTGTTGCAGCACTTTCTTCCTTGGCTGTGAATTCTC Clone 4  TCCACATGGCTGCCCAGTGTCAGCTTCCCTCTTTCTTGCCTGGGATCTCCCTCCTA Clone 18 GCTCCTGGGACAGAACTTGACCTGTCCACGTGGCTGCCGAGTGTCAGCTCTCTTG Clone 3  GAGCTCCTAAAC(T)TAGC(T)TAGCTTGGCCATTGGGTGGCTGTTGAAAATCAGCTTC Clone 16 ACTTAGCTTGGCC(C)ATTTGGTGGCTGTGTTGAAATCAGCTTCCTCTTTCNNNC(C)TGG Clone 21 CAGAGCTTGGCCCATCCACATGGCTGCCCAGTGTCAGCTTCCTCTTTCTTGCCTG ]Clone 26 GCTCCTGGGACAGAACTTGACCTGTCCACGTGGCTGCCGAGTGTCAGCTCTCTTG
```

FIG. 1E

```
                ....end of intron 2]
DIIC2     CCAGTTCTGCCCCTTTTTTATTAG
Clone 4   GTTTCGTTTCTCTTCCTGTTAG
Clone 18  TCCTTGTTTGGATTCTCCCTCGTAGCTTCGTGTTTCTGTTTCTGCTAG
Clone 3   CTCTTTCTTGCCTGGGATCTCCCTCGTTTCTGTTTCCCTTCCTTTCA
Clone 16  ATCTCCCTCCTCGTTTCTGTTCCTCCTTC                    A
Clone 21  GGATCTCCCTCCTAGTTTCGTTTCTCTTCCTGTT               AG
Clone 26  TCCTTGTTTGGATTCTCCCCTCGTAGCTTCGTGTTTTCTGTTCTGCTAG
```

FIG. 1F

[Start of exon 3 ─────

| | |
|---|---|
| IIC1 | GAATTGTTTTCAGCAATGGAAAGAGAAATGGAAGGAGAGATCCGGCGTTTCTCCCTCATGACG |
| | ly Ile Val Phe Ser Asn Gly Lys Lys Trp Lys Glu Ile Arg Arg Phe Ser Leu Met Thr |
| IIC2 | GAATCATTTCCAGCAATGGAAAGAGATGGAAGGAGAGATCCGGCGTTTCTCCCTCACAACC |
| | ly Ile Ile Ser Ser Asn Gly Lys Arg Trp Lys Glu Ile Arg Arg Phe Ser Leu Thr Thr |
| DIIC2 | GAATCATTTCCAGCAATGGAAAGAGATGGAAGGAGAGATCCGGGCGTTTCTCCCTCACAACC |
| Clone 4 | GAATTGTTTTCAGCAATGGAAAGAAATGGAAGGAGATCAGGCCGTTTCTCCCTCATGACG |
| Clone 18 | GAATCCTTTTCAGCAATGGAAAGAGATGGAAGGAGAGATCCGGCGTTTCTGCCTCATGACT |
| Clone 3 | GGATCATTTTTAGCAATGGAAAGAGATGTAAGGATGTCTGGCTCTCTTGCTCATGACG |
| Clone 16 | GGATCATTT |
| Clone 21 | GAATCGTTTTCAGCAATGGAAAGAGATGGAAGGAGAGATCCGGCGTTTCTCCCTCATGACG |
| Clone 26 | GAATCCTTTTCAGCAATGGAAAGAGATGGAAGGAGAGATCCGGGCGTTTCTCCCCATGACG |
| Clone 33 |                                               G      T      T |

FIG. 1G

```
.......exon 3.......

IIC1   CTGCGGGAATTTTGGGATGGGGAAGAGGAGCATTGAGGACTGTGTTCAAGAGGAAGCCCG
       Leu Arg Asn Phe Gly Met Gly Lys Arg Ser Ile Glu Asp Cys Val Gln Glu Glu Ala Ar

IIC2   TTGCGGGAATTTTGGGATGGGGAAGAGGAGCATTGAGGACCGTGTTCAAGAGGAAGCTCA
       Leu Arg Asn Phe Gly Met Gly Lys Arg Ser Ile Glu Asp Arg Val Gln Glu Glu Ala Hi

↑
                            Site of A₁₄₄C polymorphism

DIIC2  TTGC

Clone 4    CTGCGGGAATTTTGGGATGGGGAAGAGGAGCATTGAGGACCGTGTTCAAGAGGAAGCCCG

Clone 18   CTGCGGGAATTTTGGGATGGGGAAGAGGAGCATTCGAGGACCGTGTTCAAGAGGAAGCCCG

Clone 3    CTCTGGAATTGTAGGATGGTGAAGAGGAGCAATGGAGA    TGTTCAAGGTGAAGCCCA
                                                AGCA Clone 21   CTGCGGGAATTTTGGGATGGGGAAGAGGAGCATTGAGGACCGTGTTCAAGAGGAAGCCCG Clone 26   CTGCGGGAATTTTGGGATGGGGAAGAGGAGCATTGAGGACCGTGTTCAAGAGGAAGCCCG
Clone 33                                                              C
```

FIG. 2A

```
                                                                                                            42
2A6 intron 2   -------GT GCCCAAGAGAG GGGAAGGTGG GCAGGTGGAC ACGAAGGTCT          49
2A8 intron 2   GTGAGGGGGT G-CCAAGAGG GGGAAGGTGG TCAGGTGGAT GCAATGGTCT          41
2A7 intron 2   -------GT G-CCAAGATG GGGAAGGTGG GCAGGCGGAC ACGATGGTCT          50
Consensus      GTGAGGGGGT GCCCAAGAKG GGGAAGGTGG ECAGGYGGAY RCRAWGGTCT 92
2A6 intron 2   CAGTGTTCCC AGCCTTCTCC CTGACTCTCC TGACAACTGG AGGATAAGGG          99
2A8 intron 2   CCGTGTCCCC AGCCTTCTCC CTGACTCTCC TGCCCACTGG AGGATATGGG          91
2A7 intron 2   CAGTGTTGCC AGCCTTCTCC CTGACTCTCC TGACCACTGG AGGCTATGGA         100
Consensus      CMGTGTYSCC AGCCTTCTCC CTGACTCTCC TGMCMACTGG AGGMTAWGGR 142
2A6 intron 2   AGAGTCCCCA GTCTGGTCTT CCCTCACCTG CTCCCTACAT TGGGGCCTCT         149
2A8 intron 2   AGAGCCCCCC GTCTGGTCTT CCACACCTG  CTCCCTACAC CGGGGACTCT         141
2A7 intron 2   AGAACCCCCG GCTGGTCTT  CCCCCACCTG CTCCCCTTCAC TGTGGCCTCT        150
Consensus      AGARYCCCCD GKCTGGTCTT MYCTCCCCAT CTCCCTWCAY YGKGGMCTCT 192
2A6 intron 2   CCATGTGTAT CCCTCACCTG TCTCCAGCGG CCCTGTCCTG ATTCCTCCCT         199
2A8 intron 2   CCCTGTGAGT CCCACCGTC  TCTCCAGCGC CCCTGGCGTG ATTCCTCCT          190
2A7 intron 2   CCATGTGTAT CCCCCACCTC TCTCCAGCGC CCCGGTCGTG ATTCCTCCC-         200
Consensus      CCMTGTGWRT CCCHCACCTG TCTCCAGCGS CCCKGKCSTG ATTCCTCCCT 242
2A6 intron 2   GCCTCTCTCT GCCCCAGCTC CTTATTCTCT CTCACTGGAG TCTCCTCTTT         249
2A8 intron 2   GCCTCTCTCT GCCCCGTCTC CTCCCTTCTC CTCACTGGAG TCTCCTCTTA         239
2A7 intron 2   GGCTCTCTCT GCCCCACCTC CAGATTCTCT CTCA-TGGAG TCTCCTCTTA         250
Consensus      GSCTCTCTCT GCCCCRYCTC CWBMTTCTCT CTCACTGGAG TCTCCTCTTW
```

```
                                                                                                        292
2A6 intron 2  CCCTCTCTC  TCCATCTCTA  AGGACATCCT  GGGTTTCTGT  TTACCAGCCC  299
2A8 intron 2  CCCCTCTCTC  TCCATCTCTG  AGGACATCCG  GGGTTTCTGT  TTACCAGCCC  267
2A7 intron 2  CTCCTCTCTC  TCCAACTCTG  AGGACATC--  ----------  ----------

Consensus     CYCCTCTCTC  TCCAWCTCTR  AGGACATCCK  GGGTTTCTGT  TTACCAGCCC  300

342
2A6 intron 2  TGGGTCTCTG  TCTACATGAG  TCTTTGAGGC  CCTCTTAGCT  TCTGGGCTTC  349
2A8 intron 2  TGGTCCTCTG  TCTTCATTTG  TCTTTTTGTC  GCTCTCGGCT  TCTGTGCTTC  271
2A7 intron 2  ----------  ---TTGG---  ----------  ----------  ----------

Consensus     TGGKYCTCTG  TCTWCATKWG  TCTTTKWGKC  SCTCTYRGCT  TCTGKGCTTC  350

392
2A6 intron 2  TCTGGGTTTC  TCATCTCTCC  GGATCCCTTT  CTCAATTCTT  CCTCTGTCTT  399
2A8 intron 2  TCCGTGTTTC  TCCTCTCTCT  GCTCCCCTCT  CCCACTTCTT  CCTCTGTCTT  271
2A7 intron 2  ----------  ----------  ----------  ----------  ----------

Consensus     TCYGKGTTTC  TCMTCTCTCY  GSWTCCCTYT  CYCAMTTCTT  CCTCTGTCTT  400

442
2A6 intron 2  AGGATGCCAG  GGTTATTCCT  ACTTCCACAT  CTTCAGGCTC  CATCTCCTGG  448
2A8 intron 2  AGGATTTCAG  GGT-ATTCCT  ACTTCCACAT  CTCCAGCTCC  CAACTCCTGG  271
2A7 intron 2  ----------  ----------  ----------  ----------  ----------

Consensus     AGGATKYCAG  GGTTATTCCT  ACTTCCACAT  CTYCAGSYYC  CAWCTCCTGG  450

492
2A6 intron 2  TAACAGTCTC  TCTTCCTTCC  AGACCCTCTC  TGTTTCTATC  TCAATATTAA  498
2A8 intron 2  TAATTGTCTG  TCCTCCTTCC  CGATCCCTCC  TGTTTCTGTC  TCCATATTTT  271
2A7 intron 2  ----------  ----------  ----------  ----------  ----------

Consensus     TAAYWGTCTS  TCYTCCTTCC  MGAYCCTCTC  TGTTTCTRTC  TCMATATTWW  500
```

FIG. 2C

```
2A6 intron 2   ACTCTCT--G CTCCAGCTCA GCTTAAGAAT CTCACACCAA GAGAGGATGT   540
2A8 intron 2   TCTCTCTCTT CTCCAGTTCA GATTAAGAAT CTTTCACCA- -TTTTATTT    546
2A7 intron 2   ---------- ---------- ---------- ---------- ----------   271

Consensus      WCTCTCTCTK CTCCAGYTCA GMTTAAGAAT CTYWCACCAA GWKWKKATKT   550

2A6 intron 2   CCTCCACCCA GATCTCCCCA TATCTCACTA CCCCACCCTC CATC---CTC   587
2A8 intron 2   CCTCCTCCCA GATCTCCCCA TATCTCACTT CCCCTCCCTC CATCTCTCTC   596
2A7 intron 2   ---------- ---------- ---------- ---------- ----------   271

Consensus      CCTCCWCCCA GATCTCCCCA TATCTCACTW CCCCWCCCTC CATCTCTCTC   600

2A6 intron 2   TGCCT----C CATCAC--TC TCTTTCTC-- ------TCC  CC--A-----   615
2A8 intron 2   TTTCTCTCCC CACTACCTTC CCTTCCTCCA TGGAGTATCC CCGTATCCCT   646
2A7 intron 2   ---------- ---------- ---------- ---------- ----------   271

Consensus      TKYCTCTCCC CAYYACCTTC YCTTYCTCCA TGGAGTATCC CCGTATCCCT   650

2A6 intron 2   CTGCCCCTGC GGACGCGATC CAATGG--AG TGTG------ ----GA---G   650
2A8 intron 2   CTGTTTCTCT GCATCTGTCT GTCTGGCCTT TCTGCTTCTC TTCTGATTCT   696
2A7 intron 2   ---------- ---------- ---------- ---------- ----------   271

Consensus      CTGYYYCTSY GSAYSYGWYY SWMTGGCCWK TSTGCTTCTC TTCTGATTCK   700

2A6 intron 2   CTAATGCCGT ------GAA GCTATGTGCA TCTCTCTGTC TGGCCGTACC   693
2A8 intron 2   CTTATTCTTT CTACCCGGAC TCTCTCTCTC TCTCTCTCTC TCTCTCTCTC   746
2A7 intron 2   ---------- ---------- ---------- ---------- ----------   271

Consensus      CTWATKCYKT CTACCCGGAM KCTMTSTSYM TCTCTCTSTC TSKCYSTMYC   750
```

FIG. 2D

```
2A6 intron 2    TGGGT---AA TAACCTGATC GACT------ ---------- ----------   714
2A8 intron 2    TCTCTCTCTC TCTCTCTCTC TCTCTCTCTC TCTCTCTCTA ----------   796
2A7 intron 2    ---------- ---------- ---------- ---------- TATATATATA   271

Consensus       TSKSTCTCWM TMWCYYKMTC KMYYTCTCTC TCTCTCTCTA TATATATATA   800

2A6 intron 2    ---------- ---------- ---------- ---------- ----------   714
2A8 intron 2    TATATATATA CACACACACA CACACACACA CACACACACA CACACACATA   846
2A7 intron 2    ---------- ---------- ---------- ---------- ----------   271

Consensus       TATATATATA CACACACACA CACACACACA CACACACACA CACACACATA   850

2A6 intron 2    ---------- ---------- ---------- ---------- ----------   714
2A8 intron 2    TATATTAGGG GGGGACTCCC CTCTGCTCC TTTCTGCTCC ACCCTTGGGG   896
2A7 intron 2    ---------- ---------- ---------- ---------- AGCCCCTTGG   271

Consensus       TATATTAGGG GGGGACTCCC CTCTGCTCC TTTCTGCTCC ACCCTTGGGG   900

2A6 intron 2    ---------- ---------- ---------- ---------- ----------   714
2A8 intron 2    AACTGGTCCG CTCTGCTACC ACCACCCCCT GACCTCTCTC CACCCCCGCG   946
2A7 intron 2    ---------- ---------- ---------- ---------- ----------   271

Consensus       AACTGGTCCG CTCTGCTACC ACCACCCCCT GACCTCTCTC CACCCCCGCG   950

2A6 intron 2    ---------- --                                             714
2A8 intron 2    TTCACCTCCC CA                                             958
2A7 intron 2    ---------- --                                             271

Consensus       TTCACCTCCC CA                                             962
```

FIG. 2E

|  |  |  |  |  |  |  |
|---|---|---|---|---|---|---|
| 2A8 exon 3 | GCGTGGCGTT | CAGCAACGTT | GAGCGGCGCCA | AGCAGCTCCG | GCGCTTCTCC | 50 |
| 2A6 exon 3 | GCGTGGTATT | CAGGAACGGG | GAGCGGCGCCA | AGCAGCTCCT | GCGCTTTGCC | 50 |
| 2A7 exon 3 | GCGTGGCGTT | CAGCAACGGG | GAGCGGCGCCA | AGCAGCTCCT | GCGCTTTGCC | 50 |
| Consensus  | GCGTGGYRTT | CAGSAACGGG | GAGCGGCGCCA | AGCAGCTCCK | GCGCTTYKCC | 50 |

|  |  |  |  |  |  |  |
|---|---|---|---|---|---|---|
| 2A8 exon 3 | ATCGCCACCC | TAAGGGGTTT | TGGCGTGGGC | AAGCGCGGCA | TCGAGGAACG | 100 |
| 2A6 exon 3 | ATCGCCACCC | TGAGGGACTT | CGGGGTGGGC | AAGCGGAGGCA | TCGAGGAGCG | 100 |
| 2A7 exon 3 | ATCGCCACCC | TGAGGGACTT | CGGGGTGGGC | AAGCGGAGGCA | TCGAGGAGCG | 100 |
| Consensus  | ATCGCCACCC | TFAGGGRYTT | YGGSGTGGGC | AAGCGMGGCA | TCGAGGAFCG | 100 |

|  |  |  |  |  |  |  |
|---|---|---|---|---|---|---|
| 2A8 exon 3 | CATCCAGGAG | GAGCCGGGCT | TCCTCATCGA | CGCCCTCCGG | GGCACGCACG | 150 |
| 2A6 exon 3 | CATCCAGGAG | GAGTCGGGCT | TCCTCATCGA | GGCCATCGG | AGCACGCACG | 150 |
| 2A7 exon 3 | CATCCAGGAG | GAGTCGGGCT | TCCTCATCGA | GGCCATCCGG | AGCACGCACG | 150 |
| Consensus  | CATCCAGGAG | GAGKCGGGCT | TCCTCATCGA | SGCCMTCCGG | FGCACGCACG | 150 |

Codon 160 ↑

← Primer J51/61 →

FIG. 2F

```
2A8 intron 3                                                           G TGAGTAGGGG ACCCCGAGTG    21
2A6 intron 3   GTGAGCAGGG ---------- GACCCCGAGT GCGGGGGCAG -GAGAAGGAA AACAC-----    44
2A7 intron 3   GTGAGTAAGG ---------- TTCCCCGAGT GCGGGGGCAG -GAGAAGGAA AACAC-----    44

Consensus      GTGAGYARGG KWCCCCGAGT GCGGGGGCAG TGAGWAGGRR AMCMCGAGTG              50

2A8 intron 3   CGAGGGCG-G GAACC--CGC GCTTTCTGCC TGGGGATGGG GACTAGGTGG               68
2A6 intron 3   CCAGGACGAG GAACCCGCGC GCGTTCTGCC TGGGGATGGG GACTAGGTGG               94
2A7 intron 3   CCAGGACGAG GAACCCGCGC GCGTTCTGCC TGGGGATGGG GACTAGGTGG               94

Consensus      CSAGGFCGAG GAACCCGCGC GCKTTCTGCC TGSGGATGGG GACTAGGTGG              100

2A8 intron 3   GGAAAGGGGC CCGCACTTCC AGCCCTGGAG GGAATTCTGA TCTGGCGCT- GGGATTCGGC         117
2A6 intron 3   GGAAAGGGGC CCGCACTTCC AGCCCTGGAG GGAATTCTGA TCTGGCGCTG GGAATTTGGC         144
2A7 intron 3   GGAAAGGGCG CCGCACTTCC AACCCTGGAA GGAATTCTGA TCTGGCGCTG GGGATTTGGC         144

Consensus      GGAAAGGSGC CCGCACTTCC AFCCCTGGAR GGAATTCTGA TCTGGCGCTG GGRATTYGGC         150

2A8 intron 3   TCAACAGGGC CCTGCCTCCT CTCTCCTCAG ACCTCTGAGT                              167
2A6 intron 3   TCAACAAGGC CCTGCCTCCT CTCTCCTCAG ACCTCTGAGT                              194
2A7 intron 3   TCAACAAGGC CCTGCCTCCT CTCTCCTCAG ACCTCTGAGT                              194

Consensus      TCAACAFGGC CCTGCCTCCT CTCTCCTCAG ACCTCTGAGT                              200
                        ← Primer B →

2A8 intron 3   TGACTCTCTC CCCAACCCCC CTTCTCCCGC CACACCTTGTA -                           207
2A6 intron 3   TGACTCTCTC CCCAACCCCC T-TCTCCCGA CATACCGGA  -                           233
2A7 intron 3   TGACTCTCTC CCCAACCCCC TCCCTCCCTC CACACCTGCA G                           235

Consensus      TGACTCTCTC CCCAACCCCC YYYCTCCCKM CAYACCYGFA G                           241
```

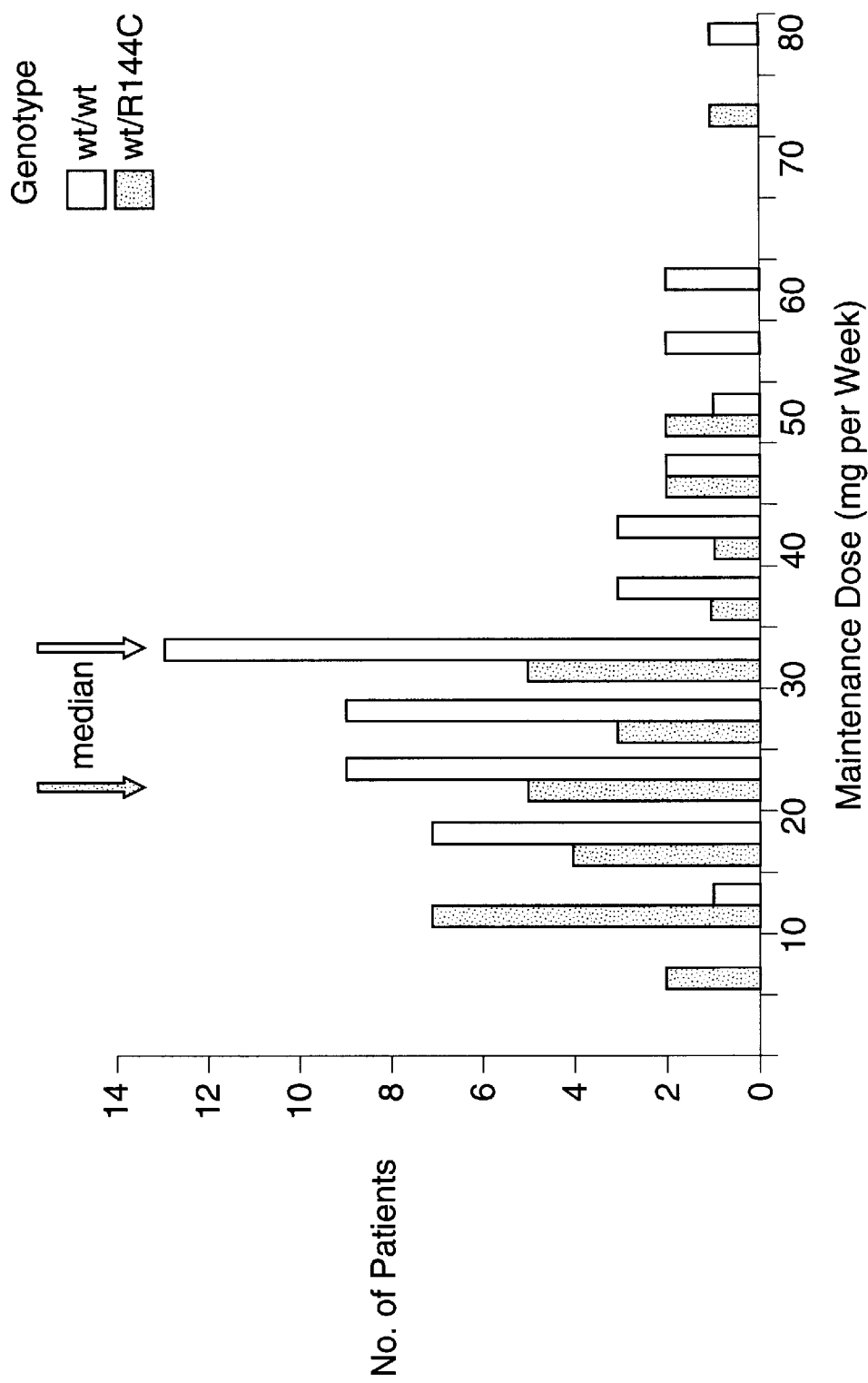

W = CYP2A6 wild-type
V = CYP2A6v mutant allele
? = not determined

FIG. 5

```
2A6 cDNA   GCGTGGTATTCAGCAACGGGGAGCGCGCCAAGCAGCTCCGGCGCTTCTCCAT
2A6 gene                                         T         TG
2A6 cDNA   CGCCACCCTGCGGGACTTCGGGGTGGGCAAGCGAGGCATCGAGGAGCGCATC
2A6 gene                  A            C
2A6 cDNA   CAGGAGGAGGCGGGCTTCCCTCATCGACGCCCTCCGGGGCACTGGC
2A6 gene           T              G  A      A        GCA
```

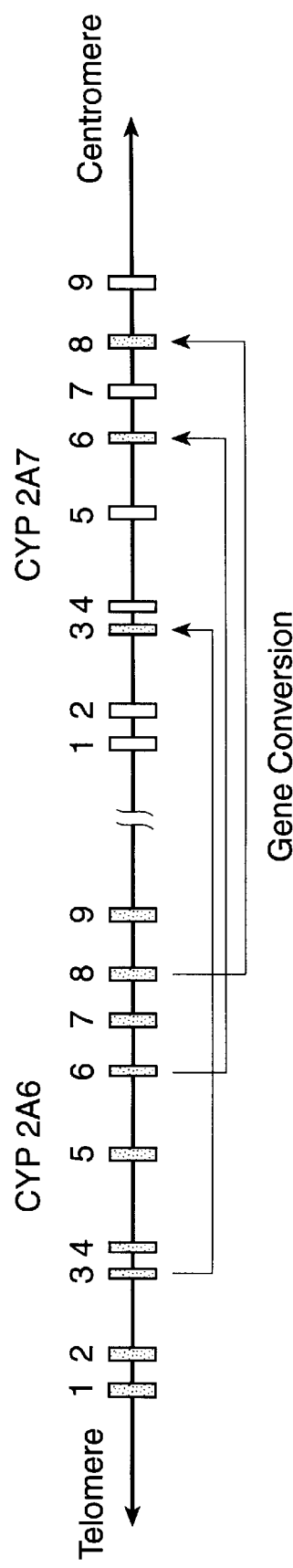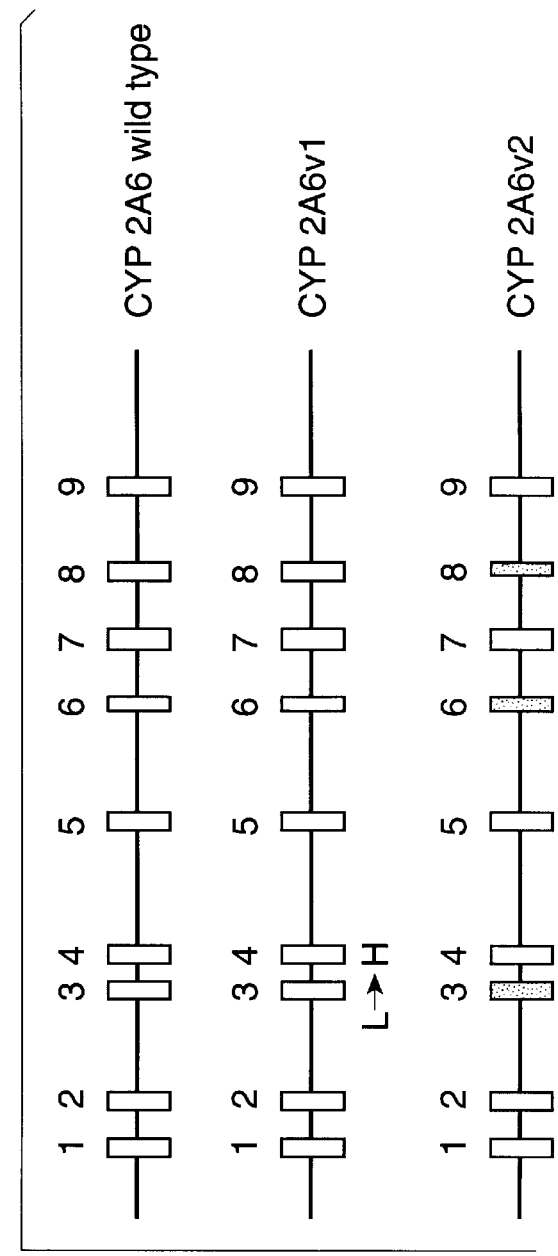

FIG. 9

5'<u>TCTACCACC</u>ATGCTGGCCTCAGGGATGCTTCTGGTGGCCTTGCTGGCCTGCCT
GACTGTGATGGTCTTGATGTCTGTTTGGCAGCAGAGGAAGAGCAAGGGGAA
GCTGCCTCCGGGACCCACCCCATTGCCCTTCATTGGAAACTACCTGCAGCTGA
ACACAGAGCAGATGTACAACTCCCTCATGAAGATCAGTGAGCGCTATGGCC
CCGTGTTCACCATTCACTTGGGGCCCCGGCGGGTCGTGGTGCTGTGTGGACATG
ATGCCGTCAGGGAGGCTCTGGTGGACCAGGCTGAGGAGTTCAGCGGGCGAGGC
GAGCAAGCCACCTTCGACTGGGTCTTCAAAGGCTATGGCGTGGTATTCAGCA
ACGGGGAGCGCGCCAAGCAGCTCCTGCGCTTTGCCATCGCCACCCTGAGGGACT
TCGGGGTGGGCAAGCGAGGCATCGAGGAGCGCATCCAGGAGGAGTCGGGCTTC
CTCATCGAGGCCATCCGGAGCACGCACGGCGCCAATATCGATCCCACCTTCTTC
CTGAGCCGCACAGTCTCCAATGTCATCAGCTCCATTGTCTTTGGGGACCGCTT
TGACTATAAGGACAAAGAGTTCCTGTCACTGTTGCGCATGATGCTAGGAAT
CTTCCAGTTCACGTCAACCTCCACGGGGCAGCTCTATGAGATGTTCTCTTCGG
TGATGAAACACCTGCCAGGACCACAGCAACAGGCCTTTCAGTTGCTGCAAGG
GCTGGAGGACTTCATAGCCAAGAAGGTGGAGCACAACCAGCGCACGCTGGA
TCCCAATTCCCCACGGGACTTCATTGACTCCTTTCTCATCCGCATGCAGGAGG
AGGAGAAGAACCCCAACACGGAGTTCTACTTGAAGAACCTGATGATGAGC
ACGTTGAACCTCTTCATTGCAGGCACCGAGACGGTCAGCACCACCCTGCACTA
TGGCTTCTTGCTGCTCATGAAGCACCCAGAGGTGGAGGCCAAGGTCCATGAG
GAGATTGACAGAGTGATCGGCAAGAACCGGCAGCCCAAGTTTGAGGACCGG
GCCAAGATGCCCTACATGGAGGCAGTGATCCACGAGATCCAAAGATTTGGA
GACGTGATCCCCATGAGTTTGGCCCGCAGAGTCAAAAAGGACACCAAGTTTC
GGGATTTCTTCCTCCCTAAGGGCATAGAAGTGTTCCCTATGTTGGGCTCCGTG
CTGAGAGACCTCAGGTTCTTCTCCAACCCCCGGGACTTCAATCCCCAGCACTTC
CTGGGTGAGAAGGGGCAGTTTAAGAAGCGTGATGCTTTTGTGCCCTTCTCCA
TCAGAAAGCGGAACTGTTTCGGAGAAGGCCTGGCCAGAATGGAGCTCTTTCT
CTTCTTCACCACCGTCATGCAGAACTTCCGCCTCAAGTCCTCCCAGTCACCTA
AGGACATTGACGTGTCCCCAAACACGTGGGCTTTGCCACGATCCCACGAAA
CTACACCATGAGCTTCCTGCCCCGCTGA<u>GCGAGGGCTGTGCCGGTGAAGGTCTG
GTGGGCGGGGCCAGGGAAAGGGCAGGCCAAGACCGGGCTTGGGAGAGGGGC
GCAGCTAAGACTGGGGGCAGGATGGCGGAAAGGAAGGGGCGTGGTGGCTAG
AGGGAAGAGAAGAAACAGAAGCGGCTCAGTTCACCTTGATAAGGTGCTTCC
GAGCTGGGATGAGAGGAAGGAAACCCTTACATTATGCTATGAAGAGTAGT
AATAATAGCAGCTCTTATTTCCTGA</u> 3'

FIG. 10A

```
   1  AAGTTCCCCT GAAATATGGC TCTGGTCTTC CTCCCCCTTGC CAATGAAGAA GATGGCAGTG
  61  GAGGTTCTAT GGCAGCCATC CTGGCCTCAC TCTGAGGTTC CAATGAGGAT TCTGGGCATC
 121  AAGAGACAGC TCTGGGCAAA GCTAAATCAA GTCAGCCCCT GACCCAGTG CTGGGCTGCT
 181  GGGCTTTCTG GGAGAACGCC GCTGGGCTTG CTCCTCCCAG AAACTCCACA
 241  CCCACAGCCC TGGGTCTTCC TAGCCCCGAG ACTTTCAAGT CCATATGCCT GGAATCCCCC
 301  TTCCTGAGAC CCTTAACCCT GCATCCTCCA CAACAGAAGA CCCCTAAATG CACAGCCACA
 361  CTTTGTCTTA CCCTAATAAA ACCCAGACCT TTGGATTCCT CTCCCCTGGA ACCCCAGAT
 421  CCGCACAACT TGGGGTGCA CAGACCCCAA ATCCAAAGCC CAAGTGCTCC
 481  CCTATGCAAA TATTCCAAAC TTCTCACTCT TACAGCTTAT CTGTTGCCCC CTCCTAAATC
 541  CACAGCCCTG CGGCACCCCT CCTGAAGTAC CACAGAGATTA GTCTGCTGGCT CCCCTCTCTG
 601  TTCAGCTGCC GTGGGTCCC CTTATCCTCC CTTGCTGGCT GTGTCCCAAG CTAGGCAGGA
 661  TTCATGGTGG GGCATGTAGT TGGGAGGTGA AATGAGGTAA TTATGTAATC AGCCAAAGTC
 721  CATCCCTCTT TTTCAGGCAG TATAAAGGCA GCCGTCACCA TCTATCATCC
 781  CTCTACCACC ATGCTGGCCT CAGGGATGCT TCTGGTGGCCT GCCTGACTGT
 841  GATGGTCTTG ATGTCTGTTT GGCAGCAGAG GAAGAGCAAG GGGAAGCTGC CTCCGGGACC
 901  CACCCCATTG CCCTTCATTG GAAACTACCT GCAGCTGAAC ACAGAGCAGA TGTACAACTC
 961  CCTCATGAAG GTGTCCCAAG ACAGGGAGAT GGGTGTCTCG GGGTGGGGGC TGCCTAGTTG
1021  GCTGGGGCTT TGTGCCAGGG GGTTGACCAG AGTCTTAGGA AATGGAGTTT
1081  TGGAGTTTCA GCATCAGAAA GACAGGATCT AGCTCCCTGA CTGTGAGAAC
1141  CTGGGTGCGA AGCATCCCAG CACATGACAT CTCGGTGCTG GGCCCCATTC AGAGTGGAGG
1201  GTTCTCCCCTC TAACCACTCC CACCCACCTC CATCAGATCA GTGAGCGCTA TGGCCCCGTG
1261  TTCACCATTC ACTTGGGGCC CCGGCGGGTC GTGGTGCTGT GTGGACATGA TGCCGTCAGG
1321  GAGGCTCTGG TGGACCAGGC TGAGGAGTTC AGCGGGCGAG GCGAGCAAGC CACCTTCGAC
1381  TGGGTCTTCA AAGGCTATGG TGCCCAAGAG GGGAAGGTG GCGCAGGTGGA CACGAAGGTC
1441  TCAGTGTTCC CAGCCTTTCC CTGACTCTC CTGACAACTG GAGGATAAGG GAGAGTCCCC
1501  AGTCTGGTCT TCCCTCCCCA TCTCCCTACA TGGGGCCTC TCCATGTGTA TCCCTCACCT
1561  GTCTCCAGCG GCCCTGTCCT GATTCCTCCC TGCCCCTCT CCTTATTCTC
1621  TCTCACTGGA GTCTCCTCTT TCCCCTCTCT CCCATCTCT AAGGACATCC TGGGTTTCTG
1681  TTTACCAGCC CTGGGTCTCT GTCTACATGA GTCTTTGAGG CCCTCTTAGC TTCTGGCTT
1741  CTCTGGGTTT CTCATCTCTC CGGATCCCTT TCTCAATTCT TCCTCTGTCT TAGGATGCCA
```

FIG. 10B

```
1801 GGGTTATTCC TACTTCCACA TCTTCAGGCT CCATCCCCTG GTAACAGTCT CTCTTCCTTC
1861 CAGACCCTCT CTGTTTCTAT CTCAATATTA AACTCTCTGC TCCAGCTCAG CTTAAGAATC
1921 TCACACCAAG AGAGGATGTC CTCCACCCAG ATCTCCCCAT ATCTCACTAC CCCACCCTCC
1981 ATCCTCTGCC TCCATCACTC TCTTTCTCTC CCCACTGCNC CTGCGGACGC GATCCAATGG
2041 AGTGTGGAGC TAATGCCGTG AAGCTATGTG CATCTCTCTG TCTGGCCGTA CCTGGTAAT
2101 AACCTGATCG ACTAGGCGTG GTATTCAGCA ACGGGAGCG CGCCAAGCAG CTCCTGCGCT
2161 TTGCCATCGC CACCCTGAGG GACTTCGGGG TGGGCAAGCG AGGCATCGAG GAGCGCATCC
2221 AGGAGGAGTC GGGCTTCCTC ATCGAGGCCA TCCGGAGCAC GCACGGTGAG CAGGGACCC
2281 CGAGTGCGGG GGCAGGAGAA GGAAAACACC CAGGACGAGG AACCCGCGCG CGTTCTGCCT
2341 GGGGATGGGG ACTAGGTGGG GAAAGGCGCC CGCACTTCCA GCCCTGGAGT CTGGCGCTGG
2401 GAATTTGGCT CAACAAGGCC CTGCCTCCTG GAATTCTGAC TCTCCTCAGA CCTCTGAGTT
2461 GACTCTCTCC CCAACCCCCT TCTCCCGACA TACCCGGAGG CGCCAATATC GATCCCACCT
2521 TCTTCCTGAG CCGCACAGTC TCCAATGTCA TCAGCTCCAT TGTCTTTGGG GACCGCTTTG
2581 ACTATAAGGA CAAAGAGTTC CTGTCACTGT TGCGCATGAT GCTAGGAATC TTCCAGTTCA
2641 CGTCAACCTC CAGCCCGCC CGTGAAGGCC CTTACCAAAA
        CGTCAACCTC CAGCCCGGCC CGTGAAGGCC CTTACCAAAA
2701 CCGGCAAATT GTTCCCCTAC CGGGGAAGG GGGCCACCGC TTCCCACCGC CCCCGGACA
2761 GTGTCCCCTC AAAATCAGTC CCCGATTTGG GCAAATTGGC AGAGTGGAAC CAGACCCGG
2821 TTGGTTGTCC AATCCCCTGC TCTCCAGGGA CACCGGGATA GCACAACAGA TGCTCCCCAA
2881 AACAGAGCCT GCTGGCAGGA TGCATACCCT CAGCTCAGCT CTCTCACCCT GGGCACGTGT
2941 TCCCATCCCC AACTTACCGG TAATTTCTAA CAGATGCTCC CTACCCAGGT CTTCTTGAAT
3001 ATTTTAACAC CGGAAACCC TGGGTACCTA ACCTTCCCTG TAAACTTTAG AGATTAGTTC
3061 CTATCCGGCC CCTCTGAAAT ACCTAACCAC CGGAGACCAG ATGCCTTTAA CTCAGTTCCT
3121 TCCTTGCTAT GAAACAAATC CCATTCCCAT CGGAGCTCCT GC CCGTGACAG CTGTCCTTCC
3181 CTTCCCATCC TCTCTCTGCA ACCCCAGCTC TATGAGATGT TCTCTTCGGT GATGAAACAC
3241 CTGCCAGGAC CGCAGCAACC AGGCCTTTCAG TTGCTGCAAG GGCTGGAGGA CTTCATAGCC
3301 AAGAAGGTGG AGCACAACCA GCGCACGCTG GATCCCAATT CCCACCGGGA CTTCATTGAC
3361 TCCTTTCTCA TCCGCATGCA GGAGGTACAC CCCAGCAGCC ACTGCGGGGA GATGCAAAGC
3421 CAGGCAGAGG TGGGAGTGGG TCACAATTGG GCAGGCAGAT GACACAGGCC CATTCAAATT
3481 AACCCTCATC ATAATAATCC GCAGGTGGAT CTGGGTGCCG TGGCTAACAG CCTGTAATCC
3541 CAGCACTTTG GGAGGCCGAG GCAGGTGGAT CACCTGAGT CAGGAGTTCG AGACCAGCCT
3601 GGCCAACATG GTCAAACCCC GTCTCTACTA AAAATCCAAA AATTAGTTGG GCATGGTGGC
```

FIG. 10C

```
3661  GCGAAGGGGG  GCAGAGGTTG  CAATGAGCCA  AGATCACGGC  ATTGCACTCC  AGTCTGGGTG
3721  ACAGAATGAG  GCCCTGTGTC  AAAAAAAATT  AATCACTTGT  TTAAAAAGTA  AGTGAGCCTG
3781  CATGGTCATG  CGCATGTGCA  GCTCCAGCTA  CTCAGGAGGC  TGAGGCTGGA  GGATTGCTTG
3841  AGCTCAGGAG  TTGGCGTCCG  GCCTGTGCAA  CCAAGTCAGT  CCAAGTCAGT  ATAAGAAAAA
3901  AAAAAAACAA  AAAAAAAGCT  GACAGCTAAG  TTGATAATTG  ACGGACAGAT  GGTCAGCAAG
3961  GTAACGAAGG  TGAGAAGGAA  GAGCATTGGG  GGCAACGCCA  GGAGTCAGGG  CAAGGGCTGG
4021  TTCCTAGAGC  GAGTCTTGTA  GGATCTAGGG  CCCCTCTTCT  CCACCCTGCG  GTCTTGCCCC
4081  AAAGAGAGGT  CGAGGGTGCT  GGGATTGCGC  TAGACTCGAG  TCTGTGTAGA  TCTTGGGGTC
4141  CCCTCTTGAC  CCCCATTGGT  CTGAACCTAA  GAGTGGAAGA  TCCATGGGGT  GAACCCTAG
4201  ATGGTGCCCT  GAGGTCAAGC  AGGAGTGAGG  TTGTCCTAAA  GCCCCCTCTC  CCTTCAGGAG
4261  GAGAAGAACC  CCAACAGGGA  GTTCTACTTG  AAGAACCTGA  TGATGAGCAC  GTTGAACCTC
4321  TTCATTGCAC  GCACCGAGAC  GGTCAGCACC  ACCCTGCACT  ATGGCTTCTT  ACTGCTCATG
4381  AAGCACCCAG  AGGTGGAGGG  TAAGGCTGGA  GGGGACGGA   AGTGAGGGC   CCCAGACCCT
4441  CAAAATTCCC  CTTCGACTGT  TGCAATGTCC  CCACCTGTCC  CAGATCCCGG  GACCCTGAGA
4501  CGTGACTTGC  TGTCCAGAGA  CAGGGCAACA  TTCAGCTGGT  AGGCATCAGC  TGAGTCTCAT
4561  TAGATATTAA  AATATTGAAA  ATGTCTGCAC  TGATTGGTCA  GTCACTTCTG  TCCCAAGCCC
4621  ACTGAGTGCC  CACTGCCCGT  TCCACCGGGT  CATCCCCCT   GTTCCTCCCT  GTGCCTCCCC
4681  TGTGATTCTG  GCACAACCTG  GTTAACAGGA  TCCTACTCCA  ACAATGCGAA  TGGGTGATGT
4741  CTGTTCTGTT  ATGAATGCTC  TACTTCCGTC  TCATAGGCGG  AGGCATTTCA  TCCACCCAT
4801  TTTGCCTATC  CGGACTATCA  TTTCCTGCTC  TGAGACCCCT  AGATACCTAA  ACACATTCCC
4861  CCTCCTCCCC  CAGCCAAGGT  CCATGAGGAG  ATTGACAGAG  TGATCGGCAA  GAACCGGCAG
4921  CCCAAGTTTG  AGGACCGGGC  CAAGATGCCC  TACATGGAGG  CAGTGATCCA  CGAGATCCAG
4981  AGATTGGAG   ACGTGATCCC  CATGAGTTTG  GCCCGCAGAG  TCAAAAAGGA  CACCAAGTTT
5041  CGGGATTTCT  TCCTCCCTAA  CATGTGTATC  GCCCCACCC   CCCAGACTAC  GGGACTCCA
5101  GCCCCTCTCT  GTGTCCCCAG  CATCCCACCC  ACATTAGAAG  CTTTCTAGAC  CCTGTCCCAC
5161  TCCCTCAATC  AGTCAAAAA   GACTTCCCCA  ACCACCACAT  CCGTTCCACC  TTTCCACTTA
5221  GACACTCCTG  AGTCCTGCAT  CTCTCCAGAC  TCTTTGTGTC  AGGAGAATCA  AACACATGTT
5281  CCCAAACTTC  CTATCTTAAG  AAACAGAAGC  CCCCTTTTCCA  TTCGGCCTTT  TGTCATAGGG
5341  ACAGAAATCT  CAGGTCCCCC  AAACTCCCGC  ATGGACCCCA  CTAGAAGGAC  TGTCTCCCAA
```

FIG. 10D

```
5401  ACTTCCTGTT TCAGAGATGT GAACCTTCTA TCCCCCAAGG TCCTCCCTCA GAGGTCCCCA
5461  ATTCCCATGC CTGCCACTTC CCCTCACCGG GGCACCCTAG TTCCCCCTCC AGCCCCTGTG
5521  TACTCTCAAC AATCCCCCAA CCCGCCTCAT CACATACACC TTCCTCCTCC CTCCAGGGC
5581  ATAGAAGTGT TCCCTATGTT GGGCTCCGTG CTGAGAGACC TCAGTTCTT CTCCAACCCC
5641  CGGGACTTCA ATCCCCAGCA CTTCCTGGGT GAGAAGGGGC AGTTTAAGAA GCGTGATGCT
5701  TTTGTGCCCT TCTCCATCAG TAAGAGACCA CTGTTTGGTG CCAGGCTTAC TACTCACACC
5761  AGCAGGGGCC TCCCTTACCC AGTTCCCCTC TCTGCCGTGT AGCCTAGTAT TTCCCCAGCT
5821  TGGCAAGTTC CTGTTAGCAA TCTACCGTCG AGCCACCAGG CCAGGCTTAC TTAACTACCA
5881  AGCACCCAGT ACCTGTGCCC AGGCAAAAGG AAAGGAAACA TGATACTCCC TTCAGAGGCG
5941  GGGGAAAACC AGAATCAGA GAGATGACGG GATTTATTTC TCATACCCCT AGTTCTTATC
6001  TCTTCAGCAT CCCTAAAAAG ACCTCCCATT CACAGCAGGT CCTAGGGTCA AACCCCATCT
6061  TGGGGAAGG GGGATCTTAA CTCAAGGAAA GTGAGGTCAA GGCATCGATC GAGGCTCCCT
6121  TTTGGTCATC TTTTGGGTCA TATATTCCAC CCTTCCTCCC GGAGGGTCAA CATATTTGGG AGTTCTTATC
6181  CTTAAAGTCT CTCAGGGCCA GCACTGAGAG CCTCCTCCC TGGGAGAGCC GCAGCTGGAG
6241  GTCGGTACTG GGGCGAGGCT GTTTCGGAGA AGGCCTGGCC CTCCACCCCT CCCGCCTCTC
6301  CTCCTCAGGA AAGCGGAACT ACTTCCGCCT CAAGTCCTCC AGAATGGAGC TCTTTCTCTT
6361  CTTCACCACC GTCATGCAGA GCTTTGCCAC GATCCCACGA CAGTCACCTA AGGACATTGA
6421  CGTGTCCCCC AAACACGTGG GCTTTGCCAC GATCCCACGA AACTACACCA TGAGCTTCCT
6481  GCCCCGCTGA GCGAGGGCTG TGCCGGTGAA GGTCTGGTGG GCGGGGCCAG GGAAAGGGCA
6541  GGGCCAAGAC CGGGCTTGGG AGAGGGGCGC AGCTAAGACT GCGGGGCAGGA TGGCGGAAAG
6601  GAAGGGGCGT GGTGGCTAGA GGGAAGAGAA GAAACAGAAG CGGCTCAGTT CACCTTGATA
6661  AGGTGCTTCC GAGCTGGGAT CCTGAGCACG TACCCCCGTG ATTATGCTAT GAAGAGTAGT
6721  AATAATAGCA GCTCTTATTT CCACAAAAAC CCCTTCGAAG TCACCTTTGT TCAAAAACCA
6781  TTGCACGCTC ACCTAATTTG TAGAAAGTTG TCTCTGATGT GGGCGTTCAT GCCCATTTTA
6841  CACGTGACAA AACTGAGGCT TAGCCTTCTA CTCACAAAAC ATAAGTGCCC
6901  AGAAAATCTG CGAACACAGA TCTGTGCCCA AATCACATGG GACAGATTCT TAAAAGCAC
6961  CTATTCCTCA CGCAAAACAG TTTAGTATAG CCCTGCCTTC CCTGAACATC CCTGTCCGGG
7021  GGAGTTCCCC AGAGACCTGG GGGTGGTTG GGTGTAATCT ACTGCACACA TGCCCACACT
7081  CTCACCTACT CAACATGCTG TGACTACCCG GGTGTAATCT GTGCTTGCTA CCAGATAAGG
7141  CCACCTGAGC CCATTCAGAG TCAGCCCAGG TCAGCCCAGG CCCTAGGATG GGTATTGCTA GACATACAGG
7201  GTCAGTCCAT TAACAA
```

FIG. 11

5' <u>ATGGCCACC</u>ATGCTGGCCTCAGGGCTGCTTCTGGTGACCTTGCTGGCCTGCCT
GACTGTGATGGTCTTGATGTCAGTCTGGCGGCAGAGGAAGAGCAGGGGAA
GCTGCCTCCGGGACCCACCCCATTGCCCTTCATTGGAAACTACCTCCAGCTGAA
CACAGAGCAGATGTACAACTCCCTCATGAAGATCAGTGAGCGCTATGGCCCT
GTGTTCACCATTCACTTGGGGCCCCGGCGGGTCGTGGTGCTGTGCGGACATGAT
GCCGTCAAGGAGGCTCTGGTGGACCAGGCTGAGGAGTTCAGCGGGCGAGGCGA
GCAGGCCACCTTCGACTGGCTCTTCAAAGGCTATGGCGTGGCGTTCAGCAACG
GGGAGCGCGCCAAGCAGCTCCGGCGCTTCTCCATCGCCACCCTAAGGGGTTTTG
GCGTGGGCAAGCGCGGCATCGAGGAACGCATCCAGGAGGAGGCGGGCTTCCTC
ATCGACGCCCTCCGGGGCACGCACGGCGCCAATATCGATCCCACCTTCTTCCTG
AGCCGCACAGTCTCCAATGTCATCAGCTCCATTGTCTTTGGGGACCGCTTTGA
CTATGAGGACAAAGAGTTCCTGTCACTGTTGCGCATGATGCTGGGAAGGTTC
CAGTTCACGGGAACCTCCACGGGGCAGCTCTATGAGATGTTCTCTTCGGTGAT
GAAACACCTGCCAGGACCACAGCAACAGGCCTTTAAGGAGCTGCAAGGGCT
GGAGGACTTCATCGCCAAGAAGGTGGAGCACAACCAGCGCACGCTGGATCCC
AATTCCCCACGGGACTTCATCGACTCCTTTCTCATCCGCATGCAGGAGGAGGA
GAAGAACCCCAACACAGAGTTCTACTTGAAGAACCTGGTGATGACCACCCT
GAACCTCTTCTTTGCGGGCACTGAGACCGTGAGCACCACCCTGCGCTACGGTTT
CCTGCTGCTCATGAAGCACCCAGAGGTGGAGGCCAAGGTCCATGAGGAGATT
GACAGAGTGATCGGCAAGAACCGGCAGCCCAAGTTTGAGGACCGGGCCAAG
ATGCCCTACACAGAGGCAGTGATCCACGAGATCCAAAGATTTGGAGACATG
CTCCCCATGGGTTTGGCCCACAGGGTCAACAAGGACACCAAGTTTCGGGATT
TCTTCCTCCCTAAGGGCACTGAAGTGTTCCCTATGCTGGGCTCCGAGCTGAGA
GACCCCAGGTTCTTCTCCAACCCCCAGGACTGCAGTCCCCAGCACTTCCTGGAT
GAGAAGGGGCAGTTTAAGAAGAGTGATGCTTTTGTGCCCTTTTCCATCGGA
AAGCGGTACTGTTTTGGAGAAGGCCTGGCCAGAATGGAGCTCTTTCTCTTCT
TCACCACCATCATGCAGAACTTTCGCTTCAAGTCCCCTCAGTCGCCTAAGGAT
ATCGACGTGTCCCCCAAACACGTGGGCTTTGCCACGATCCCACGAAACTACAC
CATGAGCTTCCTGCCCCGCTGA<u>GCGAGGGCTGTGCTGGTGCAGGGCTGGTGGGC
GGGGCCAGGGAAACGGCCGGGGCAGGGCGGGGCTTGTGGGAGGGCGGGGCT
AAGAATGGGGGCAGTGGGGGAAGGAAGGGGAGAGGTGGTTAGAGGGAACA
GAAGAAACAGAAGGGGCTCAGTTCACCTTGATGATGTCCTTCAGAGCTGTG
ATGAGAGGAAGGGAAACCTTACAGTATGCTACAAAGAGTAGTAATAATA
GCAGCTCTTATCTCCTGA</u> 3'

FIG. 12A

```
   1 TGGGTCCAAC CAAAATCAAA GTCAATTCCC TGGGCCCAGT GCTGGGCTGC TGGGCTTTTC
  61 TGGGAGCACC TGCTGGGCTT GCTACACACT CCACCTCCCA GAAACTCCAC ACCCACAGCC
 121 CTGGGTCTTC CTAGCCCCAA GACTTTCAAG TCCATATGCC TGGAATCCCC CGTCCTGAGA
 181 CCCTTAACCC TGCATCCTCC ACAACAGAAG ACCCCCAGAT GCACAGCCAC ACTTCCATCT
 241 CACCCTAGTA AAACCCAGAC CTTGGATTC CAGATCCCAA CTCTCCCGTG GAATGCCCAA ATCCACAACT
 301 TTGGGTGCA GTCTCACTCC CAGATCCCAA ATCCAAAGAC CAGGTGCTCC CCTGTGCAAA
 361 TATTCCAAAC TCCTCAGTTC CACAGTTTAT CTGTTGCCCG CTCCTAAATC CACAGGCCCT
 421 GCAGCAACCC TCCTGAAGTA GCAGAGTTAG ACTGGAGTTC CCCTCCCTGT TCATCTTGCC
 481 CTGGGGTCCC TCTCCTCCTC CCTTGCTGGC TGTGTCCTAA GCTGTGTGGG ATTCAGGGTT
 541 GGGGTGTAGT TGGGAGGTGA AATGAGGTGA TTATATAATC AACCACAGTC CATCCCTCTT
 601 TTTCAGGCAG TATAAAGGCA AACCACCCA GCCATCACCA TCTATCATCC CATGGCCACC
 661 ATGCTGGCCT CAGGGCTGCT TCTGGTGACC TTGCTGGCCT GCCTGACTGT GATGGTCTTG
 721 ATGTCAGTCT GGCGGCAGAG GAAGAGCAGG GGGAAGCTGC CTCCGGGACC CACCCCATTG
 781 CCCTTTCATTG GAAACTACCT CCAGCTGAAC ACAGAGCAGA TGTACAACTC CCTCATGAAG
 841 GTGTCCTAAG GCAGGAGATG GGTGGCACGG GGTGGGGGCT GCCCAGTTGG CTGGGCTTA
 901 GTGGCAGGGG ATTGACCAGT GTGGACCAGA GTCTTAGGAA GTCTTAGGAA AGGGAGTCTT GGAGTTTCAG
 961 CATCAGGGTC CTAGCAGGAA AGACAGGATC TTGGGATGTC CAGCTCCCTG ACTGTGAGAA
1021 CCTGGGGGGC GAAGCATCCC AGTACATGAT ATCTCAGCGC TGGGCCCATT CAGAGTGGGG
1081 GCTGCTCCCT CTAACCACTC CCACCTGCCT CCAACAGATC AGTGAGCGCT ATGGCCCTGT
1141 GTTCACCATT CACTTGGGGC CCCGGCGGGT CGTGGTGCTG TGCGGACATG ATGCCGTCAA
1201 GGAGGCTCTG GTGGACCAGG CTGAGGAGTT CAGCGGGCGA GGCGAGCAGG CCACCTTCGA
1261 CTGGCTCTTC AAAGGCTATG GTGAGGGGGT GCCAAGAGGG GGAAGGTGGT CAGGTGGATG
1321 CAATGCCCCA CGTGTCCCCA GCCTTCTCCC TGACTCTCCT GCCCACTGGA GGATATGGGA
1381 GAGCCCCCTG TCTGGTCTTC TCTCCTACATC TCCCTCCCCA GGGGACTCTC CCTGTGAGTC
1441 CCACACCTGT CTCCAGCGCC CCTGGCGTGA GCCTTCCCC CCTCTCTCTG CCCGTCTCCC
1501 TCCTTCTCTC CTCAGCCTCT CCCTCCTTAC CCCTCTCTCT CCATCTCTGA GGACATCCGG
1561 GGTTTCTGTT TACCAGCCCT GGTCCCTCTGT CTTCATTTGT CTTTTTGTCG CTCTCGGCTT
```

FIG. 12B

```
1621  CTGTGCTTCT CCGTGTTTCT CCTCTCTCTG CTTCCCCTCTC CCACTTCTTC CTCTGTCTTA
1681  GGATTTCAGG GTATTCCTAC TTCCACATCT CCAGCTCCCA ACTCCTGGTA ATTGTCTGTC
1741  CTCCTTCCCG ATCCTCTCTG TTTCTGTCTC CATATTTTTC TCTCTCTTCT CCAGTTCAGA
1801  TTAAGAATCT TTCACCATTT TTATTCCCTC CTCCCAGATC TCCCCATATC TCACTTCCCC
1861  TCCCTCCATC TCTCTCTTTC TCTCCCCACT ACCTTCCCTT CCTCCATGGA GTATCCCCGT
1921  ATCCCTCTGT TTCTCTGCAT CTGTCTGTCT GGCCTTTCTG CTTCTCTTCT GATTCTCTTA
1981  TTCTTTCTAC CCGGACTCTC TCTCTCTCTC TCTCTCTCTC TCTCTCTCTC TCTCTCTCTC
2041  TCTCTCTCTC TCTCTCTCGT GCTCTCGTGT TTCTCTGACT GAGAGTGTAG CTCTCCTGGG
2101  CACTCGCGCT GAATCCATCT CTCTCCCACA CCACTCCCTC TCTACACCAC CCTTGGGGAG
2161  CCCCTTGGAA CTGGTCCGCT CCTGCTACCA CCACCCCCTG ACCTCTCTCC ACCCCGCGT
2221  TCACCTCCCC AGGCGTGGCG TTCAGCAACG GGGAGCGCGC CAAGCAGCTC CGGCGCTTCT
2281  CCATCGCCAC CCTAAGGGGT TTTGGCGTGG GCAAGCGCGG CATCGAGGAA CGCATCCAGG
2341  AGGAGGCGGG CTTCCTCATC GACGCCCTCC GGGGCACGCA CGGTGAGTAG GGGACCCCGA
2401  GTGCGAGGGC GGGAACCCGC GCTTTCTGCC TGGGGATGGG GACTAGGTGG GGAAAGGGGC
2461  CCGCACTTCC AGCCCTGGAG TCTGGCGCTG GGATTCGGCT CAACAGGGCC CTGCCTCCTG
2521  GAATTCTGAC TCTCCTCAGA CCTCTGAGTT GACTCTCTCC CCAACCCCCC TTCTCCCGCC
2581  ACACCTGTAG GCGCCAATAT CGATCCCACC TTCTTCCTGA GCCCACAGT CTCCAATGTC
2641  ATCAGCTCCA TTGTCTTTGG GGACCGCTTT GACTATGAGG ACAAAGAGTT CCTGTCACTG
2701  TTGCGCATGA TGCTGGGAAG GTTCCAGTTC ACGGGAACCT CCACGGGGCA GGTAACTGGA
2761  TGCAGCCCGC CAGTGACGCC CCTACCACAA CCTGCCAACT GCTCCCCTAC CTGGAGACAG
2821  GTGCCCCAAA CTCCCACCCC CCTCCAGACA GTGTCCCCTC AAAATCAGTC CCCGATATTG
2881  GACAACTGGA CGGTTGGACC AGAACCCAGG AGGGATGCCC CTGGCAGGAT CTCCAAGGAC
2941  ACCTGGATAG CTCAACAGAT GATCCCCAAA ACAGAGCCTG CTTACCGTAA GCATACCCTC
3001  AGCTCAGCTC TCTCACCTGG GCACATGTTC CCATCCCCAT CAAGTGACTG TTTGTAACAG
3061  GTGCTCCCTA CCCAGTTCTT CTGAATATTT AACACCTGGA CCATCATAAT TGTCAACCCG
3121  CCTCCTGCAT ACCTGAACAC CTGGTGCTGC AAAATCCAGG CCAAGGCCCC CATTTCACAT
3181  CTACACAAAT GTCACAGATT AGCCCACTGG TAATATCTGG CCAAGGCCCC TCTACTTCAC
3241  CCACTTAAAT GCCTGAAAAC ATGGACAGGT GCCCTAACCA ATACCCTAAA CACATAAATA
3301  TCTAGATAGA TTATTCCCTG ACACCCAAAT AAGTGTTCCC CAACCCTTTC AATCACACA
3361  CCTTACAGAG GTGCTCCCAG TGCATCCCAC TTGGATAGGT AAACACCTCA ACAGGTATCC
```

FIG. 12C

```
3421  CCTCCACTTC  AGCATCTTCA  CCAGCCCCAC  TTTATACCTG  AGCACCTGAA  CAAAAGCCCC
3481  CAATCCAGAC  CCAGTAAGTA  TCTGGACAGC  TGTCTCCAAC  CAAGTCCACT  TGAATGCCTA
3541  AATACCTAGA  CAGGTGCCAC  TCACCTCATA  CCAGCCCCAC  CTGAAGAGCT  AAACACCTGG
3601  ACAGGTGTCT  TCCAACTCAA  CTTCACTTGA  ATATCTGAAC  ACCTAGATGT  GTGCTCCAAT
3661  CCAGCCTCAT  TTGCATACCT  GAAACCTGGA  TATATGCCTC  AGTTCTTCTC  ACCTAAATTA
3721  CTAGACCGTG  CCCCTGGCAC  CTAATCCACG  TGAAAACTTA  GATATAAGTT  TCCATCCAAC
3781  CCCACTGAAA  TACCTAAACA  CCTGGACAGA  TGCCTTTAAC  TCCGTTCCTT  CCTTGCTATG
3841  AAACAAATCC  CCATTCCCAT  CAGCTCCTGC  CCCGTGACAG  CTGTCCTTCC  CTTCCCATCC
3901  TCTCTCTGCA  ACCCCAGCTC  TATGAGATGT  TCTCTTCGT   GATGAAACAC  CTGCCAGGAC
3961  CACAGCAACA  GGCCTTTAAG  GAGCTGCAAG  GGCTGGAGGA  CTTCATCGCC  AAGAAGGTGG
4021  AGCACAACCA  GCGCACGCTG  GATCCCAATT  CCCCACGGA   CTTCATCGAC  TCCTTTCTCA
4081  TCCGCATGCA  GGAGGTACAT  CCCAGCAGCC  AGTGCAGGCA  GGTGCAAAGC  CAGGGAGAGG
4141  GAAATCAGGA  TGGGAGTGGG  GTGGCAGAGC  GACACAGGCC  CATTCAAATT  AGCCCTCGTC
4201  ATAATAATCC  TTACAATTGG  CCAGGCGCGG  TGGCTCATGA  CCTGTAATCC  CAGCACTTTG
4261  GGAGGCCGAG  GCAGGTGGAT  CACCTGAGGT  CAGGAGTTCG  AGACCAGCCT  GGCCAACATG
4321  GTGAAACCCC  GTCTCTACTA  AAAATACAAA  AATGAGCTAG  GTATGGTGGC  ATGCGCCTGT
4381  AATCCCAGCT  ACTCAGGAGG  CTGAGACAGA  AGAATTTGTT  TGAATCCGGG  AGGCAGAGGT
4441  TGCAGTGAGC  CGGGATCATG  CCACTGCACT  CCGGCCTGAG  TGACAGAGCA  AGACCCTGTA
4501  AAAAAAAAA   AAAAAAAAAA  AAAAAATTCC  GGAAAACCCC  AATTACATCA  CCCACTGCTG
4561  TCCCATCTAC  TGAGCCCTCA  CCCACAAGGA  CGGGTTATGG  AGGTGGATTA  GATTGGAAAG
4621  AACTTCTCAA  GAACTACCGG  GTGCCAGGAA  CTGGGTTAAG  TGTTTTATGA  TAGTCCGCCA
4681  TGGAACACTT  TTAACAGTTC  TTGAGGGAGG  TTCACTCATG  GCCCCAGTTG  TACAAATGAG
4741  GAAACTGAGG  CCCAGAGAGT  TTAAGTGTCT  TAACTGAGGT  CACAACAGTG  AGGAAGACCA
4801  TGGTCCCCCT  AGCTCAAACC  CTGGTCTCTC  TGAGCCTATA  GCTGGTGCTT  TTAGCCACCA
4861  TGCTCTCTAA  CCGTTCATGT  CCTGGTTAGC  TGACAGCACCT AGACACACCT  CTGTGGACAG  GTGACCTGGC
4921  TTTACATTGC  AGGGTCCCCG  CCTACCCTG   GATGTCAGCC  TCCCATGTGG  GAAGGCTTTA
4981  GGAAGCCAAA  GCTCAGGGAG  AAAGGATCAA  GGGAGGGATT  CCTCCACAGT  AAGTTTCAAG
```

FIG. 12D

```
5041 ATTTTTAGGG AAGAAATAGG ATGCTGTTGC TTAAAATTCT GTGCTTGTAT CTCAGAAAAA
5101 CTCTTTTTT CTGACTCTTC ATCTTGCCAT CTCTGTACTA CTTTCTCTTC GTCTCCCCTC
5161 ATCCTTCTCT TTCCAAATAT TCCTATCATT AAAAAAGTAA CAGACTGGGA AACATGCAA
5221 AACCCCGTCT GTACAAAAAA ATGGCTAGGC ATGGTGGTGC ATGCCTGCGG TCCCAGCTAC
5281 TAAGGAGGTT GAGGTGGGAG GATATCTTGA GCCCAGGGTG GGCAGAGGTT TCAATGAGCC
5341 GATATCACAG CCCTGCCCTC CAGCCTGGGT GACAGAATAA GACCGTGTCT CCCAAAAAAA
5401 AAAAGAATTA ATTTTTAAC AGTTAACAAG TGAGCCTGCA TAGTCATGTG CATGTGCAGT
5461 TCCAGCTACT CTGGAGGCTG AGACCGGAGG ATTCCTTGAA CCCAGGAGTT GGAGTCCAGC
5521 CTGTGCAACT TAGCAAGACC AAGTCTGCAT AAAAAAAAA AAAACCAACT GACAGCTAAG
5581 TTGACAATTA AAGGATAGAT GATCAGTGAG GTAAAGAAGG TGAGAAGGAA GAGCATTTTG
5641 GGCAAAGCCA GCAAGCCAGG CAAGGGCTGG AACCTGGAGC GAGTTTGGCA AATCTAGGGT
5701 CCCTCTTTCC ACCTTTGGTC TGGACCAAAG AGAGGTAGCT CCAAAGGAAA AGCCCTAGAA
5761 GGGCCCCAAG AGCATGGAGA GTGAGCTTGG TCTAAACCGC CCTCTCCCTG CAGGAGGAGA
5821 AGAACCCCAA CACAGAGTTC TACTTGAAGA ACCTGGTGAT GACCACCCTG AACCTCTTCT
5881 TTGCGGGCAC TGAGACCGTG AGCACCACCC TGCGCTACGG TTTCCTGCTG CTCATGAAGC
5941 ACCCAGAGGT GGAGGGTAAG ACTGGAAAGG GAGGAAAGTG AAGGGCCCCA GACCCTCAAA
6001 ACTCCCCTGA GCCTGGTGCA GTGTACCCAC CTATCCCAGA TCCCAGGACC CTGAGCGTG
6061 CCTTGCTGTC CAGAGACAGG ACAATATTCA GCTGATAGGC ATCAGCTGAG TCTCATTAGC
6121 TATTAAAATA TTGAAAATGT CTGCACTGAT TGGTCAGTCA CTCCTGTCCC AAGCCCACTG
6181 AGTGTCCGCT GCCTGCTCCT CTGGATCATC CCCTAAGTTC CTCCCCTGTC CTACCCTGTG
6241 ATTCTGACAC AACCTGGTTT AACAGGGATC CTGCTGCAAA CAATGCGAAT GGGTGATGTC
6301 TTGTTCTTGT TTATGAATGG GCTTACCCTT CGTGTCAGAG GTGGAAGCTA TGTCAACCGC
6361 CGTGTTTTAG CTAGGGGGGG CGATACATGC CCTGCTCTAA GACCCCTAGA GAGGGTAAAG
6421 ATATTCCCCT CCTCCGCCAG CCAAGGTCCA TGAGGAGATT GACAGAGTGA TCGGCAAGAA
6481 CCGGCAGCCC AAGTTTGAGG ACCGGGCCAA GATGCCCTAC GACAGAGGCA TGATCCACGA
6541 GATCCAAAGA TTTGGAGACA TGCTCCCCAT GGGTTTGGCC ACAGGGTCA ACAAGGACAC
6601 CAAGTTTCGG GATTTCTTCC TCCCCTAAGGT GCTGTCTCCC CTCCACCACC ACCACTCAGA
6661 CTACGGGGAC TTCCAGCCTC CCAGAATCC CCCAGAATCC TGCCCCCATT AGTGTTCTAG
6721 ACTCTGTCCC ACTCCCCTCAA TCAGTCAAAA AAGACTTCCA ATCTGTTCCA
6781 CCTTTCCACT TAGACAGTCC TGAGTCCTGC ATCTCGCCAG ACTCTTTGTG TCAGGAGAAT
```

FIG. 12E

```
6841  ACACCCCATG TTCCCAATCT TCCTGTCTTA AGAAACAGAA GCCCCCTTTC CATTAGGCCT
6901  TGTGGCTTAG GGACACAAAT CTCAGGTCCC TCAAACACCC TGGCTAGTGG AACATGGACC
6961  CCATGTCTCC CAAACTTCCT GTCTCAGAGA CATGAAACTT CTATCCCCCA AAGCTCCTCC
7021  CTCAGAGGTC CCCAACTCCT CCATGTCGTG CCACTCCCCG CACCTGGGGG ACCCTAGAGC
7081  CCCCTGGAGC CCCTGTGTAC TTTCACCAAT CCCCCAACC TGGCTCATAA CACACACCTT
7141  CCTCCTCCCT CCCAGGGCAC TGAAGTGTTC CCTATGCTGG GCTCCGAGCT GAGAGACCCC
7201  AGGTTCTTCT CCAACCCCCA GGACTGCAGT CCCCAGCACT TCCTGGATGA GAAGGGGCAG
7261  TTTAAGAAGA GTGATGCTTT TGTGCCCTTT TCCATCGGTA AGAGACACTG TTTGCTGCCA
7321  GGCCACGGCT CACACCAGCA GGGGCCTCTC CCCCTCCTCTG CGGTGTAGCC
7381  TGGTATTTCT CCAGCTTGGA AGTTCCTGTT AGAATCTACC ATTGAGCCGC CACCAGCTGA
7441  TACTCCCTTA ACTGCCAAGC ACCCAATACC TGCGCCCAGG TAAAAGGGAA GGAAACATCT
7501  TCCCCCATAG ATTTATTTGT CTAGGGTCAC ACAGCAGATT CTTCAGCTCC CTGAAAAGGA
7561  GATAATGGTA CAGCACAGCA GTCATATTTG CAAGTGTATC TGGGGGTAG GGGCATCTAA
7621  ACCTCCCATT GCTACACCTG GCATGGATCA CCCCATCTAT GATGGAGGCA TGACATTATG
7681  CCTTTTTCGA AACCCATAGA ACTGTATAAC ACAGAGTAAA CCCTAATGTA AACTATGGAC
7741  TTTGGTTAGT AATAATATAT CAATATTGGT TCACCATTGT TATATCTCTT ATAGAAGGAA
7801  ACTGAAGCTC AGGGAGGATC GGAGTCTCCT CTGAAAGTCT CTCAGGCCAT AATATTCCCA
7861  CCCCTCCTCC CTAGAGAGTG CAGCCGGGGG TCAGTAGGGG TTGAGGCTGC ACTGAGAGTG
7921  GGCTTCACCT TCACCCCTCC TGCCTCTCCT CCTCAGGAAA GCGGTACTGT TTTGGAGAAG
7981  GCCTGGCCAG AATGGAGCTC TTTCTCTTCT CATGCAGAAC TTTCGCTTCA
8041  AGTCCCCTCA GTCGCCTAAG GATATGCGACT TGTCCCCCAA ACACGTGGGC TTTGCCACGA
8101  TCCCACGAAA CTACACCATG AGCTTCCTGC CCCGCTGAGC GAGGGCTGTG CTGGTGCAGG
8161  GCTGGTGGGC GGGGCCCAGG AAACGGCCGG GGCAGGGGCG GGGCTTGTGG GAGGGGCGGG
8221  GCTAAGAATG GGGGCAGTGG GGAAGGAAG GGGAGAGGTG GTTAGAGGGA ACAGAAGAAA
8281  CAGAGGGGC TCAGTTCACC TTGATGATGT CCTTCAGAGC TGTGATGAGA GGAAGGGAAA
8341  CCTTACAGTA TGCTACAAAG AGTAGTAATA ATAGCAGCTC TTATCTCCTG AACAAGTCCC
8401  TCCCTGTCAG CTTTGTTCAA AAAGCGTTGC ACGCTCACCT CACTTATTTG CCACACACCT
8461  CTACCAATGG GGGAAAAGTC TTCATTCCCC TTTTTACACG TGAGAAAGGT GCGGCTCAGA
8521  AAGTTGTCTC TATCTGAAAA CTCACAAAAC GCAAGTGTCC AGAGGATCTT GGAACACAGA
8581  TCTGGGCCCA TAGCCCTCTA GATCGATCCT CACCATAGCA CCCCTTCTTC ACGTAAAATA
8641  GCTTAGTATA GCATCACATG GCCTGAACAC CCCTGGGCCG GGGGTTCCC CAGAGACCTG
8701  GCGGGCGGCT GCCCTGCCTA CTCTGTACAC CCCTGGGCCG GGACGATCC GGGCACCAGG
8761  GTGTCACCTG AGCTCGCTA
```

DEFECTS IN DRUG METABOLISM

FIELD OF THE INVENTION

The invention relates to genetic material, specifically primers, for use in a method designed to determine the genotype of an individual; and also a kit, including the genetic material of the invention, for performing the method of the invention.

BACKGROUND OF THE INVENTION

It is well known that genetic polymorphisms in drug metabolizing genes give rise to a variety of phenotypes. This information has been used to advantage in the past for developing genetic assays that predict phenotype and thus predict an individual's ability to metabolize a given drug. The information is of particular value in determining the likely side effects and therapeutic failures of various drugs. The availability of this sort of information will result in routine phenotyping being recommended for certain categories of patients.

Drug metabolism is carried out by the cytochrome P450 family of enzymes. For example, the cytochrome P450 isozyme gene, CYP2C9 encodes a high affinity hepatic [S]-warfarin 7-hydroxylase which appears to be principally responsible for the metabolic clearance of the most potent enantiomer of warfarin. Similarly, the cytochrome P450 isozyme gene, CYP2A6, encodes a protein that metabolizes nicotine and coumarin and activates the tobacco-specific nitrosamine 4-(methyinitrosamino)-1-(3-pyridyl)-1-butanone) (NNK).

It is of note that the above gene products are also known to metabolize other substrates, for example, the CYP2C9 gene product is also known to metabolize Tolbutamide, Phenytoin, Ibuprofen, Naproxen, Tienilic acid, Diclofenac and Tetrahydrocannabinol.

It follows that genetic polymorphisms or mutations in either of the two aforementioned genes can lead to an impairment in metabolism of at least the aforementioned drugs.

In so far as CYP2C9 is concerned, sequences reported by Yasumori et al (1987 *J. Biochem.* 102:1075–1082.) and Kimura et al (1987 *Nuc. Acids Res.* 15:10053–10054) show differences at several positions including a C to T base change that results in a Arginine/Cysteine polymorphism at amino acid 144. This polymorphism has been designated R144C.

In so far as CYP2A6 is concerned, a T to A base change at position 488 of the cDNA sequence described by Yamano et al (1990 *Biochemistry* 29:1322–1329) results in substitution of Leucine 160 by Histidine. Henceforth this mutant form of the gene will be designated CYP2A6v1.

The variant CYP2A6v1 encodes an enzyme that is unstable and catalytically inactive. It is found in the general population at a frequency of about 1% but does not account for all slow metabolizers of coumarin.

Since the cDNA sequence structure of CYP2C9 and CYP2A6 are known, and since it is also known to perform genetic assays to determine whether a preselected mutation is present within a given gene, it should, in theory, be possible to design assays which specifically determine whether either of the aforementioned mutations are present in each of the respective aforementioned genes.

However, we have found an extraordinarily high degree of exon homology in the cytochrome P450 genes. This has resulted in non-specific binding of assay materials and poor performance of assays. In the instance where primers have been used to hybridize to genetic material, non-specific binding of such primers has taken place, and in the further instance where primers have been used to hybridize to genetic material with a view to performing a polymerase chain reactions we have found that related genes have also been amplified, for example, CYP2A7, CYP2A12 and CYP2C8 have also been amplified.

SUMMARY OF THE INVENTION

The present invention relates to novel variant alleles in cytochrome P450 genes which express enzymes involved in the metabolism of particular drugs and/or chemical carcinogens.

One object of the present invention relates to the discovery of new mutant or variant CYP2A6 alleles wherein the human gene is characterized. A new variant allele has been found which is designated CYP2A6v2. The cDNA and genomic sequence of CYP2A6v2 is provided in the present invention. Another new gene related to CYP2A6 has been discovered and is designated CYP2A13. The cDNA and genomic sequence of CYP2A13 is provided in the present invention.

Another object of the present invention relates to the use of intron sequences to specifically identify CYP2A6 and CYP2C9 variants in a gene specific detection assay.

Another object of the present invention is to use an oligonucleotide probe, specific for regions unique to a particular CYP2 variant to screen for the presence or absence of the variant in a sample.

Yet another object of the invention is to provide genetic material, a method, and a kit which enable genotyping of the CYP2C9 and CYP2A6 gene with a view to providing phenotypic information concerning drug metabolism.

A further object of the present invention provides a method for diagnostically determining the sensitivity of a patient for specific drugs and chemical carcinogens. Such a method is widely applicable in determining the proper dosage of a drug for a patient.

Another object of the present invention provides a method of genotyping CYP2A6 and CYP2C9 and determining whether a mutation has altered the sequence of these genes and hence altered sensitivity to particular drugs and chemical carcinogens.

In accordance with the present invention a method is provided which utilizes the finding that each variant of a CYP2 gene has specific nucleotide differences as compared with the wild-type CYP2 gene. Such nucleotide changes can be utilized in a probe-hybridization assay, which is capable of specifically detecting a chosen variant and not other variants.

The present invention also provides a genotyping method for identifying the presence or absence of a mutation at codon 144 of the coding sequence of CYP2C9, or alternatively, at codon 160 of the coding sequence of CYP2A6, or alternatively, a gene conversion event involving CYP2A6 and CYP2A7 in exons 3, 6 or 8 comprising use of a portion of DNA. Such a mutation is then correlated to the sensitivity of particular drugs and chemical carcinogens.

The present invention further relates to a gene-specific bioassay which is capable of distinguishing between the CYP2 genes and identify the presence or absence of a mutation in CYP2A6 and CYP2C9 genes. Such a bioassay can diagnostically predict the sensitivity of an individual to particular drugs or chemical carcinogens. For example, the CYP2C9 variants identify a sensitivity to a commonly used anti-coagulant drug, warfarin. The CYP2A6 variants identify sensitivity to coumarin, nicotine and nitrosamines. The sensitivity to nicotine may be used to predict a predisposition to tobacco-related diseases, a propensity to smoking and adverse reactions to exposure to nicotine. Further, CYP2A6 genes are associated with the activation of nitrosamines, elevated levels of which have been correlated with many cancers.

The present invention also provides a method of genotyping the CYP2A6 and CYP2C9 genes using allele-specific amplification reaction.

In addition, a highly-specific combination genotyping bioassay has been developed to identify mutations within CYP2A6 and CYP2C9 which are linked to sensitivity to particular drugs and chemical carcinogens. This combination bioassay comprises a gene-specific amplification reaction, an exon-specific amplification reaction and an endonuclease cleavage reaction wherein only one form, either mutant or wild-type is cleaved, producing either a single nucleic acid fragment or multiply nucleic acid fragments depending upon the presence or absence of the mutation. For example, one CYP2C9 variant, R144C, which contains a $C_{472} \rightarrow T$ mutation can be identified by an AvaII restriction site. CYP2A6 variants can also be identified by their corresponding mutations. CYP2A6v1 which contains a $T_{488} \rightarrow A$ mutation can be identified by a XcmI restriction site. CYP2A6v2 which contains a $T_{415} \rightarrow A$ mutation can be identified by a DdeI restriction site.

The present invention also relates to a method for screening patients for drug sensitivity prior to their treatment with that drug, thereby alerting a physician of a drug sensitivity. In addition, the method may be used to screen patients for a predisposition to cancers related to excessive nitrosamine activation, which are associated with mutations within the CYP2A6 gene locus. Further, the method may be used to screen patients for a sensitivity to chemical carcinogens, based upon the genotype of the CYP2A6 and/or CYP2C9 alleles.

One such new allele variant, CYP2A6v2, has 98% nucleotide similarity and 80% amino acid similarity with the wild type CYP2A6, respectively. The present invention relates to the new CYP2A6v2 variant, the cDNA sequence and its genomic sequence wherein the alterations in sequence are within exons 3, 6 and 8, which are attributed to a gene conversion. In addition, another new gene, also involved in drug metabolism has been identified, and has been designated CYP2A13. This gene plays a similar role in drug metabolism as CYP2A6. These new gene sequences or fragments thereof are used as probes in identifying specific CYP2 variants in samples. In additions, fragments of the new genes are used as primers in a genotyping assay.

The invention further provides isolated CYP2Av2 and CYP2A13 cDNAs for use in gene therapy and replacement protocols for individuals who are predisposed to sensitivity to needed drugs or to chemical or environmental carcinogens.

In accordance with an aspect of the present invention, there are provided primary human cells which are genetically engineered with CYP2A6v2 or CYP2A13 DNA (RNA) which encodes a therapeutic agent of interest, and the genetically engineered cells are employed as a therapeutic agent. (The term "therapeutic," as used herein, includes treatment and/or prophylaxis.) Gene expression in an organism in accordance with the practices of this invention is regulated, inhibited and/or controlled by incorporating in or along with the genetic material of the organism non-native DNA which transcribes to produce an RNA which is complementary to and capable of binding or hybridizing to a mRNA produced by a gene located within said organism. Upon binding to or hybridization with the mRNA, the translation of the MRNA is prevented. Consequently, the protein coded for by the mRNA is not produced. In the instance where the mRNA translated product, e.g. protein, is vital to the growth of the organism or cellular material, the organism is so transformed or altered such that it becomes, at least, disabled.

Accordingly, in the practices of this invention from a genetic point of view as evidenced by gene expression, new organisms are readily produced. Further, the practices of this invention provide a powerful tool or technique for altering gene expression or organisms through gene therapy. The practices of this invention may cause the organisms to be disabled or incapable of functioning normally or may impart special properties thereto. The DNA of CYP2A6v2 or CYP2A13 employed in the practices of this invention can be incorporated into the treated or effected organisms by direct introduction into the nucleus of a eukaryotic organism or by way of a plasmid or suitable vector containing the special DNA of this invention in the case of a procaryotic organism.

BRIEF DESCRIPTION OF THE DRAWINGS

Embodiments of the invention are described by way of example only with reference to the accompanying figures wherein:

FIG. 1 Shows the sequence of exon 2, intron 2 and exon 3 of CYP2C8 and CYP2C9, cDNA sequences (from 4) are shown at the top of the page together with sequences from 6 genomic clones encompassing exon 2, intron 2 and exon 3 of CYP2C8 and CYP2C9. The position of the polymorphism at codon 144 of CYP2C9 and the PCR primers are indicated.

FIG. 2 Shows the sequence of intron 2, exon 3 and intron 3 of CYP2A6, CYP2A7 and CYP2A12. The position of the polymorphism at codon 160 in CYP2A6 and the PCR primers are indicated.

FIG. 3 Shows the detection of CYP2C9 $Arg_{144}$ Cys polymorphism by PCR. Following amplification, samples were digested with AvaII and analyzed on a 1.8% agarose gel. Lane I and lanes 3 to 6 show homozygous wild-type subjects, lane 2 a heterozygous individual and lane 7 undigested PCR product.

FIG. 5 Shows distribution of the weekly maintenance doses for warfarin in patients (n=57) homozygous for the CYP2C9 wild-type allele (open bars) and heterozygous (n=37) for the R144C mutant allele (solid bars). Arrows show the median weekly dose requirement of warfarin for each genotype.

FIG. 6 Represents 7-hydroxylation of coumarin (%) in a family genotyped for the CYP2A6 and CYP2A6v1 alleles, showing a subject homozygous for the CYP2A6v1 allele who is deficient in coumarin 7-hydroxylation.

FIGS. 9a through 9c. Shows the detection of CYP2A6v2 by PCR. (FIG. 9A) gene-specific amplification by PCR of the CYP2A6 gene using E3F and E3R. Lanes 1 to 4 show the 7.8 Kb band obtained from several representative human genomic DNA templates, lane 5 correspond to a negative control in the absence of template and lane 6 contains 1 Kb DNA ladder (GIBCO BRL) as six markers. (FIG. 9B) Exon-specific PCR amplification of exon 3 from the 7.8 Kb long-PCR product and restriction endonuclease pattern obtained after digestion with XcmI (left) and DdeI (right) to detect the CYP2A6v1 and CYP2A6v2 alleles, respectively. The genotypes shown correspond to: wild type (+/+), heterozygous (+/−) and homozygous (−/−) subjects. (C) The genotyping strategy which has been developed. Exons are indicated by boxes. The position of the corresponding primer pairs are indicated by horizontal arrows. XcmI and DdeI restriction sites generate digestion patterns for the different alleles having fragment sizes as shown.

FIG. 10 Schematic diagram depicting methodology underlying a CYP2C9 genotyping assay.

FIG. 11. CYP2A6v2 cDNA sequence (SEQ ID NO: 1).

FIG. 12. CYP2A6v2 genomic DNA sequence having 7216 base pairs (SEQ ID NO: 3)

FIG. 14. CYP2A13 genomic DNA sequence having 8779 base pairs (SEQ ID NO: 4).

FIG. 15. Agarose minigel electrophoresis of PCR products. The CYP2C9 wild-type allele (Arg-144) and R144C respectively, Lanes marked "+/+" and "+/−" contain homozygous wild types and heterozygotes respectively. the right-hand lane contains a 100 bp ladder.

DETAILED DESCRIPTION OF THE INVENTION

Figure 4:
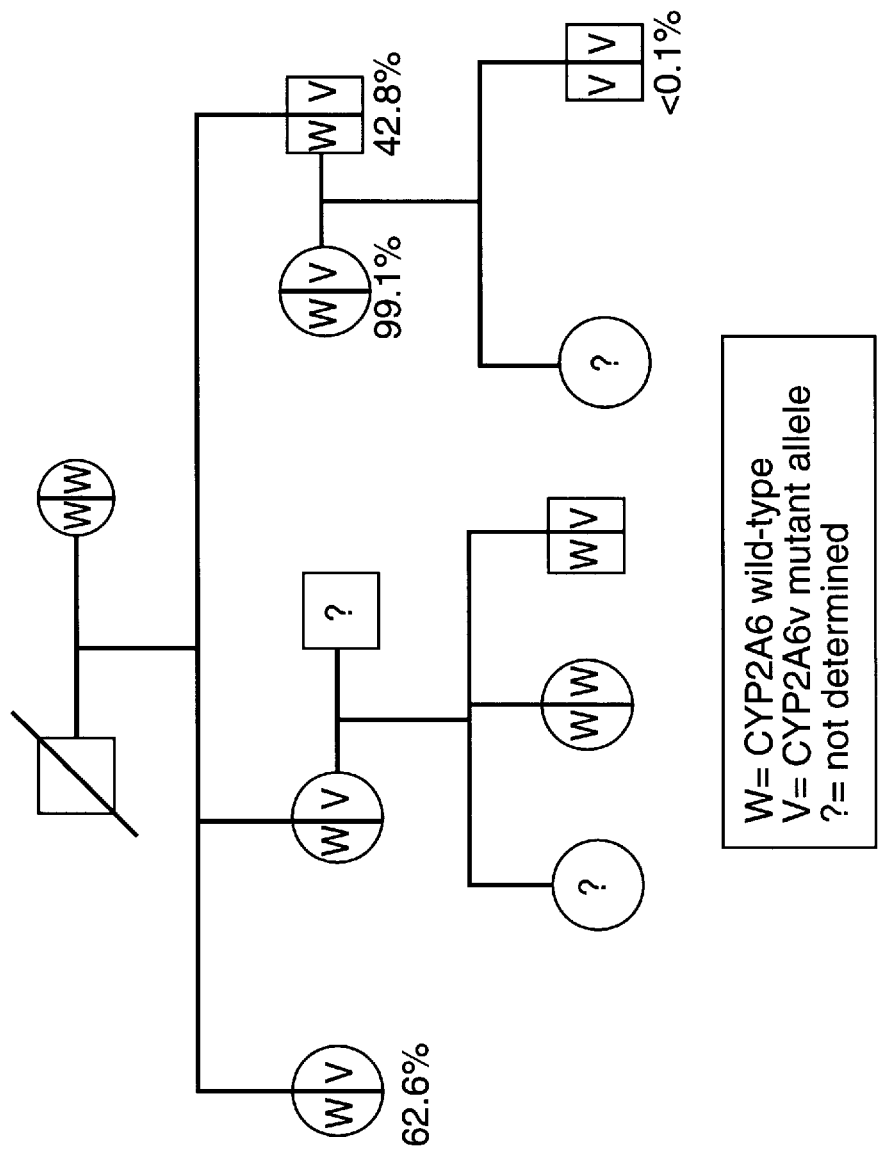
FIG. 4 Shows detection of CYP2A6 $Leu_{160}$. His polymorphism by PCR. Two parallel PCR reactions were carried out and the products analyzed on a 1% agarose gel. Lanes 1, 3, 5 and 7 show the results of the wild-type specific assay and lanes 2, 4, 6 and 8 the results of the variant-specific assay for the same four subjects. Subjects I and 2 (lanes 1–4) are homozygous wild-type, subject 3 (lanes 5 and 6) heterozygous and subject 4 (lanes 7 and 8) homozygous for the mutation.

The cytochrome P450 isozyme gene, CYP2C9 encodes a high affinity hepatic [S]-warfarin 7-hydroxylase which appears to be principally responsible for the metabolic clearance of the most potent enantiomer of warfarin along with metabolizing a number of other drugs and chemical carcinogens. Similarly, the cytochrome P450 isozyme gene, CYP2A6, encodes a protein that metabolizes nicotine, coumarin and a host of other drugs and chemical carcinogens CYP2A6 also activates the tobacco-specific nitrosamine 4-(methylnitrosamino)-1-(3-pyridyl)-1-butanone (herein referred to as "NNK"). Many cancers have been associated with activation and/or accumulation of nitrosamines. The present invention allows detection of a predisposition to such cancers.

It is of note that the above gene products are also known to metabolize other substrates. For example, the CYP2C9 gene product is also known to metabolize Tolbutamide, Phenytoin, Ibuprofen, Imipramine, Naproxen, Tienilic acid, Diclofenac and Tetrahydrocannabinol and hence can also be used to detect sensitivities to these drugs. A list of CYP2C9 drug substrates has been documented and is incorporated herein by reference (Gonzalez & Idle 1994 Clin. Pharmacokinet 26:59–70). Hence, the present invention can be used to screen for sensitivities to these drugs.

In addition, CYP2C9 has been associated with the metabolism of chemical carcinogens, such as polycyclic aromatic hydrocarbons. For example, the most ubiquitous environmental carcinogen, benz-[a]-pyrene is metabolized by CYP2C9. Benz-[a]-pyrene is found in tobacco, barbecued meats, car exhaust and generally, in polluted air. This compound, as it accumulates in the body becomes a potent DNA intercalating agent, ultimately resulting in cell transformation and the formation of tumors. The present invention provides a diagnostic method of screening individuals for their ability to metabolize and hence inactivate benz-[a]-pyrene. For example, a homozygote wild-type CYP2C9 individual would be better able to tolerate high levels of benz-[a]-pyrene than a heterozygote of the CYP2C9 allele.

Similarly, the CYP2A6 allele is associated with drug sensitivity and carcinogen metabolism. Coumarin sensitivity is directly related to the presence of a variant CYP2A6 allele, such as CYP2A6v1, CYP2A6v2 and also CYP2A13. Coumarin is a drug used in treatment of neoplastic diseases, such as lymphomas. (See Martindale: The Extra Pharmacopoeia 1993 Ed. Reynolds, J. E. F., The Pharmaceutical Press, London, p. 1358). Its suggested dosage is very high. Therefore, the present invention is useful in determining a patient's sensitivity to the drug in order to prescribe a proper dosage and avoid toxicity.

Another drug, Thiotepa™, is used in the treatment of a variety of neoplastic diseases, such as in treating women with breast cancer and children with brain tumors. Thiotepa is metabolized by CYP2A6 into Tepa, which is an intermediate more therapeutically potent than Thiotepa. Therefore, if a patient has a very active CYP2A6 enzyme, it is likely the patient will require lower doses of Thiotepa to provide a therapeutically effective amount. As one can see, the dosage provided to a patient is dependent upon the rate a patient is capable of metabolizing activating the drug. The present invention has identified variant alleles whose enzymatic activity is compromised. In addition, the present invention provides a simple method of genotyping patients for Thiotepa drug sensitivity. With information concerning patient sensitivity to such drugs, the proper dosage can be provided, hence maximizing drug efficiency and minimizing drug toxicity.

Further, CYP2A6 has been associated with nicotine metabolism. In addition to being an active ingredient in tobacco, nicotine also has several clinical uses. Nicotine is used clinically to treat various neurological disorders, such as Parkinson's disease and Alzheimer's disease. In addition, nicotine is used to treat tobacco addiction. In all of these situations, it is important to know a patient's sensitivity to nicotine, since extremely sensitive patients will become violently ill upon administration of nicotine. Therefore the present invention provides a method of identifying nicotine-sensitive patients by genotyping a patient's CYP2A6 allele. The present invention also provides a convenient method for determining an individual's general predisposition to using tobacco based upon their sensitivity to nicotine.

In addition, CYP2A6 is involved in activating nitrosamines, thereby producing the potent carcinogen NNK. Increased levels of NNK have been associated with a variety of cancers, including but not limited to lung cancer, nasal-pharynx cancers, throat cancers and colon cancers. In general, elevated levels of CYP2A6 has been associated with cancers associated with exposure to nitrosamines. The present invention may detect a patient's predisposition to such cancers. The presence of a CYP2A6 gene or a variant thereof will affect the likelihood that procarcinogens present in tobacco smoke will be activated into carcinogenic nitrosamines and nitrosamine-derivatives and therefore result in the development of a cancer.

It follows that genetic polymorphisms or mutations in either of the two aforementioned genes can lead to an impairment in metabolism of at least the aforementioned drugs and chemical carcinogens.

The present invention relates to the identification of the absence or presence of mutations in CYP2C9 and CYP2A6 and thus predict the phenotype of an individual and so predict whether and how an individual is likely to metabolize particular drugs and chemical carcinogens. For instance, the R144C mutation arising from a $C_{472} \rightarrow T$ base substitution in the CYP2C9 gene results in a reduction in warfarin metabolism. This implies that patients with this mutation receiving warfarin require a lower dose to maintain an anticoagulation target than those patients who do not have the mutation and are also receiving warfarin. Conversely, homozygous wild-types require higher doses in order to maintain an anticoagulation target.

"Mutation", as the term is used herein denotes an allelic variation of a known sequence, which alters the expressed gene product's activity. Such a variation need not completely inactivate the gene product's activity but merely alter it.

Similarly, one mutation within CYP2A6v1 arising from a $T_{488} \rightarrow A$ base change results in substitution of Leucine 160 by Histidine. Another CYP2A6 variant, CYP2A6v2, has been identified which differs from CYP2A6 in the regions of exons 3, 6 and 8. One particular mutation in CYP2A6v2, $T_{415} \rightarrow A$ mutation is useful in the assay of the present invention. These substitutions are very useful in detecting predispositions to cancers associated with tobacco and activation of nitrosamines. The normal CYP2A6 enzyme functions in the metabolism of nicotine, one of the carcinogenic compounds in tobacco.

Figure 8:
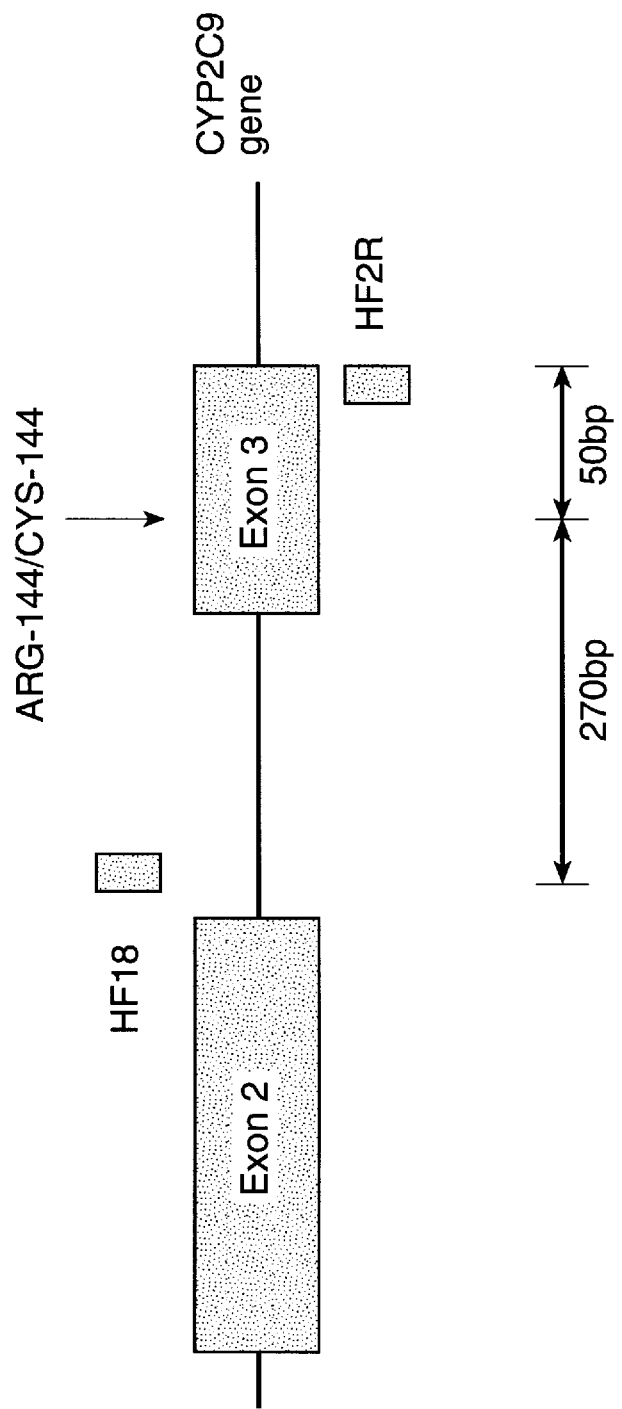
FIGS. 8a and b. Shows the conversion event which leads to the CYP2A6v2 allele.
Figure 13:
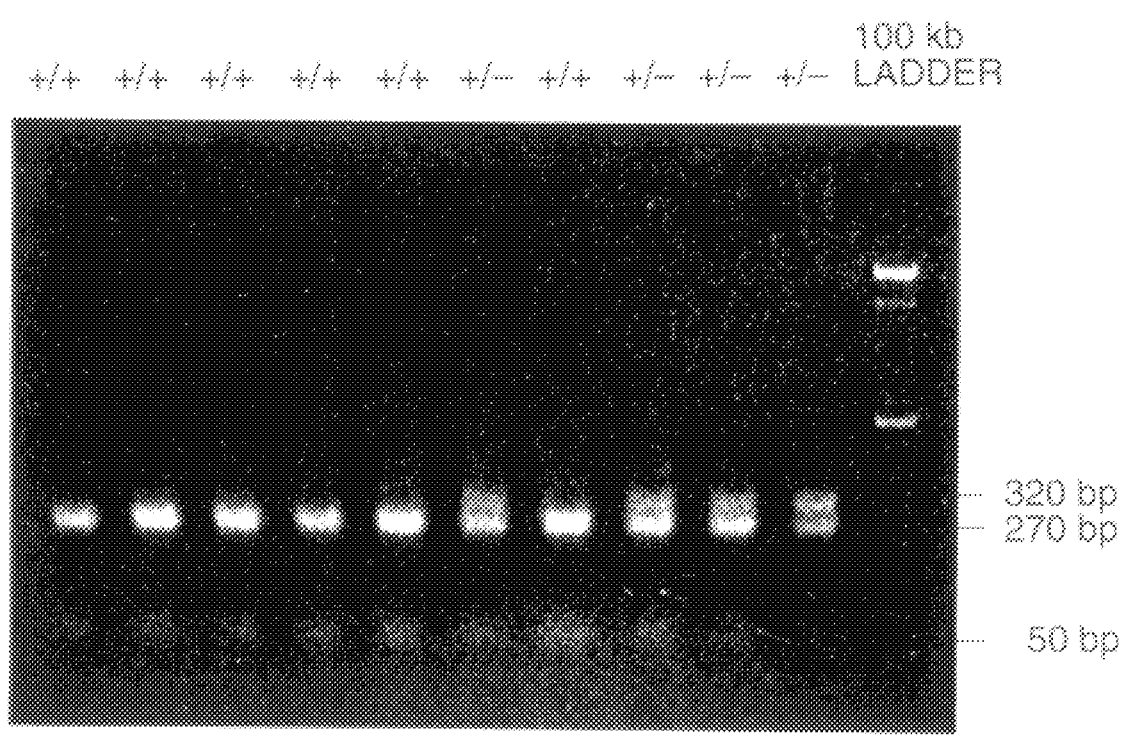
FIG. 13. CYP 2A13 CDNA sequence (SEQ ID NO: 2).

In addition, the present invention relates to the identification of a new variant of CYP2A6 designated CYP2A6v2. The variations of CYP2A6v2 from CYP2A6 bear sequence relatedness with the corresponding exons of the CYP2A7 gene, suggesting a recent gene conversion. The cDNA and genomic sequence for this gene is provided in the present invention. Hence, at least three different allelic variants of CYP2A6 exist and are illustrated in FIG. 8. These allelic variants include CYP2A6, CYP2A6v1 and CYP2A6v2.

Further, the present invention relates to a new CYP2A gene, designated CYP2A13. This gene produces an inactive form of CYP2A6, however variants at particular positions, including amino acid positions 117, 209 and 365 produce an enzyme which may alter the enzyme's activity and hence affect drug sensitivity. These mutations in CYP2A6 are likely to result in a deficiency or impaired activity of one of the enzymes responsible, for example, for metabolizing drugs, nicotine and nitrosamines.

CYP2A13 is considered a new cytochrome P450 gene. However, since the CYP2A13 gene product has a similar function as the CYP2A6, it is discussed herein as a variant of CYP2A6. That is, assays using the specific mutated amino acid positions 117, 209 and 365 of CYP2A13 and detecting variations at those positions are indicative of CYP2A6-like variant functions.

In one embodiment, the CYP2A6v2 or CYP2A13 proteins or functional portions thereof are expressed as recombinant genes in a cell, so that the cells may be transplanted into an individual in need of gene therapy due to the predisposition to a carcinogen-associated cancer or a sensitivity to a drug. To provide gene therapy to an individual, a genetic sequence which encodes for all or part of the CYP2A6v2 or CYP2A13 ligands are inserted into vectors and introduced into host cells. Examples of vectors that may be used in gene therapy include, but are not limited to, defective retroviral, adenoviral, or other viral vectors (see, e.g., Mulligan, R. C., 1993, *Science*, 260:926–932). The means by which the vector carrying the gene may be introduced into the cell includes, but is not limited to, microinjection, electroporation, transduction, or transfection using DEA-dextran, lipofection, calcium phosphate or other procedures known to the skilled routineer (see, e.g., Sambrook et. al. (Eds.), 1989, In "Molecular Cloning. A Laboratory Manual", Cold Spring Harbor Press, Plainview, N.Y.). Examples of cells into which the vector carrying the gene may be introduced include, but are not limited to, continuous culture cells, such as COS, NIH/3T3, and primary or culture cells of the relevant tissue type.

More specifically, there is provided a method of enhancing the therapeutic effects of blood cells, that are infused in a patient, comprising: (i) inserting into the blood cells of a patient a DNA (RNA) segment encoding CYP2A6v2 or CYP2A13 gene product that enhances the therapeutic effects of the blood cells; and (ii) introducing cells resulting from step (i) into the patient under conditions such that the cells resulting from step (i) "target" to a tissue site. In the alternative, as previously described the cells are not "targeted" and functions as a systemic therapeutic. The genes are inserted in such a manner that the patient's transformed blood cell will produce the agent in the patient's body. In the case of antigen-specific blood cells which are specific for an antigen present at the tissue site, the specificity of the blood cells for the antigen is not lost when the cell produces the product.

Alternatively, as hereinabove indicated, CYP2A6v2 or CYP2A13 DNA (RNA) may be inserted into the blood cells of a patient, in vivo, by administering such DNA (RNA) in a vehicle which targets such blood cells.

Further details regarding methods of gene therapy are provided in Anderson et al., U.S. Pat. No. 5,399,343 which is herewith incorporated herein by reference.

In another embodiment, antisense CYP2A6v2 or CYP2A13 DNA or RNA may be used to control the expression of CYP2 gene. For example, antisense therapy may be used to control CYP2A6's ability to activate dangerous nitrosamines by curbing its expression. Methods of producing such antisense molecules are described in U.S. Pat. No. 5,190,931, which is incorporated herein by reference.

Developing a genotyping assay, which could distinguish the CYP2 genes of interest from other cytochrome P450 genes required careful engineering since these genes have a high degree of sequence homology. To overcome this problem, one embodiment of the present invention has elucidated the genomic sequence structure of CYP2C9 and CYP2A6 with a view to making, in part, intron specific primers. That is to say primers which, in part, hybridize to at least one intron, preferably an intron adjacent to an exon including the mutation of interest, in the gene to be examined. Since there is less homology between the introns of cytochrome P450 genes, it has been found that using intron specific primers, gene specific assay can be undertaken. The present invention has a further advantage of using intron specific primers in so far as the use of such primers facilitates the manufacture of an optimum length of DNA which in turn facilitates the specificity of the instant bioassay.

A "genotyping" assay as the term is used herein refers to any diagnostic or predictive test to detect the presence or absence of allelic variants of a known gene sequence at a specified gene locus. Two gene loci are of particular interest in the present invention, CYP2A6 and CYP2C9.

Figure 7A:
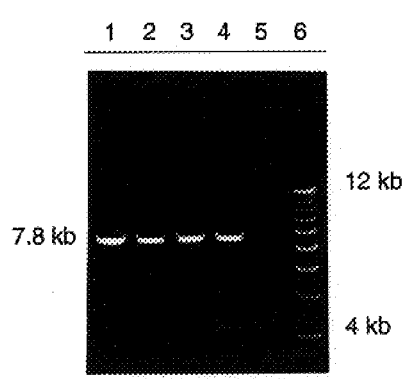
FIG. 7 Shows the difference between the genomic and cDNA sequences for the CYP2A6 gene.
Figure 7B:
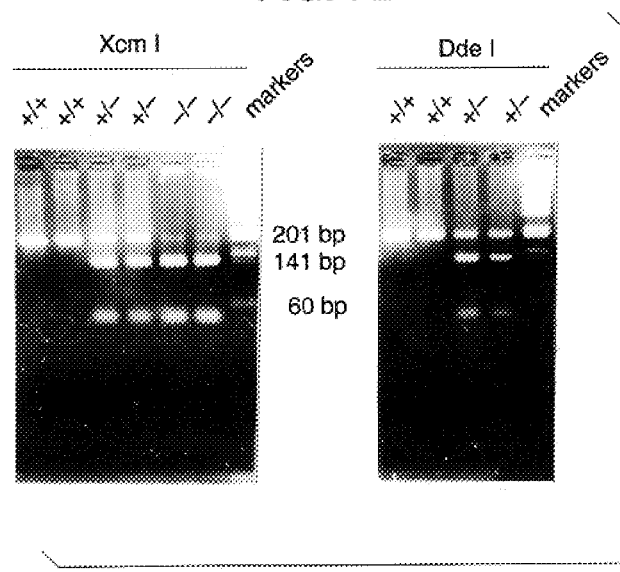
Figure 7C:
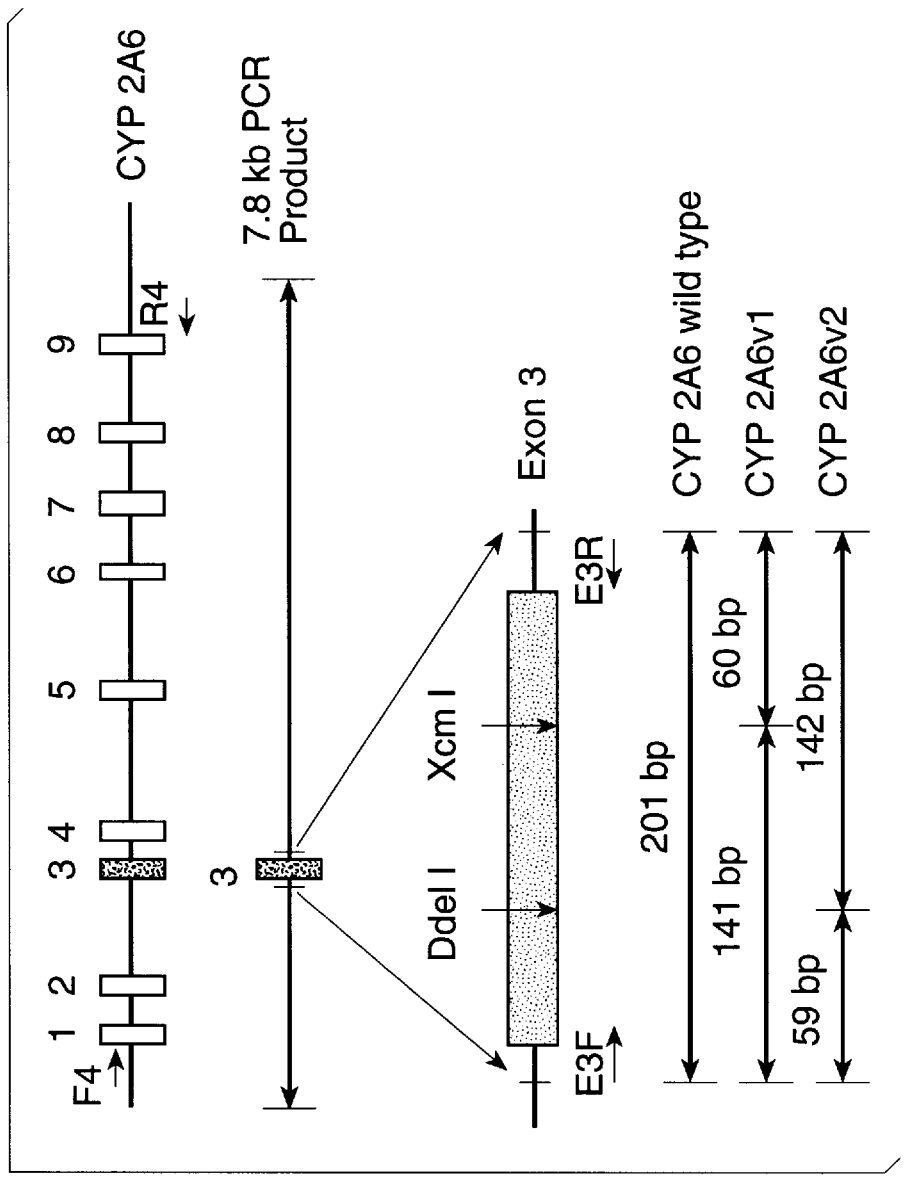

Further, the present invention relates to differences between the genomic DNA sequence structure and the cDNA sequence structure, as illustrated in FIG. 7. As a result, primers directed at the genomic sequence structure have been developed which are more reliable.

Several methods are provided for identifying the presence or absence of a mutation at codon 144 of the coding sequence of CYP2C9, or alternatively, at codon 160 of the coding sequence of CYP2A6, or alternatively, a gene conversion event involving CYP2A6 and CYP2A7 in exons 3, 6 or 8 comprising a DNA encompassing the region of a CYP2 gene unique to that variant.

One such method relates to an assay which contemplates the use of one specific primer which specifically encompasses the region containing the mutation, and a second primer which is complementary to another portion of the gene. The second primer sequence chosen is based upon the CYP2A6, CYP2C9 or CYP2A13 sequences as set forth in FIGS. 12, 1 and 14, respectively, depending upon the preferred size of the amplification product. One skilled in the art will know how to select second primer based on the region of gene chosen for amplification. These primers need not be identical to a given sequence but must be sufficiently complementary to hybridize to the target region in a specific manner. In short, the primers are preferably at least substantially homologous to the nucleic acid sequence provided.

Nucleic acid sequences includes, but is not limited to, DNA, RNA or cDNA. Nucleic acid sequence as used herein refers to an isolated nucleic acid sequence. Substantially homologous as used herein refers to substantial correspondence between the nucleic acid primer sequence of as described herein and that of any other nucleic acid sequence. Substantially homologous means about 50–100% homologous homology, preferably by about 70–100% homology, and most preferably about 90–100% homology between the particular sequence discussed and that of any other nucleic acid sequence.

In the instant application, the term "primer" is further used to designate a molecule comprising at least three nucleotides, the exact length being determined by the requisite amount of DNA needed, under given reaction conditions, to bind to or interact with a test sample so as to identify the presence or absence of either of said mutations. Preferably, the primer is usually between 15 and ideally about 20 to 50 oligonucleotides in length.

The primer is selected, or adapted, to be substantially complementary to a part of DNA which is adjacent to the region of at least one of the aforementioned mutations. Thus such a primer is able is hybridize with a part of DNA that contains a region in which the mutation of interest may be found. Although the primer may not reflect the exact sequence of the region in which the mutation is thought to occur, the more closely the primer is to this sequence, then the better the binding will be. Ideally, the more closely the sequence of the 3' end of the primer is to said region the better the binding or interaction will be.

An alternative method for using the sequence unique to a variant for detection relates to use of an oligonucleotide probe for specifically detecting the presence or absence of a CYP2 variant gene in a sample. this method comprises the steps of contacting the sample with a nucleic acid probe, allowing hybridization, forming a probe: CYP2 variant complex; washing excess probe from probe: CYP2 variant complex; and detecting probe: CYP2 variant complex, wherein a positive signal is an indication of the presence of the CYP2 variant in the sample.

The hybridization of the probe to sample nucleic acids can be carried out by any of the methods commonly used in the art. Such methods include but are not limited to, Dot blot, Colony hybridization, Southern blot, solution hybridization and in situ hybridization.

Washing the excess probe from the probe: CYP2 variant DNA can be accomplished by many well-known methods. Simply rinsing the complex with excess buffer will facilitate removal of excess probe. Alternatively, washing may entail separating the probe: CYP2 variant complex from excess probe. Many methods are known to one skilled in the art and include but are not limited to centrifugation, filtration and magnetic force.

According to the present invention there is provided a portion of DNA suitable for use as a primer in a method for identifying the presence or absence of a mutation either at codon 144 of the coding sequence of the gene CYP2C9, or alternatively, at least one gene conversion event involving CYP2A6 and CYP2A7 in exons 3, 6 or 8, or alternatively, at codon 160 of the coding sequence of the gene CYP2A6; comprising a DNA which is adapted to hybridize to at least one intron of at least one of said genes.

In one embodiment, the method comprises the use of at least one restriction endonuclease to digest DNA from individuals to be tested. In this instance, DNA from individuals positive for the wild-type form of CYP2C9 provide a digest with a restriction endonuclease, such as AvaII results in production of two fragments, a first fragment including 270 base pairs and a second fragment including 50 base pairs. In contrast, individuals having the aforementioned mutation in CYP2C9 present a single fragment of 320 base pairs only. This is due to a loss of the AvaII site. The CYP2A6 gene variants can also be distinguished by the occurrence of specific restriction endonuclease sites. The CYP2A6v1 variant, which is a $T_{488} \rightarrow A$ mutation in exon 3 can be identified by a variant-specific XcmI restriction site. The CYP2A6v2 variant, which contains a $C_{415} \rightarrow A$ mutation within exon 3 can be identified by a variant-specific DdeI restriction site. The wild-type CYP2A6 gene does not contain either an XcmI or DdeI site. The results of such restriction endonuclease digestions are illustrated in FIG. 9.

It may be necessary to amplify the DNA prior to digestion. Such may be the case when the DNA of interest is present in minute quantities in a sample. In such circumstances, amplification of DNA to be tested is undertaken before digesting the DNA as described above. This provides for a greater quantity of materials. Amplification is performed using any conventional technique, such as by a PCR reaction. Many other techniques for amplification can be used in producing sufficient DNA for detections. Such amplification techniques are well-known to the skilled artisan and include, but are not limited to polymerase chain reaction (PCR), PCR in situ, ligase amplification reaction (LAR), ligase hybridization, QB bacteriophage replicase, transcription-based amplification system (TAS), genomic amplification with transcript sequencing (GAWTS) and nucleic acid sequence-based amplification (NASBA). A general review of these methods is available in Landegren, et al., *Science* 242:229–237 (1988) and Lewis, R., *Genetic Engineering News* 10:1, 54–55 (1990), which is incorporated herein by reference.

One embodiment of the present invention uses oligonucleotide primers in an amplification and detection assay. A basic description of nucleic acid amplification is described in Mullis, U.S. Pat. No. 4,683,202, which is incorporated herein by reference. The amplification reaction uses a template nucleic acid contained in a sample, two primer sequences and inducing agents. The extension product of one primer when hybridized to the second primer becomes a template for the production of a complementary extension product and vice versa, and the process is repeated as often as is necessary to produce a detectable amount of the sequence.

The inducing agent may be any compound or system which will function to accomplish the synthesis of primer extension products, including enzymes. Suitable enzymes for this purpose include, for example, E.coli lDNA polymerase I, thermostable Taq DNA polymerase, Klenow fragment of E.coli DNA polymerase I, T4 DNA polymerase, other available DNA polymerases, reverse transcriptase and other enzymes which will facilitate combination of the nucleotides in the proper manner to form amplification products.

A sample being screened for the presence or absence of a mutation in CYP2A6 and/or CYP2C9 genes can be tested with the instant invention. The nucleic acid material can be in purified or nonpurified form, provided the sample contains the CYP2A6 and/or CYP2C9 genes. The sample may be derived from any tissue or bodily fluid, wherein the patient's DNA can be found. A clinically practical type of sample is a blood specimen which contains patient DNA and can conveniently be genotyped in the bioassay of the present invention.

The "primers", as the term is used in the present invention refers to an oligonucleotide, whether occurring naturally as in a purified restriction digest or produced synthetically, which is capable of acting as a point of initiation of synthesis when placed under conditions wherein synthesis of a primer extension product which is complementary to a nucleic acid strand is induced, i.e. in the presence of nucleotides and an inducing agent such as DNA polymerase and at a suitable temperature and pH. The primers are preferably single stranded for maximum efficiency in amplification, but may alternatively be double stranded. If double stranded, the primer is first treated to separate its strands before being used to prepare amplification products. Preferably, the primers are oligodeoxyribonucleotides. The primers must be sufficiently long to prime the synthesis of extension products in the presence of the inducing agent. The exact lengths of the primers will depend on many factors, including temperature, source of primer and use of the method. For diagnostic methods, the primers typically contain at least 10 or more nucleotides. The oligonucleotide primers may be prepared using any suitable method, such as, for example, the phosphotriester and phosphodiester methods (Narang, S. A., et al., Meth. Enzymol. 68:90 (1979); Brown E. L., et al., Meth. Enzymol., 68:109 (1979)) or automated embodiments thereof. In one such automated embodiment diethylphosphoramidites are used as starting materials and may be synthesized as described by Beaucage et al., Tetrahedron Letters 22:1859–1962 (1981). One method for synthesizing oligonucleotides on a modified solid support is described in U.S. Pat. No. 4,458,066. It is also possible to use a primer which has been isolated from a biological source (such as a restriction endonuclease digest).

In a genotyping bioassay of the present invention, one embodiment comprises a gene-specific amplification reaction, an exon-specific amplification reaction and a restriction endonuclease reaction. In such a reaction a suitable polynucleotide polymerase is used in the amplification reaction, many of which have already been described in the art. In addition, any appropriate restriction endonuclease which is designed to digest the DNA and so provide information concerning genotype may be used.

It may further be necessary to provide a label on the nucleic acid for detection. The nucleic acid can be DNA or RNA and made detectable by any of the many labeling techniques readily available and known to the skilled artisan. Such methods include, but are not limited to, radiolabelling, digoxygenin-labeling, and biotin-labeling. A well-known method of labeling DNA is $^{32}$P using DNA polymerase, Klenow enzyme or polynucleotide kinase. In addition, there are known non-radioactive techniques for signal amplification including methods for attaching chemical moieties to pyrimidine and purine rings (Dale, R. N. K. et al. 1973 Proc. Natl. Acad. Sci. USA, 70:2238–2242; Heck, R. F. 1968 S. Am. Chem. Soc., 90:5518–5523), methods which allow detection by chemiluminescence (Barton, S. K. et al. 1992 J. Am. Chem. Soc., 114:8736–8740) and methods utilizing biotinylated nucleic acid probes (Johnson, T. K. et al. 1983 Anal. Biochem., 133:125–131; Erickson, P. F. et al. 1982 J. of Immunology Methods, 51:241–249; Matthaei, F. S. et al 1986 Anal. Biochem., 157:123–128) and methods which allow detection by fluorescence using commercially available products. Non-radioactive labelling kits are also commercially available. Such a label can readily be incorporated into the nucleic acid during an amplification step. In the absence of an amplification step, a target nucleic acid can readily be chemically or enzymatically modified to carry a label. Additionally, it may be preferable to provide a labeled primer which may serve to incorporate a label into the nucleic acid target. Probes, as may be used in an embodiment of the invention may also be chemically or enzymatically labeled as described above.

In a preferred embodiment of the invention said DNA primer hybridizes to an intron adjacent said position of said mutation. Preferably said DNA is a primer with the 3'-end specific for the gene of interest. Preferably further still said DNA is single stranded. Preferably further still, in so far as the CYP2C9 mutation is concerned, said primers are as follows:

HF18: position 8 of intron 2 onwards of genomic sequence in forward orientation comprises 5' TGCAAGTGCCTGTTTCAGCA 3' (SEQ ID NO: 5)

HF2R: position 505 onwards of cDNA sequence in reverse orientation comprises 5' AGCCTTG-GTTTTTCTCAACTC 3' (SEQ ID NO: 6).

It is of note that both these primers are designed to be specific for CYP2C9 and so do not amplify related genes such as CYP2C8, which notably also has an Arginine$_{144}$ present.

Preferably, in so far as CYP2A6 is concerned, three primers J51, J61 and B are used in two parallel allele-specific PCR reactions. These primers are as follows:

J51 comprises 5' GGCTTCCTCATCGACGCACT 3' (SEQ ID NO: 7) (forward strand from position 479 of cDNA sequence described as hIIA3 (Yamano, et al. 1990 Biochem 29:1322–29)).

J61 comprises 5' GGCTTCCTCATCGACGCACA 3' (SEQ ID NO: 8) (forward strand from position 479 of CDNA sequence described as hIIA3v (Yamano, et al. 1990 Biochem 29:1322–29)).

Both J51 and J61 contain a substitution at position 18 of A for C to give improved specificity as suggested by Newton et al (1989 Nuc. Acids Res. 17:2503–2516).

Primer B comprises 5' AATTCCAGGAGGCAGGGCCT 3' (SEQ ID NO: 9) (reverse orientation from position 125 of intron 3 of CYP2A6 (onwards). Designed so that only CYP2A6 and not CYP2A7 or CYP2A12 are amplified.

One method of genotyping CYP2A6 provides an allele-specific amplification reaction method is used. In this instance, DNA which is adapted to specifically hybridize to the wild-type or the mutant type of the gene is incubated with test DNA under reaction conditions and the resultant products are analyzed by electrophoresis and then visualized by staining with ethidium bromide. Individuals who are homozygous for the wild-type allele produce a reaction product with primer J51 only. Similarly, individuals who are homozygous for the mutation produce a reaction product with primer J61 only. Those individuals who are heterozygous produce a reaction product with both J51 and J61.

Alternatively, another method for genotyping CYP2A6 is provided in a specific amplification bioassay, which is achieved with primers F4 and R4 as follows:

The F4 primer (forward) comprises
5' CCCCTTATCCTCCCTTGCTGGCTGTGTC-CCAAGCTAGGCAGGATT CATGGTGGGCA 3' (SEQ ID NO: 10), wherein a preferred fragment thereof further comprises

5' CCTCCCTTGCTGGCTGTGTCCCAAGCTAGGC 3' (SEQ ID NO: 11).

The R4 primer (reverse) comprises
5' GCCACCACGCCCCTTCCTTTCCGCCATC-CTGCCCCAGTCTTAGC TGCGCCCTCTC 3' (SEQ ID NO: 12), wherein a preferred fragment thereof further comprises

5' CGCCCCTTCCTTTCCGCCATCCTGCCCCAG 3' (SEQ ID NO: 13).

This method of CYP2A6 genotyping involves a first amplification reaction with F4 and R4 primers, which generates a DNA fragment approximately 7.8 kb in size. This amplification step is facilitated by polymerases which are capable of transcribing long stretches of DNA. To distinguish the CYP26Av1 and CYP26Av2 variant alleles, an exon-specific amplification step is carried out using the 7.8 Kb DNA fragment as template DNA. This may be accomplished using the following primer pair:

The E3F primer (forward) comprises
5' CCTGATCGACTAGGCGTGGTATTCAG-CAACGGGGAGCGCGCCAAG CAGCTCCTG 3' (SEQ ID NO: 14), wherein a preferred fragment thereof further comprises

5' GCGTGGTATTCAGCAACGGG 3' (SEQ ID NO: 15).

The E3R primer (reverse) comprises
5' CGCGCGGGTTCCTCGTCCTGGGT-GTTTTCCTTCTCCTGCCCCGC ACTCGGGAT-GCG 3' (SEQ ID NO: 16), wherein a preferred fragment thereof further comprises

5' TCGTCCTGGGTGTTTTCCTTC 3' (SEQ ID NO: 17).

Using these primers in a second amplification reaction step a segment of CYP2A6 exon 3 is specifically amplified. The method further comprises use of the restriction endonuclease XcmI to detect the CYP2A6v1 mutation and DdeI to detect the CYP2A6v2 mutation.

According to a yet further aspect of the invention there is provided a kit for performing the afore described methods which kit includes at least a portion of DNA in accordance with the invention and preferably at least one control sample of DNA containing the mutation or mutations of interest and ideally also a wild-type sample of DNA so that suitable comparisons can be made.

It is of note that although the method is described with reference to the above methods, any suitable method using the genetic material of the invention may be used to identify the mutations described herein.

The CYP2C9 assay has been used in a study of warfarin dose requirement in 94 patients undergoing anticoagulant treatment and the results obtained are summarized in FIG. 5. 58 patients (61.7%) were homozygous for the wild-type ($Arg_{144}$) allele and were found to require a median weekly maintenance dose of 31.5 mg of warfarin. 36 patients (38.6%) were heterozygous and required a median weekly maintenance dose of 24.5 mg. The doses required by the two groups were significantly different (Mann-Whitney U-test, p=0.016). No subjects in the group were homozygous for the mutant allele but based on allele frequencies and the Hardy Weinberg equilibrium, the predicted frequency of homozygous mutant subjects is 3.7%.

Comparison of the weekly maintenance dose of warfarin in the R144C heterozygotes (n=36) and homozygous wild-type (n=58) reveals that the heterozygotes required a significantly lower dose (range of 10.5–80.mg). Moreover, of the patients requiring the lowest doses to maintain an anticoagulation target (INR 2.0–4.0), in the range 5–15 mg per week, 9 out of 10 were heterozygous. At the other extreme of weekly doses>55 mg, 5 out of 6 patients were homozygous wild-type for CYP2C9. The significantly lower (20%) warfarin dose requirement of the patients with one variant R144C allele is consistent with the kinetic properties of the R144C protein with respect to (S)-warfarin hydroxylation and presumed in vivo metabolic clearance (Rettie et al. 1994 *Pharmocogen.*, 4:39–42).

The CYP2A6 genotyping assay has been used in studies on coumarin metabolism. Coumarin 7-hydroxylase activity is a convenient marker activity to identify the presence of CYP2A6 in a particular sample. There is considerable variation in the ability of individuals to 7-hydroxylate this compound which is a reaction specific for CYP2A6. A subject deficient in coumarin 7-hydroxylation has been identified. This subject is homozygous for the mutant CYP2A6v1 allele confirming the previous in vitro findings that substitution of Leu160 by His results in loss of coumarin 7-hydroxylase activity. As shown in FIG. 6, CYP2A6 genotyping and phenotyping with coumarin has been performed on other members of the proband's family and impaired coumarin 7-hydroxylation has been observed in heterozygotes for the CYP2A6v1 mutation.

The genotyping assays described herein resulted from a two step amplification reaction wherein first amplification reaction amplifies a 7.8 Kb fragment containing the CYP2A6 gene (FIG. 9A) and a second amplification reaction amplifies an exon-specific fragment of CYP2A6. The amplification product was digested with restriction endonucleases producing different patterns for the various CYP2A6 alleles. Representative results obtained for several human subjects for the detection of the CYP2A6v1 (XcmI digestion) and CYP2A6v2 (DdeI digestion) are shown in FIG. 9 panel B. A schematic depiction of this genotyping assay is shown in FIG. 9, panel C. Of 155 human genomic DNA samples analyzed 21 heterozygous (+/−) and 6 homozygous (−/−) subjects were detected for the CYP2A6v1 allele, whereas 17 heterozygous (+/−) and no homozygous were identified for the CYP2A6v2 allele variant. Additionally, 7 homozygous for both CPYP2A6v1 and CYP2A6v2 alleles were found.

Allelic frequencies were calculated for either allele in several ethic groups and analyzed as shown in Table 1. CYP2A6v1 frequency is almost identical between Caucasian and Japanese, and it is only twice the frequency in Taiwanese samples. Significantly, this allele is completely absent in the African-American population within the samples studied. The Japanese population has a remarkable higher frequency for the CYP2A6v2 allele (28%) as compared to the Caucasian (2%), Taiwanese (6%) or African- American (2.5%) (ethnic groups).

TABLE 1

Allelic frequency for the CYP2A6 gene in different ethnic groups.

| Ethnic Group | CYP2A6 | Allelic Frequencies (%) CYP2A6v1 | CYP2A6v2 | N |
|---|---|---|---|---|
| Caucasian | 75 | 23 | 2 | 52 |
| Japanese | 52 | 20 | 28 | 40 |
| Taiwanese | 83 | 11 | 6 | 178 |
| African-American | 97.5 | 0 | 2.5 | 40 |

The following examples illustrate various aspects of the present invention and in no way are intended to limit the scope thereof. All books, articles, and patents referenced herein are incorporated herein, in toto, by reference. Other similar embodiments will be clear to the skilled artisan and are encompassed within the spirit and purview of the present invention.

EXAMPLE 1
Method for determining the genotype CYP2C9

Genotyping for the CYP2C9 polymorphism is carried out by amplification by PCR followed by digestion with the restriction endonuclease AvaII. Amplifications are performed in 0.5 ml microcentrifuge tubes in a volume of 100 μl containing 10 mM Tris-HCl, pH 8.8, 1.5 mM MgCl2. 50 mM KCl, 0.1% Triton X-100, 5% dimethylsulphoxide, 200 μM each of dTTP, dATP, dCTP and dGTP, 250 μM of the primers HF18 and HF2R, 2.5 units Taq polymerase and 1 μg human leukocyte genomic DNA. PCR conditions consist of 35 cycles with a denaturation at 93° C. for 1 min. annealing at 55° C. for 1.5 min and polymerization at 72° C. for 1 min. 20 μl of the amplified DNA is incubated with 10 units AvaII for 3 h at 37° C. and then analyzed by electrophoresis on 1.8% agarose minigels in TBE (90 mM Tris-borate, 2 mM EDTA) buffer. The digestion products are visualized by ethidium bromide staining. DNA from individuals positive for the wild-type Arg,44 is digested to give fragments of 270 bp and 50 bp whereas in individuals with the mutant $Cys_{144}$ present, a band of 320 bp is seen due to loss of an AvaII site (FIG. 3).

EXAMPLE 2
Genotyping for the CYP2C9 polymorphism was carried out by amplification by PCR followed by digestion with the restriction endonuclease AvaII.

One hundred patients were recruited from two anticoagulation clinics in the Newcastle area over four study days. Body weight and height were measured, the basal metabolic index ("BMI") calculated for each patient and details of age, sex, drug history, current and previous International Normalized Ratio ("INR") determinations, indications for anticoagulation and other significant health problems were all recorded. DNA was isolated by a standard manual chloroform-phenol extraction procedure and 1 μg was subjected to PCR analysis. As shown in FIG. 10 the C→T substitution, which converts Arg→144 to Cys, resides in exon 3 of the CYP2C9 gene and results in the loss of an AvaII restriction site ( . . . GA<u>GGACC</u>GTGTTCAA . . . ) in the R144C allele ( . . . GAGGAC<u>T</u>GTGTTCAA . . . ). This provided the basis of the amplification strategy. A CYP2C9 specific intron forward primer (HF18, TGCAAGTGCCTGTTTCAGCA, FIG. 10) and a CYP2C9 exon 3 3'-end reverse primer (HF2R, AGCCTTGGTTTTTCTCAACTC, FIG. 10) were used at a concentration of 250 μM each. Amplifications were performed in a volume of 100 μl containing 20 mM Tris HCl (pH 8.3), 1.5 mM $MgCl_2$, 25 mM KCl, 0.05% (w/v) Tween 20, 10 μg gelatin/ml, 2% (w/v) DMSO, 200 μM each of dATP, dCTP, dGTP and dTTP and 2.5 units of Taq DNA polymerase (Perkin-Elmer). Reactions were carried out for 35 cycles at an annealing temperature of 55° C. for 90 sec, a polymerase temperature of 72° C. for 1 min, and a heat denaturing temperature of 93° C. for 1 min, using a Perkin-Elmer Cetus DNA thermal cycler. The PCR products digested with AvaII and sized using NuSieve agarose gels (3% NuSieve, 0.75% agarose). Presence of the CYP2C9 wild-type and R144C alleles were detected as fragments of 50+270 bp and 320 bp respectively (see FIGS. 3). The PCR product synthesized from human genomic DNA with the primers HF18/HF2R was directly sequenced on an ABI 373A automatic sequencer. Briefly, the PCR product was first purified by using the Wizard DNA clean-up system (Promega Co., Madison, Wis.). The purified template was then subjected to dideoxy terminator cycle-sequencing with the primers HF18 and HF2R. The primer-extended products were purified and sequenced following the manufacturer's procedure. Sequence analysis was done by using the MacVector software program (Eastman-Kodak Co., Rochester, N.Y.).

DNA was obtained from 94 patients. Of these 58 (62%) were homozygous for the wild-type CYP2C9 gene and 36 (38%) were heterozygous for the R144C allele. No R144C homozygotes were found. The frequency of the wild-type (Arg-144) and R144C (Cys-144) alleles in the study population is thus 0.808 and 0.192 respectively. An expectation of 3.7% R144C homozygotes can be anticipated from the Hardy-Weinberg equilibrium, but the 95% confidence interval in this estimation of 0.8–8.4% and thus the finding of zero homozygotes in 94 patients is not significantly different from expectation. The specificity of the PCR reaction with respect to the CYP2C9 gene was confirmed by sequencing. The alignment of the sequence obtained from the PCR product with that corresponding to the CYP2C9 gene showed a 100% degree of homology. Interestingly, a heterozygous pattern was obtained for the R144C allelic variant, confirming the high frequency of this allele within the normal population. No sequence deriving from CYP2C9, CYP2C18 or CYP2C19 was found confirming the specificity of the assay for CYP2C9.

EXAMPLE 3
Method for determining the genotype CYP2A6

Genotyping for the CYP2A6 polymorphism is carried out by allele-specific PCR using two parallel PCR reactions, one specific for the wild-type allele, one for the mutant allele. Amplifications are performed in 0.5 ml microcentrifuge tubes in a volume of 45 μl containing 10 mM Tris-HCl, pH 8.8, 1.5 mM $MgCl_2$, 50 mM KCl, 0.1% Triton X-100, 5% dimethylsulfoxide, 200 μM each of dTTP, DATP, dCTP and dGTP, 250 μM of the primers B and either J51 or J61, 1.25 units Taq polymerase and 1 μg human leukocyte genomic DNA. PCR conditions consist of 40 cycles with a denaturation at 93° C. for 1 min., annealing at 57° C. for 2 min and polymerization at 70° C. for 2 min. The products are analyzed by electrophoresis on 1% agarose minigels in TBE buffer and DNA is visualized by staining with ethidium bromide. As shown in FIG. 4, there are three possible results: the individual may be homozygous for the wild-type allele and give a DNA product only for the PCR reaction with primer J51, the individual may be heterozygous with one wild-type and one mutant allele and give DNA products with both primers J51 and J61 or the individual may be homozygous for the mutation and give a DNA product only with the J61 primer.

EXAMPLE 4
Alternative Method for Determining the Genotype CYP2A6

For use of F4 and R4 primers, each reaction mixture contained 600 ng human genomic DNA, 0.2 μM of each primer, 200 μM dNTP's, 0.8 mM magnesium acetate and 2 units of rTth I DNA polymerase. Hot start was as indicated by the manufacturer (Perkin Elmer) and the amplification reaction of 31 cycles of 93° C., 1 min; 66° C., 6 min 30 sec. Amplification products were analyzed in 0.7% agarose gels and the DNA visualized by staining with ethidium bromide. For the exon 3 specific amplification, the reaction which uses, the primers E3F and E3R consist of 5 μl of the 7.8 Kb PCR reaction, 0.5 82 M of each primer, 200 μM dNTP's, 1.5 μM MgCl$_2$ and 2.5 units of Taq DNA polymerase. The amplification reaction consisted of 94° C. for 3 minutes followed by 31 cycles of 94° C., 1 minute; 60° C., 1 minute and 72° C., 1 minute.

Amplification products were then digested without purification with restriction endonucleases which detect the CYP2A6 wild type (no digestion), CYP2A6v1 (XcmI) and CYP2A6v2 (DdeI). DNA was visualized by use of ethidium bromide after electrophoresis in 1% agarose, 3% NuSieve agarose.

It is of note that CYP2C9 genotyping can be performed using an allele-specific assay similar to that used above for CYP2A6.

---

We claim:

1. A CYP2A6v2 DNA having a coding sequence shown in FIG. 9 (SEQ ID NO: 1).

2. The DNA of claim 1 having a genomic sequence as shown in FIG. 10 (SEQ ID NO: 2).

3. A CYP2A13 DNA having a coding sequence shown in FIG. 11 (SEQ ID NO: 3).

4. The DNA of claim 3 having a genomic sequence shown in FIG. 12 (SEQ ID NO: 4).

5. A nucleic acid primer sequence comprising at least ten (10) contiguous nucleotide bases selected from the sequence shown in FIG. 10 (SEQ ID NO: 3).

6. A nucleic acid primer sequence comprising at least ten (10) contiguous nucleotide bases selected from the sequence shown in FIG. 12 (SEQ ID NO: 4).

7. A nucleic acid primer sequence selected from the group consisting of:

5' GGCTTCCTCATCGACGCACT 3' (SEQ ID NO: 7);

5' GGCTTCCTCATCGACGCACA 3' (SEQ ID NO: 8);

5' AATTCCAGGAGGCAGGGCCT 3' (SEQ ID NO: 9);

5' TGCAAGTGCCTGTTTCAGCA 3' (SEQ ID NO: 5);

5' AGCCTTGGTTTTTCTCAACTC 3' (SEQ ID NO: 6);

5' CCCCTTATCCTCCCTTGCTGGCTGTGTC-CCAAGCTAGGCA GGATTCATGGTGGGGCA 3' (SEQ ID NO: 10);

5' GCCACCACGCCCCTTCCTTTCCGCCATC-CTGCCCCCAGTC TTAGCTGCGCCCCTCTC 3' (SEQ ID NO: 12);

5' CCTGATCGACTAGGCGTGGTATTCAG-CAACGGGGAGCGCG CCAAGCAGCTCCTG 3' (SEQ ID NO: 14);

5' CGCGCGGGTTCCTCGTCCTGGGT-GTTTTCCTTCTCCTGCC CCCGCACTCGGGAT-GCG 3' (SEQ ID NO: 16);

or a fragment of said nucleic acid sequences of at least contiguous nucleotides.

8. A method of determining the presence or absence of an allelic variant in CYP2A6 or CYP2C9 DNA by using the primers recited in claims 5 or 6 or 7 comprising:

(a) amplifying an exon containing a variant sequence with in said DNA, producing an extension product;

(b) treating extension products with at least one restriction endonuclease under conditions sufficient to produce digestion fragments;

(c) analyzing the digestion fragments, for a variant specific digestion fragment or lack thereof.

9. The method of claim 8 wherein a CYP2C9 variant DNA is being detected.

10. The method of claim 9 wherein the amplifying step is a polymerase chain reaction using primers comprising HF18 (SEQ ID NO: 5) and HF2R (SEQ ID NO: 6).

11. The method of claim 8 wherein step (a) is preceded by a gene-specific amplification reaction.

12. The method of claim 11 wherein the gene-specific amplification is a polymerase chain reaction.

13. The method of claim 12 wherein a CYP2A6 variant is being detected.

14. The method of claim 13 wherein a gene-specific amplification reaction uses primers comprising F4 (SEQ ID NO: 10) and R4 (SEQ ID NO: 14) and the exon amplification reaction uses primers comprising E3F (SEQ ID NO: 14) and E3R (SEQ ID NO: 16).

15. The method according to claim 10 wherein the extension products are treated with the restriction endonuclease AvaII.

16. The method according to claim 14 wherein the extension products are treated with at least one restriction endonuclease comprising DdeI and XcmI.

17. A method of determining the presence or absence of an allelic variant in CYP2A6 or CYP2C9 DNA by using the primers recited in claims 5 or 6 or 7 comprising:

(a) contacting said DNA with a first primer encompassing a nucleotide variation specific to variant DNA and a second primer which is complementary to a region of said DNA such that upon hybridization and amplification, an extension product will be formed;

(b) analyzing the extension products for allelic-variant specific extension products.

18. The method of claim 17 wherein a CYP2A6 variant DNA is being detected.

19. The method of claim 18 wherein the amplifying step is a polymerase chain reaction wherein the first primer comprises J51 (SEQ ID NO: 7) and J61 (SEQ ID NO: 8) and the second primer comprises primer B (SEQ ID NO: 9).

20. A kit for determining the presence or absence of an allelic variant of CYP2A6 or CYP2C9 DNA comprising: at least one nucleic acid primer sequence capable of hybridizing to said DNA selected from teh group consisiting of the primer Seq. I.D. Nos. 3–10, 12, 14, and 16; the kit further containing instructions relating to the determination of the presence or absence of an allelic variant of CYP2A6 or CYP2C9 DNA.

21. The kit according to claim 20 further comprising amplification components and at least one restriction endonuclease.

22. The kit of claim 20 wherein the CYP2A6 allelic variant is being detected.

23. The kit of claim 22 wherein the nucleic acid primers comprise F4 (SEQ ID NO: 10), R4 (SEQ ID NO: 12), E3F (SEQ ID NO: 14) and E3R (SEQ ID NO: 16).

24. The kit according to claim 20 wherein the CYP2C9 allelic variant is being detected.

25. The kit according to claim 24 wherein the nucleic acid primers comprise HF18 (SEQ ID NO: 5) and HF2R (SEQ ID NO: 6).

* * * * *

SEQUENCE LISTING ( 1 ) GENERAL INFORMATION:

( i i i ) NUMBER OF SEQUENCES:17

( 2 ) INFORMATION FOR SEQ ID NO:1:

( i ) SEQUENCE CHARACTERISTICS:
        ( A ) LENGTH: 1740 base pairs
        ( B ) TYPE: nucleic acid
        ( C ) STRANDEDNESS: double
        ( D ) TOPOLOGY: linear ( i x ) FEATURE:
        ( A ) NAME/KEY: CYP2A6v2
        ( B ) LOCATION:
        ( D ) OTHER INFORMATION:

( x i ) SEQUENCE DESCRIPTION: SEQ ID NO:1:

```
ATGCTGGCCT  CAGGGATGCT  TCTGGTGGCC  TTGCTGGCCT                40
GCCTGACTGT  GATGGTCTTG  ATGTCTGTTT  GGCAGCAGAG                80
GAAGAGCAAG  GGGAAGCTGC  CTCCGGGACC  CACCCCATTG               120
CCCTTCATTG  GAAACTACCT  GCAGCTGAAC  ACAGAGCAGA               160
TGTACAACTC  CCTCATGAAG  ATCAGTGAGC  GCTATGGCCC               200
CGTGTTCACC  ATTCACTTGG  GGCCCCGGCG  GGTCGTGGTG               240
CTGTGTGGAC  ATGATGCCGT  CAGGGAGGCT  CTGGTGGACC               280
AGGCTGAGGA  GTTCAGCGGG  CGAGGCGAGC  AAGCCACCTT               320
CGACTGGGTC  TTCAAAGGCT  ATGGCGTGGT  ATTCAGCAAC               360
GGGGAGCGCG  CCAAGCAGCT  CCTGCGCTTT  GCCATCGCCA               400
CCCTGAGGGA  CTTCGGGGTG  GGCAAGCGAG  GCATCGAGGA               440
GCGCATCCAG  GAGGAGTCGG  GCTTCCTCAT  CGAGGCCATC               480
CGGAGCACGC  ACGGCGCCAA  TATCGATCCC  ACCTTCTTCC               520
TGAGCCGCAC  AGTCTCCAAT  GTCATCAGCT  CCATTGTCTT               560
TGGGGACCGC  TTTGACTATA  AGGACAAAGA  GTTCCTGTCA               600
CTGTTGCGCA  TGATGCTAGG  AATCTTCCAG  TTCACGTCAA               640
CCTCCACGGG  GCAGCTCTAT  GAGATGTTCT  CTTCGGTGAT               680
GAAACACCTG  CCAGGACCAC  AGCAACAGGC  CTTTCAGTTG               720
CTGCAAGGGC  TGGAGGACTT  CATAGCCAAG  AAGGTGGAGC               760
```

```
ACAACCAGCG  CACGCTGGAT  CCCAATTCCC  CACGGGACTT                              800

CATTGACTCC  TTTCTCATCC  GCATGCAGGA  GGAGGAGAAG                              840

AACCCCAACA  CGGAGTTCTA  CTTGAAGAAC  CTGATGATGA                              880

GCACGTTGAA  CCTCTTCATT  GCAGGCACCG  AGACGGTCAG                              920

CACCACCCTG  CACTATGGCT  TCTTGCTGCT  CATGAAGCAC                              960

CCAGAGGTGG  AGGCCAAGGT  CCATGAGGAG  ATTGACAGAG                             1000

TGATCGGCAA  GAACCGGCAG  CCCAAGTTTG  AGGACGGGC                              1040

CAAGATGCCC  TACATGGAGG  CAGTGATCCA  CGAGATCCAA                             1080

AGATTTGGAG  ACGTGATCCC  CATGAGTTTG  GCCCGCAGAG                             1120

TCAAAAAGGA  CACCAAGTTT  CGGGATTTCT  TCCTCCCTAA                             1160

GGGCATAGAA  GTGTTCCCTA  TGTTGGGCTC  CGTGCTGAGA                             1200

GACCTCAGGT  TCTTCTCCAA  CCCCCGGGAC  TTCAATCCCC                             1240

AGCACTTCCT  GGGTGAGAAG  GGGCAGTTTA  AGAAGCGTGA                             1280

TGCTTTTGTG  CCCTTCTCCA  TCAGAAAGCG  GAACTGTTTC                             1320

GGAGAAGGCC  TGGCCAGAAT  GGAGCTCTTT  CTCTTCTTCA                             1360

CCACCGTCAT  GCAGAACTTC  CGCCTCAAGT  CCTCCCAGTC                             1400

ACCTAAGGAC  ATTGACGTGT  CCCCCAAACA  CGTGGGCTTT                             1440

GCCACGATCC  CACGAAACTA  CACCATGAGC  TTCCTGCCCC                             1480

GCTGAGCGAG  GGCTGTGCCG  GTGAAGGTCT  GGTGGGCGGG                             1520

GCCAGGGAAA  GGGCAGGGCC  AAGACCGGGC  TTGGGAGAGG                             1560

GGCGCAGCTA  AGACTGGGGG  CAGGATGGCG  GAAAGGAAGG                             1600

GGCGTGGTGG  CTAGAGGGAA  GAGAAGAAAC  AGAAGCGGCT                             1640

CAGTTCACCT  TGATAAGGTG  CTTCCGAGCT  GGGATGAGAG                             1680

GAAGGAAACC  CTTACATTAT  GCTATGAAGA  GTAGTAATAA                             1720

TAGCAGCTCT  TATTTCCTGA                                                     1740
```

( 2 ) INFORMATION FOR SEQ ID NO:2:

( i ) SEQUENCE CHARACTERISTICS:
        ( A ) LENGTH: 1737 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CYP2A13
        ( B ) LOCATION:
        ( D ) OTHER INFORMATION:

( x i ) SEQUENCE DESCRIPTION: SEQ ID NO:2:

```
ATGCTGGCCT  CAGGGCTGCT  TCTGGTGACC  TTGCTGGCCT                               40

GCCTGACTGT  GATGGTCTTG  ATGTCAGTCT  GGCGGCAGAG                               80

GAAGAGCAGG  GGGAAGCTGC  CTCCGGGACC  CACCCCATTG                              120

CCCTTCATTG  GAAACTACCT  CCAGCTGAAC  ACAGAGCAGA                              160

TGTACAACTC  CCTCATGAAG  ATCAGTGAGC  GCTATGGCCC                              200

TGTGTTCACC  ATTCACTTGG  GGCCCCGGCG  GGTCGTGGTG                              240
```

| | | |
|---|---|---|
| CTGTGCGGAC ATGATGCCGT CAAGGAGGCT CTGGTGGACC | | 280 |
| AGGCTGAGGA GTTCAGCGGG CGAGGCGAGC AGGCCACCTT | | 320 |
| CGACTGGCTC TTCAAAGGCT ATGGCGTGGC GTTCAGCAAC | | 360 |
| GGGGAGCGCG CCAAGCAGCT CCGGCGCTTC TCCATCGCCA | | 400 |
| CCCTAAGGGG TTTTGGCGTG GGCAAGCGCG GCATCGAGGA | | 440 |
| ACGCATCCAG GAGGAGGCGG GCTTCCTCAT CGACGCCCTC | | 480 |
| CGGGGCACGC ACGGCGCCAA TATCGATCCC ACCTTCTTCC | | 520 |
| TGAGCCGCAC AGTCTCCAAT GTCATCAGCT CCATTGTCTT | | 560 |
| TGGGGACCGC TTTGACTATG AGGACAAAGA GTTCCTGTCA | | 600 |
| CTGTTGCGCA TGATGCTGGG AAGGTTCCAG TTCACGGGAA | | 640 |
| CCTCCACGGG GCAGCTCTAT GAGATGTTCT CTTCGGTGAT | | 680 |
| GAAACACCTG CCAGGACACA GCAACAGGCC TTTAAGGAGC | | 720 |
| TGCAAGGGCT GGAGGACTTC ATCGCCAAGA AGGTGGAGCA | | 760 |
| CAACCAGCGC ACGCTGGATC CCAATTCCCC ACGGGACTTC | | 800 |
| ATCGACTCCT TTCTCATCCG CATGCAGGAG GAGGAGAAGA | | 840 |
| ACCCCAACAC AGAGTTCTAC TTGAAGAACC TGGTGATGAC | | 880 |
| CACCCTGAAC CTCTTCTTTG CGGGCACTGA GACCGTGAGC | | 920 |
| ACCACCCTGC GCTACGGTTT CCTGCTGCTC ATGAAGCACC | | 960 |
| CAGAGGTGGA GGCCAAGGTC CATGAGGAGA TTGACAGAGT | | 1000 |
| GATCGGCAAG AACCGGCAGC CCAAGTTTGA GGACCGGGCC | | 1040 |
| AAGATGCCCT ACACAGAGGC AGTGATCCAC GAGATCCAAA | | 1080 |
| GATTTGGAGA CATGCTCCCC ATGGGTTTGG CCCACAGGGT | | 1120 |
| CAACAAGGAC ACCAAGTTTC GGGATTTCTT CCTCCCTAAG | | 1160 |
| GGCACTGAAG TGTTCCCTAT GCTGGGCTCC GAGCTGAGAG | | 1200 |
| ACCCCAGGTT CTTCTCCAAC CCCCAGGACT GCAGTCCCCA | | 1240 |
| GCACTTCCTG GATGAGAAGG GGCAGTTTAA GAAGAGTGAT | | 1280 |
| GCTTTTGTGC CCTTTTCCAT CGGAAAGCGG TACTGTTTTG | | 1320 |
| GAGAAGGCCT GGCCAGAATG GAGCTCTTTC TCTTCTTCAC | | 1360 |
| CACCATCATG CAGAACTTTC GCTTCAAGTC CCCTCAGTCG | | 1400 |
| CCTAAGGATA TCGACGTGTC CCCCAAACAC GTGGGCTTTG | | 1440 |
| CCACGATCCC ACGAAACTAC ACCATGAGCT TCCTGCCCCG | | 1480 |
| CTGAGCGAGG GCTGTGCTGG TGCAGGGCTG GTGGGCGGGG | | 1520 |
| CCAGGGAAAC GGCCGGGGCA GGGGCGGGGC TTGTGGGAGG | | 1560 |
| GGCGGGGCTA AGAATGGGGG CAGTGGGGGA AGGAAGGGGA | | 1600 |
| GAGGTGGTTA GAGGGAACAG AAGAAACAGA AGGGGCTCAG | | 1640 |
| TTCACCTTGA TGATGTCCTT CAGAGCTGTG ATGAGAGGAA | | 1680 |
| GGGAAACCTT ACAGTATGCT ACAAAGAGTA GTAATAATAG | | 1720 |
| CAGCTCTTAT CTCCTGA | | 1737 |

( 2 ) INFORMATION FOR SEQ ID NO:3:

( i ) SEQUENCE CHARACTERISTICS:
   ( A ) LENGTH: 7216 base pairs
   ( B ) TYPE: nucleic acid
   ( C ) STRANDEDNESS: double
   ( D ) TOPOLOGY: linear ( i i ) MOLECULE TYPE: genomic DNA ( i x ) FEATURE:
   ( A ) NAME/KEY: CYP2A6v2
   ( B ) LOCATION:
   ( D ) OTHER INFORMATION:

( x i ) SEQUENCE DESCRIPTION: SEQ ID NO:3:

| | | | | |
|---|---|---|---|---|
| AAGTTCCCCT | GAAATATGGC | TCTGGTCTTC | CTCCCCTTGC | 40 |
| CAATGAAGAA | GATGGCAGTG | GAGGTTCTAT | GGCAGCCATC | 80 |
| CTGGCCTCAC | TCTGAGGTTC | CAATGAGGAT | TCTGGGCATC | 120 |
| AAGAGACAGC | TCTGGGCAAA | GCTAAATCAA | GTCAGCCCT | 160 |
| GGACCCAGTG | CTGGGCTGCT | GGGCTTTCTG | GGAGAACGCC | 200 |
| GCTGGGCTTG | CTACACACTC | CTCCTCCCAG | AAACTCCACA | 240 |
| CCCACAGCCC | TGGGTCTTCC | TAGCCCCGAG | ACTTTCAAGT | 280 |
| CCATATGCCT | GGAATCCCCC | TTCCTGAGAC | CCTTAACCCT | 320 |
| GCATCCTCCA | CAACAGAAGA | CCCCTAAATG | CACAGCCACA | 360 |
| CTTTGTCTTA | CCCTAATAAA | ACCCAGACCT | TTGGATTCCT | 400 |
| CTCCCCTGGA | ACCCCCAGAT | CCGCACAACT | TTGGGGTGCA | 440 |
| TTCTCACTCT | CAGACCCCAA | ATCCAAAGCC | CAAGTGCTCC | 480 |
| CCTATGCAAA | TATTCCAAAC | TCCTCAGTTC | TACAGCTTAT | 520 |
| CTGTTGCCCC | CTCCTAAATC | CACAGCCCTG | CGGCACCCCT | 560 |
| CCTGAAGTAC | CACAGATTTA | GTCTGGAGGC | CCCCTCTCTG | 600 |
| TTCAGCTGCC | CTGGGGTCCC | CTTATCCTCC | CTTGCTGGCT | 640 |
| GTGTCCCAAG | CTAGGCAGGA | TTCATGGTGG | GGCATGTAGT | 680 |
| TGGGAGGTGA | AATGAGGTAA | TTATGTAATC | AGCCAAAGTC | 720 |
| CATCCCTCTT | TTTCAGGCAG | TATAAAGGCA | AACCACCCCA | 760 |
| GCCGTCACCA | TCTATCATCC | CTCTACCACC | ATGCTGGCCT | 800 |
| CAGGGATGCT | TCTGGTGGCC | TTGCTGGCCT | GCCTGACTGT | 840 |
| GATGGTCTTG | ATGTCTGTTT | GGCAGCAGAG | GAAGAGCAAG | 880 |
| GGGAAGCTGC | CTCCGGGACC | CACCCCATTG | CCCTTCATTG | 920 |
| GAAACTACCT | GCAGCTGAAC | ACAGAGCAGA | TGTACAACTC | 960 |
| CCTCATGAAG | GTGTCCCAAG | ACAGGAGAT | GGGTGTCTCG | 1000 |
| GGGTGGGGGC | TGCCTAGTTG | GCTGGGGCTT | TGTGGCAGGG | 1040 |
| GGTTGACCAG | TGTGGACCAG | AGTCTTAGGA | AATGGAGTTT | 1080 |
| TGGAGTTTCA | GCATCAGAAA | GACAGGATCT | TGGGATGTCC | 1120 |
| AGCTCCCTGA | CTGTGAGAAC | CTGGGTGCGA | AGCATCCCAG | 1160 |
| CACATGACAT | CTCGGTGCTG | GGCCCCATTC | AGAGTGGAGG | 1200 |
| GTTCTCCCTC | TAACCACTCC | CACCCACCTC | CATCAGATCA | 1240 |
| GTGAGCGCTA | TGGCCCCGTG | TTCACCATTC | ACTTGGGGCC | 1280 |
| CCGGCGGGTC | GTGGTGCTGT | GTGGACATGA | TGCCGTCAGG | 1320 |

```
GAGGCTCTGG  TGGACCAGGC  TGAGGAGTTC  AGCGGGCGAG                    1360

GCGAGCAAGC  CACCTTCGAC  TGGGTCTTCA  AAGGCTATGG                    1400

TGCCCAAGAG  GGGGAAGGTG  GGCAGGTGGA  CACGAAGGTC                    1440

TCAGTGTTCC  CAGCCTTCTC  CCTGACTCTC  CTGACAACTG                    1480

GAGGATAAGG  GAGAGTCCCC  AGTCTGGTCT  TCCCTCCCCA                    1520

TCTCCCTACA  TTGGGGCCTC  TCCATGTGTA  TCCCTCACCT                    1560

GTCTCCAGCG  GCCCTGTCCT  GATTCCTCCC  TGCCTCTCTC                    1600

TGCCCCACCT  CCTTATTCTC  TCTCACTGGA  GTCTCCTCTT                    1640

TCCCCTCTCT  CTCCATCTCT  AAGGACATCC  TGGGTTTCTG                    1680

TTTACCAGCC  CTGGGTCTCT  GTCTACATGA  GTCTTTGAGG                    1720

CCCTCTTAGC  TTCTGGGCTT  CTCTGGGTTT  CTCATCTCTC                    1760

CGGATCCCTT  TCTCAATTCT  TCCTCTGTCT  TAGGATGCCA                    1800

GGGTTATTCC  TACTTCCACA  TCTTCAGGCT  CCATCTCCTG                    1840

GTAACAGTCT  CTCTTCCTTC  CAGACCCTCT  CTGTTTCTAT                    1880

CTCAATATTA  AACTCTCTGC  TCCAGCTCAG  CTTAAGAATC                    1920

TCACACCAAG  AGAGGATGTC  CTCCACCCAG  ATCTCCCCAT                    1960

ATCTCACTAC  CCCACCCTCC  ATCCTCTGCC  TCCATCACTC                    2000

TCTTTCTCTC  CCCACTGCNC  CTGCGGACGC  GATCCAATGG                    2040

AGTGTGGAGC  TAATGCCGTG  AAGCTATGTG  CATCTCTCTG                    2080

TCTGGCCGTA  CCTGGGTAAT  AACCTGATCG  ACTAGGCGTG                    2120

GTATTCAGCA  ACGGGGAGCG  CGCCAAGCAG  CTCCTGCGCT                    2160

TTGCCATCGC  CACCCTGAGG  GACTTCGGGG  TGGGCAAGCG                    2200

AGGCATCGAG  GAGCGCATCC  AGGAGGAGTC  GGGCTTCCTC                    2240

ATCGAGGCCA  TCCGGAGCAC  GCACGGTGAG  CAGGGGACCC                    2280

CGAGTGCGGG  GGCAGGAGAA  GGAAAACACC  CAGGACGAGG                    2320

AACCCGCGCG  CGTTCTGCCT  GGGGATGGGG  ACTAGGTGGG                    2360

GAAAGGCGCC  CGCACTTCCA  GCCCTGGAGT  CTGGCGCTGG                    2400

GAATTTGGCT  CAACAAGGCC  CTGCCTCCTG  GAATTCTGAC                    2440

TCTCCTCAGA  CCTCTGAGTT  GACTCTCTCC  CCAACCCCCT                    2480

TCTCCCGACA  TACCCGGAGG  CGCCAATATC  GATCCCACCT                    2520

TCTTCCTGAG  CCGCACAGTC  TCCAATGTCA  TCAGCTCCAT                    2560

TGTCTTTGGG  GACCGCTTTG  ACTATAAGGA  CAAAGAGTTC                    2600

CTGTCACTGT  TGCGCATGAT  GCTAGGAATC  TTCCAGTTCA                    2640

CGTCAACCTC  CACGGGGCAG  GTAATGGTTG  CAGCCCGGCC                    2680

CGTGAAGGCC  CTTACCAAAA  CCGGCAAATT  GTTCCCTAC                     2720

CGGGGGAAGG  GGGCCCCAAA  TTCCCACCGC  CCCCCGGACA                    2760

GTGTCCCCTC  AAAATCAGTC  CCCGATTTGG  GCAAATTGGC                    2800

AGAGTGGAAC  CAGACCCGGG  TTGGTTGTCC  AATCCCCTGC                    2840

TCTCCAGGGA  CACCGGGATA  GCACAACAGA  TGCTCCCCAA                    2880

AACAGAGCCT  GCTGGCAGGA  TGCATACCCT  CAGCTCAGCT                    2920
```

```
CTCTCACCCT GGGCACGTGT TCCCATCCCC AACTTACCGG         2960
TAATTTCTAA CAGATGCTCC CTACCCAGGT CTTCTTGAAT         3000
ATTTTAACAC CCGGAAACCC TGGGTACCTA ACCTTCCCTG         3040
TAAACTTTAG AGATTAGTTC CTATCCGGCC CCTCTGAAAT         3080
ACCTAACCAC CGGAGACCAG ATGCCTTTAA CTCAGTTCCT         3120
TCCTTGCTAT GAAACAAATC CCATTCCCAT CAGCTCCTGC         3160
CCCGTGACAG CTGTCCTTCC CTTCCATCC TCTCTCTGCA          3200
ACCCCAGCTC TATGAGATGT TCTCTTCGGT GATGAAACAC         3240
CTGCCAGGAC CGCAGCAACA GGCCTTTCAG TTGCTGCAAG         3280
GGCTGGAGGA CTTCATAGCC AAGAAGGTGG AGCACAACCA         3320
GCGCACGCTG GATCCCAATT CCCCACGGGA CTTCATTGAC         3360
TCCTTTCTCA TCCGCATGCA GGAGGTACAC CCCAGCAGCC         3400
ACTGCGGGGA GATGCAAAGC CAGGCAGAGG GAAATCAGTC         3440
TGGGAGTGGG GCAGGCAGAT GACACAGGCC CATTCAAATT         3480
AACCCTCATC ATAATAATCC TCACAATTGG CTGGGTGCCG         3520
TGGCTAACAG CCTGTAATCC CAGCACTTTG GGAGGCCGAG         3560
GCAGGTGGAT CACCTGAGGT CAGGAGTTCG AGACCAGCCT         3600
GGCCAACATG GTCAAACCCC GTCTCTACTA AAAATCCAAA         3640
AATTAGTTGG GCATGGTGGC GCGAAGGGGG GCAGAGGTTG         3680
CAATGAGCCA AGATCACGGC ATTGCACTCC AGTCTGGGTG         3720
ACAGAATGAG GCCCTGTGTC AAAAAAAATT AATCACTTGT         3760
TTAAAAAGTA AGTGAGCCTG CATGGTCATG CGCATGTGCA         3800
GCTCCAGCTA CTCAGGAGGC TGAGGCTGGA GGATTGCTTG         3840
AGCTCAGGAG TTGGCGTCCG GCCTGTGCAA CTTAGCAAGA         3880
CCAAGTCAGT ATAAGAAAAA AAAAAACAA AAAAAAGCT           3920
GACAGCTAAG TTGATAATTG ACGGACAGAT GGTCAGCAAG         3960
GTAACGAAGG TGAGAAGGAA GAGCATTGGG GGCAACGCCA         4000
GGAGTCAGGG CAAGGGCTGG TTCCTAGAGC GAGTCTGGTA         4040
GGATCTAGGG CCCCTCTTCT CCACCCTGCG GTCTTGCCCC         4080
AAAGAGAGGT CGAGGGTGCT GGGATTGCGC TAGACTCGAG         4120
TCTGTGTAGA TCTTGGGGTC CCCTCTTGAC CCCCATTGGT         4160
CTGAACCTAA GAGTGGAAGA TCCATGGGGT GAACCCCTAG         4200
ATGGTGCCCT GAGGTCAAGC AGGAGTGAGG TTGTCCTAAA         4240
GCCCCCTCTC CCTTCAGGAG GAGAAGAACC CCAACACGGA         4280
GTTCTACTTG AAGAACCTGA TGATGAGCAC GTTGAACCTC         4320
TTCATTGCAG GCACCGAGAC GGTCAGCACC ACCCTGCACT         4360
ATGGCTTCTT ACTGCTCATG AAGCACCCAG AGGTGGAGGG         4400
TAAGGCTGGA GGGGACGGA AGTGGAGGGC CCAGACCCT           4440
CAAAATTCCC CTTCGACTGG TGCAATGTCC CCACCTGTCC         4480
CAGATCCCGG GACCCTGAGA CGTGACTTGC TGTCCAGAGA         4520
```

| | | | | |
|---|---|---|---|---|
| CAGGGCAACA | TTCAGCTGGT | AGGCATCAGC | TGAGTCTCAT | 4560 |
| TAGATATTAA | AATATTGAAA | ATGTCTGCAC | TGATTGGTCA | 4600 |
| GTCACTTCTG | TCCCAAGCCC | ACTGAGTGCC | CACTGCCCGT | 4640 |
| TCCACCGGGT | CATCCCCTAA | GTTCCTCCCT | GTGCCTCCCC | 4680 |
| TGTGATTCTG | GCACAACCTG | GTTAACAGGA | TCCTACTCCA | 4720 |
| ACAATGCGAA | TGGGTGATGT | CTGTTCTGTT | ATGAATGCTC | 4760 |
| TACTTCCGTC | TCATAGGCGG | AGGCATTTCA | TCCACCCCAT | 4800 |
| TTTGCCTATC | CGGACTATCA | TTTCCTGCTC | TGAGACCCCT | 4840 |
| AGATACCTAA | ACACATTCCC | CCTCCTCCCC | CAGCCAAGGT | 4880 |
| CCATGAGGAG | ATTGACAGAG | TGATCGGCAA | GAACCGGCAG | 4920 |
| CCCAAGTTTG | AGGACCGGGC | CAAGATGCCC | TACATGGAGG | 4960 |
| CAGTGATCCA | CGAGATCCAA | AGATTTGGAG | ACGTGATCCC | 5000 |
| CATGAGTTTG | GCCCGCAGAG | TCAAAAGGA | CACCAAGTTT | 5040 |
| CGGGATTTCT | TCCTCCCTAA | GGTGCTATCC | GCCCCACCC | 5080 |
| CCCAGACTAC | GGGGACTCCA | GCCCTCTCT | GTGTCCCAG | 5120 |
| CATCCCACCC | ACATTAGAAG | CTTTCTAGAC | CCTGTCCCAC | 5160 |
| TCCCTCAATC | AGTCAAAAAA | GACTTCCCCA | ACCACCACAT | 5200 |
| CCGTTCCACC | TTTCCACTTA | GACACTCCTG | AGTCCTGCAT | 5240 |
| CTCTCCAGAC | TCTTTGTGTC | AGGAGAATCA | AACACATGTT | 5280 |
| CCCAAACTTC | CTATCTTAAG | AAACAGAAGC | CCCCTTTCCA | 5320 |
| TTCGGCCTTT | TGTCATAGGG | ACAGAAATCT | CAGGTCCCCC | 5360 |
| AAACTCCTGC | CTAGAAGGAC | ATGGACCCCA | TGTCTCCCAA | 5400 |
| ACTTCCTGTT | TCAGAGATGT | GAACCTTCTA | TCCCCAAGG | 5440 |
| TCCTCCCTCA | GAGGTCCCCA | ATTCCCATGC | CTGCCACTTC | 5480 |
| CCCTCACCGG | GGCACCCTAG | TTCCCCCTCC | AGCCCTGTG | 5520 |
| TACTCTCAAC | AATCCCCCAA | CCCGCCTCAT | CACATACACC | 5560 |
| TTCCTCCTCC | CTCCCAGGGC | ATAGAAGTGT | TCCCTATGTT | 5600 |
| GGGCTCCGTG | CTGAGAGACC | TCAGGTTCTT | CTCCAACCCC | 5640 |
| CGGGACTTCA | ATCCCCAGCA | CTTCCTGGGT | GAGAAGGGGC | 5680 |
| AGTTTAAGAA | GCGTGATGCT | TTTGTGCCCT | TCTCCATCAG | 5720 |
| TAAGAGACCA | CTGTTTGGTG | CCAGGCTTAC | TACTCACACC | 5760 |
| AGCAGGGGCC | TCCCTTACCC | AGTTCCCCTC | TCTGCCGTGT | 5800 |
| AGCCTAGTAT | TTCCCCAGCT | TGGCAAGTTC | CTGTTAGCAA | 5840 |
| TCTACCGTCG | AGCCACCAGG | TGATACTCCC | TTAACTACCA | 5880 |
| AGCACCCAGT | ACCTGTGCCC | AGGCAAAAGG | AAAGGAAACA | 5920 |
| TCATACCCCT | TTCAGAGGCG | GGGGAAAACC | AAAGGCCAGA | 5960 |
| GAGAATCAGA | GATTTATTTC | CCTAGGGTCA | CACAGGAGAT | 6000 |
| TCTTCAGCAT | CCCTAAAAAG | GAGATGACGG | CACAGCAGGT | 6040 |
| CATATTTGGG | AGTTCTTATC | TGGGGGAAGG | GGGATCTTAA | 6080 |
| ACCTCCCATT | GTGGACACCT | GGCATCGATC | AACCCCATCT | 6120 |

-continued

| | | | | |
|---|---|---|---|---|
| TTTGGTCATC | TTTTGGGTCA | CTCAAGGAAA | CTGAGGTCAA | 6160 |
| GGAGGGTCAA | GAGGCTCCCT | CTTAAAGTCT | CTCAGGGCCA | 6200 |
| TATATTCCAC | CCTTCCTCCC | TGGGAGAGCC | GCAGCTGGAG | 6240 |
| GTCGGTACTG | GGGCGAGGCT | GCACTGAGAG | TGGGCTTCAC | 6280 |
| CTCCACCCCT | CCCGCCTCTC | CTCCTCAGGA | AAGCGGAACT | 6320 |
| GTTTCGGAGA | AGGCCTGGCC | AGAATGGAGC | TCTTTCTCTT | 6360 |
| CTTCACCACC | GTCATGCAGA | ACTTCCGCCT | CAAGTCCTCC | 6400 |
| CAGTCACCTA | AGGACATTGA | CGTGTCCCCC | AAACACGTGG | 6440 |
| GCTTTGCCAC | GATCCCACGA | AACTACACCA | TGAGCTTCCT | 6480 |
| GCCCCGCTGA | GCGAGGGCTG | TGCCGGTGAA | GGTCTGGTGG | 6520 |
| GCGGGGCCAG | GGAAAGGGCA | GGGCCAAGAC | CGGGCTTGGG | 6560 |
| AGAGGGGCGC | AGCTAAGACT | GGGGGCAGGA | TGGCGGAAAG | 6600 |
| GAAGGGGCGT | GGTGGCTAGA | GGGAAGAGAA | GAAACAGAAG | 6640 |
| CGGCTCAGTT | CACCTTGATA | AGGTGCTTCC | GAGCTGGGAT | 6680 |
| GAGAGGAAGG | AAACCCTTAC | ATTATGCTAT | GAAGAGTAGT | 6720 |
| AATAATAGCA | GCTCTTATTT | CCTGAGCACG | TACCCCGTG  | 6760 |
| TCACCTTTGT | TCAAAAACCA | TTGCACGCTC | ACCTAATTTG | 6800 |
| CCACAAAACC | CCCTTCGAAG | GGGCGTTCAT | GCCCATTTTA | 6840 |
| CACGTGACAA | AACTGAGGCT | TAGAAAGTTG | TCTCTGATGT | 6880 |
| CTCACAAAAC | ATAAGTGCCC | AGAAAATCTG | CGAACACAGA | 6920 |
| TCTGTGCCCA | TAGCCTTCTA | GACAGATTCT | TAAAAGCAC  | 6960 |
| CTATTCCTCA | CGCAAAACAG | TTTAGTATAG | AATCACATGG | 7000 |
| CCTGAACATC | CCTGTCCGGG | GGAGTTCCCC | AGAGACCTGG | 7040 |
| GGGGTGGTTG | CCCTGCCTTC | ACTGCACACA | TGCCCACACT | 7080 |
| CTCACCTACT | CAACATGCTG | TGACTACCCG | GGTGTAATCT | 7120 |
| GTGCTTGCTA | CCAGATAAGG | CCACTGTAGC | CCATTCAGAG | 7160 |
| TCAGCCCAGG | GACACAACGA | GACATGACTG | GACATACAGG | 7200 |
| GTCAGTCCAT | TAACAA | | | 7216 |

( 2 ) INFORMATION FOR SEQ ID NO:4:

( i ) SEQUENCE CHARACTERISTICS:
        ( A ) LENGTH: 8779 base pairs
        ( B ) TYPE: nucleic acid
        ( C ) STRANDEDNESS: double
        ( D ) TOPOLOGY: linear ( i i ) MOLECULE TYPE: genomic DNA ( i x ) FEATURE:
        ( A ) NAME/KEY: CYP2A13
        ( B ) LOCATION:
        ( D ) OTHER INFORMATION:

( x i ) SEQUENCE DESCRIPTION: SEQ ID NO:4:

| | | | | |
|---|---|---|---|---|
| TGGGTCCAAC | CAAAATCAAA | GTCAATTCCC | TGGGCCCAGT | 40 |
| GCTGGGCTGC | TGGGCTTTTC | TGGGAGCACC | TGCTGGGCTT | 80 |
| GCTACACACT | CCACCTCCCA | GAAACTCCAC | ACCCACAGCC | 120 |

```
CTGGGTCTTC  CTAGCCCCAA  GACTTTCAAG  TCCATATGCC            160
TGGAATCCCC  CGTCCTGAGA  CCCTTAACCC  TGCATCCTCC            200
ACAACAGAAG  ACCCCCAGAT  GCACAGCCAC  ACTTCCATCT            240
CACCCTAGTA  AAACCCAGAC  CTTTGGATTC  CTCTCCCGTG            280
GAATGCCCAA  ATCCACAACT  TTGGGGTGCA  GTCTCACTCC            320
CAGATCCCAA  ATCCAAAGAC  CAGGTGCTCC  CCTGTGCAAA            360
TATTCCAAAC  TCCTCAGTTC  CACAGTTTAT  CTGTTGCCCG            400
CTCCTAAATC  CACAGGCCCT  GCAGCAACCC  TCCTGAAGTA            440
GCAGAGTTAG  ACTGGAGTTC  CCCTCCCTGT  TCATCTTGCC            480
CTGGGGTCCC  TCTCCTCCTC  CCTTGCTGGC  TGTGTCCTAA            520
GCTGTGTGGG  ATTCAGGGTT  GGGGTGTAGT  TGGGAGGTGA            560
AATGAGGTGA  TTATATAATC  AACCACAGTC  CATCCCTCTT            600
TTTCAGGCAG  TATAAAGGCA  AACCACCCCA  GCCATCACCA            640
TCTATCATCC  CATGGCCACC  ATGCTGGCCT  CAGGGCTGCT            680
TCTGGTGACC  TTGCTGGCCT  GCCTGACTGT  GATGGTCTTG            720
ATGTCAGTCT  GGCGGCAGAG  GAAGAGCAGG  GGGAAGCTGC            760
CTCCGGGACC  CACCCCATTG  CCCTTCATTG  GAAACTACCT            800
CCAGCTGAAC  ACAGAGCAGA  TGTACAACTC  CCTCATGAAG            840
GTGTCCTAAG  GCAGGAGATG  GGTGGCACGG  GGTGGGGGCT            880
GCCCAGTTGG  CTGGGGCTTA  GTGGCAGGGG  ATTGACCAGT            920
GTGGACCAGA  GTCTTAGGAA  AGGGAGTCTT  GGAGTTTCAG            960
CATCAGGGTC  CTAGCAGGAA  AGACAGGATC  TTGGGATGTC           1000
CAGCTCCCTG  ACTGTGAGAA  CCTGGGGGGC  GAAGCATCCC           1040
AGTACATGAT  ATCTCAGCGC  TGGGCCCATT  CAGAGTGGGG           1080
GCTGCTCCCT  CTAACCACTC  CCACCTGCCT  CCAACAGATC           1120
AGTGAGCGCT  ATGGCCCTGT  GTTCACCATT  CACTTGGGGC           1160
CCCGGCGGGT  CGTGGTGCTG  TGCGGACATG  ATGCCGTCAA           1200
GGAGGCTCTG  GTGGACCAGG  CTGAGGAGTT  CAGCGGGCGA           1240
GGCGAGCAGG  CCACCTTCGA  CTGGCTCTTC  AAAGGCTATG           1280
GTGAGGGGGT  GCCAAGAGGG  GGAAGGTGGT  CAGGTGGATG           1320
CAATGGTCTC  CGTGTCCCCA  GCCTTCTCCC  TGACTCTCCT           1360
GCCCACTGGA  GGATATGGGA  GAGCCCCCTG  TCTGGTCTTC           1400
TCTCCCCATC  TCCCTACATC  GGGGACTCTC  CCTGTGAGTC           1440
CCACACCTGT  CTCCAGCGCC  CCTGGCGTGA  TTCCTCCCTG           1480
CCTCTCTCTG  CCCCGTCTCC  TCCTTCTCTC  TCACTGGAGT           1520
CTCCTCTTAC  CCCTCTCTCT  CCATCTCTGA  GGACATCCGG           1560
GGTTTCTGTT  TACCAGCCCT  GGTCCTCTGT  CTTCATTTGT           1600
CTTTTTGTCG  CTCTCGGCTT  CTGTGCTTCT  CCGTGTTTCT           1640
CCTCTCTCTG  CTTCCCTCTC  CCACTTCTTC  CTCTGTCTTA           1680
GGATTTCAGG  GTATTCCTAC  TTCCACATCT  CCAGCTCCCA           1720
```

| | | | | |
|---|---|---|---|---|
| ACTCCTGGTA | ATTGTCTGTC | CTCCTTCCCG | ATCCTCTCTG | 1760 |
| TTTCTGTCTC | CATATTTTTC | TCTCTCTTCT | CCAGTTCAGA | 1800 |
| TTAAGAATCT | TTCACCATTT | TTATTTCCTC | CTCCCAGATC | 1840 |
| TCCCCATATC | TCACTTCCCC | TCCCTCCATC | TCTCTCTTTC | 1880 |
| TCTCCCCACT | ACCTTCCCTT | CCTCCATGGA | GTATCCCCGT | 1920 |
| ATCCCTCTGT | TTCTCTGCAT | CTGTCTGTCT | GGCCTTTCTG | 1960 |
| CTTCTCTTCT | GATTCTCTTA | TTCTTTCTAC | CCGGACTCTC | 2000 |
| TCTCTCTCTC | TCTCTCTCTC | TCTCTCTCTC | TCTCTCTCTC | 2040 |
| TCTCTCTCTC | TCTCTCTCGT | GCTCTCGTGT | TTCTCTGACT | 2080 |
| GAGAGTGTAG | CTCTCCTGGG | CACTCGCGCT | GAATCCATCT | 2120 |
| CTCTCCCACA | CCACTCCCTC | TCTACACCAC | CCTGGGGAG | 2160 |
| CCCCTTGGAA | CTGGTCCGCT | CCTGCTACCA | CCACCCCCTG | 2200 |
| ACCTCTCTCC | ACCCCGCGT | TCACCTCCCC | AGGCGTGGCG | 2240 |
| TTCAGCAACG | GGGAGCGCGC | CAAGCAGCTC | CGGCGCTTCT | 2280 |
| CCATCGCCAC | CCTAAGGGGT | TTTGGCGTGG | GCAAGCGCGG | 2320 |
| CATCGAGGAA | CGCATCCAGG | AGGAGGCGGG | CTTCCTCATC | 2360 |
| GACGCCCTCC | GGGGCACGCA | CGGTGAGTAG | GGGACCCCGA | 2400 |
| GTGCGAGGGC | GGGAACCCGC | GCTTTCTGCC | TGGGGATGGG | 2440 |
| GACTAGGTGG | GGAAAGGGGC | CCGCACTTCC | AGCCCTGGAG | 2480 |
| TCTGGCGCTG | GGATTCGGCT | CAACAGGGCC | CTGCCTCCTG | 2520 |
| GAATTCTGAC | TCTCCTCAGA | CCTCTGAGTT | GACTCTCTCC | 2560 |
| CCAACCCCCC | TTCTCCCGCC | ACACCTGTAG | GCGCCAATAT | 2600 |
| CGATCCCACC | TTCTTCCTGA | GCCGCACAGT | CTCCAATGTC | 2640 |
| ATCAGCTCCA | TTGTCTTTGG | GGACCGCTTT | GACTATGAGG | 2680 |
| ACAAAGAGTT | CCTGTCACTG | TTGCGCATGA | TGCTGGGAAG | 2720 |
| GTTCCAGTTC | ACGGGAACCT | CCACGGGGCA | GGTAACTGGA | 2760 |
| TGCAGCCCGC | CAGTGACGCC | CCTACCACAA | CCTGCCAACT | 2800 |
| GCTCCCCTAC | CTGGAGACAG | GTGCCCCAAA | CTCCCACCCC | 2840 |
| CCTCCAGACA | GTGTCCCCTC | AAAATCAGTC | CCCGATATTG | 2880 |
| GACAACTGGA | CGGTTGGACC | AGAACCCAGG | AGGGATGCCC | 2920 |
| AATACCCAGT | CTCCAAGGAC | ACCTGGATAG | CTCAACAGAT | 2960 |
| GATCCCCAAA | ACAGAGCCTG | CTGGCAGGAT | GCATACCCTC | 3000 |
| AGCTCAGCTC | TCTCACCTGG | GCACATGTTC | CCATCCCCAT | 3040 |
| CTTACCGTAA | TTTGTAACAG | GTGCTCCCTA | CCCAGTTCTT | 3080 |
| CTGAATATTT | AACACCTGGA | CAAGTGACTG | TGTCAACCCG | 3120 |
| CCTCCTGCAT | ACCTGAACAC | CTGGTGCTGC | AAAATCCAGG | 3160 |
| CCATCATAAT | CATTTCACAT | CTACACAAAT | GTCACAGATT | 3200 |
| AGCCCACTGG | TAATATCTGG | CCAAGGGCCC | TCTACTTCAC | 3240 |
| CCACTTAAAT | GCCTGAAAAC | ATGGACAGGT | GCCCTAACCA | 3280 |
| ATACCCTAAA | CACATAAATA | TCTAGATAGA | TTATTCCCTG | 3320 |

| | | | | |
|---|---|---|---|---|
| ACACCCAAAT | AAGTGTTCCC | CAACCCTTTC | CAATCACACA | 3360 |
| CCTTACAGAG | GTGCTCCCAG | TGCATCCCAC | TTGGATAGGT | 3400 |
| AAACACCTCA | ACAGGTATCC | CCTCCACTTC | AGCATCTTCA | 3440 |
| CCAGCCCCAC | TTTATACCTG | AGCACCTGAA | CAAAAGCCCC | 3480 |
| CAATCCAGAC | CCAGTAAGTA | TCTGGACAGC | TGTCTCCAAC | 3520 |
| CAAGTCCACT | TGAATGCCTA | AATACCTAGA | CAGGTGCCAC | 3560 |
| TCACCTCATA | CCAGCCCCAC | CTGAAGAGCT | AAACACCTGG | 3600 |
| ACAGGTGTCT | TCCAACTCAA | CTTCACTTGA | ATATCTGAAC | 3640 |
| ACCTAGATGT | GTGCTCCAAT | CCAGCCTCAT | TTGCATACCT | 3680 |
| GAAACCTGGA | TATATGCCTC | AGTTCTTCTC | ACCTAAATTA | 3720 |
| CTAGACCGTG | CCCCTGGCAC | CTAATCCACG | TGAAAACTTA | 3760 |
| GATATAAGTT | TCCATCCAAC | CCCACTGAAA | TACCTAAACA | 3800 |
| CCTGGACAGA | TGCCTTTAAC | TCCGTTCCTT | CCTTGCTATG | 3840 |
| AAACAAATCC | CCATTCCCAT | CAGCTCCTGC | CCCGTGACAG | 3880 |
| CTGTCCTTCC | CTTCCCATCC | TCTCTCTGCA | ACCCCAGCTC | 3920 |
| TATGAGATGT | TCTCTTCGGT | GATGAAACAC | CTGCCAGGAC | 3960 |
| CACAGCAACA | GGCCTTTAAG | GAGCTGCAAG | GGCTGGAGGA | 4000 |
| CTTCATCGCC | AAGAAGGTGG | AGCACAACCA | GCGCACGCTG | 4040 |
| GATCCCAATT | CCCCACGGGA | CTTCATCGAC | TCCTTTCTCA | 4080 |
| TCCGCATGCA | GGAGGTACAT | CCCAGCAGCC | AGTGCAGGCA | 4120 |
| GGTGCAAAGC | CAGGGAGAGG | GAAATCAGGA | TGGGAGTGGG | 4160 |
| GTGGGCAGAC | GACACAGGCC | CATTCAAATT | AGCCCTCGTC | 4200 |
| ATAATAATCC | TTACAATTGG | CCAGGCGCGG | TGGCTCATGA | 4240 |
| CCTGTAATCC | CAGCACTTTG | GGAGGCCGAG | GCAGGTGGAT | 4280 |
| CACCTGAGGT | CAGGAGTTCG | AGACCAGCCT | GGCCAACATG | 4320 |
| GTGAAACCCC | GTCTCTACTA | AAAATACAAA | AATGAGCTAG | 4360 |
| GTATGGTGGC | ATGCGCCTGT | AATCCCAGCT | ACTCAGGAGG | 4400 |
| CTGAGACAGA | AGAATTTGTT | TGAATCCGGG | AGGCAGAGGT | 4440 |
| TGCAGTGAGC | CGGGATCATG | CCACTGCACT | CCGGCCTGAG | 4480 |
| TGACAGAGCA | AGACCCTGTA | AAAAAAAAAA | AAAAAAAAA | 4520 |
| AAAAAATTCC | GGAAAACCCC | AATTACATCA | CCCACTGCTG | 4560 |
| TCCATCTAC | TGAGCCCTCA | CCCACAAGGA | CGGGTTATGG | 4600 |
| AGGTGGATTA | GATTGGAAAG | AACTTCTCAA | GAACTACCGG | 4640 |
| GTGCCAGGAA | CTGGGTTAAG | TGTTTTATGA | TAGTCCGCCA | 4680 |
| TGGAACACTT | TTAACAGTTC | TTGAGGGAGG | TTCACTCATG | 4720 |
| GCCCCAGTTG | TACAAATGAG | GAAACTGAGG | CCCAGAGAGT | 4760 |
| TTAAGTGTCT | TAACTGAGGT | CACAACAGTG | AGGAAGACCA | 4800 |
| TGGTCCCCCT | AGCTCAAACC | CTGGTCTCTC | TGAGCCTATA | 4840 |
| GCTGGTGCTT | TTAGCCACCA | TGCTCTCTAA | CCGTTCATGT | 4880 |
| CCTGGTTAGC | AGACACACCT | CTGTGGACAG | GTGACCTGGC | 4920 |

```
TTTACATTGC AGGGTCCCCG CCTACCTCTG GATGTCAGCC            4960
TCCCATGTGG GAAGGCTTTA GGAAGCCAAA GCTCAGGGAG            5000
AAAGGATCAA GGGAGGGATT CCTCCACAGT AAGTTTCAAG            5040
ATTTTTAGGG AAGAAATAGG ATGCTGTTGC TTAAAATTCT            5080
GTGCTTGTAT CTCAGAAAAA CTCTTTTTTT CTGACTCTTC            5120
ATCTTGCCAT CTCTGTACTA CTTTCTCTTC GTCTCCCTC             5160
ATCCTTCTCT TTCCAAATAT TCCTATCATT AAAAAAGTAA            5200
CAGACTGGGA AACATGGCAA AACCCCGTCT GTACAAAAAA            5240
ATGGCTAGGC ATGGTGGTGC ATGCCTGCGG TCCAGCTAC             5280
TAAGGAGGTT GAGGTGGGAG GATATCTTGA GCCCAGGGTG            5320
GGCAGAGGTT TCAATGAGCC GATATCACAG CCCTGCCCTC            5360
CAGCCTGGGT GACAGAATAA GACCGTGTCT CCCAAAAAAA            5400
AAAGAATTA ATTTTTTAAC AGTTAACAAG TGAGCCTGCA             5440
TAGTCATGTG CATGTGCAGT TCCAGCTACT CTGGAGGCTG            5480
AGACCGGAGG ATTCCTTGAA CCCAGGAGTT GGAGTCCAGC            5520
CTGTGCAACT TAGCAAGACC AAGTCTGCAT AAAAAAAAA             5560
AAAACCAACT GACAGCTAAG TTGACAATTA AAGGATAGAT            5600
GATCAGTGAG GTAAAGAAGG TGAGAAGGAA GAGCATTTTG            5640
GGCAAAGCCA GCAGCCAGGG CAAGGGCTGG AACCTGGAGC            5680
GAGTTTGGCA AATCTAGGGT CCCTCTTTCC ACCTTTGGTC            5720
TGGACCAAAG AGAGGTAGCT CCAAAGGAAA AGCCCTAGAA            5760
GGGCCCCAAG AGCATGGAGA GTGAGCTTGG TCTAAACCGC            5800
CCTCTCCCTG CAGGAGGAGA AGAACCCCAA CACAGAGTTC            5840
TACTTGAAGA ACCTGGTGAT GACCACCCTG AACCTCTTCT            5880
TTGCGGGCAC TGAGACCGTG AGCACCACCC TGCGCTACGG            5920
TTTCCTGCTG CTCATGAAGC ACCCAGAGGT GGAGGGTAAG            5960
ACTGGAAAGG GAGGAAAGTG AAGGGCCCCA GACCCTCAAA            6000
ACTCCCCTGA GCCTGGTGCA GTGTACCCAC CTATCCCAGA            6040
TCCCAGGACC CTGAGACGTG CCTTGCTGTC CAGAGACAGG            6080
ACAATATTCA GCTGATAGGC ATCAGCTGAG TCTCATTAGC            6120
TATTAAAATA TTGAAAATGT CTGCACTGAT TGGTCAGTCA            6160
CTCCTGTCCC AAGCCCACTG AGTGTCCGCT GCCTGCTCCT            6200
CTGGATCATC CCCTAAGTTC CTCCCTTGTC CTACCCTGTG            6240
ATTCTGACAC AACCTGGTTT AACAGGGATC CTGCTGCAAA            6280
CAATGCGAAT GGGTGATGTC TTGTTCTTGT TTATGAATGG            6320
GCTTACCCTT CGTGTCAGAG GTGGAAGCTA TGTCAACCGC            6360
CGTGTTTTAG CTAGGGGGGG CGATACATGC CCTGCTCTAA            6400
GACCCCTAGA GAGGGTAAAG ATATTCCCCT CCTCCGCCAG            6440
CCAAGGTCCA TGAGGAGATT GACAGAGTGA TCGGCAAGAA            6480
CCGGCAGCCC AAGTTTGAGG ACCGGGCCAA GATGCCCTAC            6520
```

```
ACAGAGGCAG TGATCCACGA GATCCAAAGA TTTGGAGACA           6560
TGCTCCCCAT GGGTTTGGCC CACAGGGTCA ACAAGGACAC           6600
CAAGTTTCGG GATTTCTTCC TCCCTAAGGT GCTGTCTCCC           6640
CTCCACCACC ACCACTCAGA CTACGGGGAC TTCCAGCCTC           6680
TCTCTGTGTC CCCAGAATCC TGCCCCCATT AGTGTTCTAG           6720
ACTCTGTCCC ACTCCCTCAA TCAGTCAAAA AAGACTTCCC           6760
CAACCACCAC ATCTGTTCCA CCTTTCCACT TAGACAGTCC           6800
TGAGTCCTGC ATCTCGCCAG ACTCTTTGTG TCAGGAGAAT           6840
ACACCCCATG TTCCCAATCT TCCTGTCTTA AGAAACAGAA           6880
GCCCCCTTTC CATTAGGCCT TGTGGCTTAG GGACACAAAT           6920
CTCAGGTCCC TCAAACACCC TGGCTAGTGG AACATGGACC           6960
CCATGTCTCC CAAACTTCCT GTCTCAGAGA CATGAAACTT           7000
CTATCCCCCA AAGCTCCTCC CTCAGAGGTC CCCAACTCCT           7040
CCATGTCGTG CCACTCCCCG CACCTGGGGG ACCCTAGAGC           7080
CCCCTGGAGC CCCTGTGTAC TTTCACCAAT CCCCCAACC            7120
TGGCTCATAA CACACACCTT CCTCCTCCCT CCCAGGGCAC           7160
TGAAGTGTTC CCTATGCTGG GCTCCGAGCT GAGAGACCCC           7200
AGGTTCTTCT CCAACCCCCA GGACTGCAGT CCCCAGCACT           7240
TCCTGGATGA GAAGGGGCAG TTTAAGAAGA GTGATGCTTT           7280
TGTGCCCTTT TCCATCGGTA AGAGACACTG TTTGCTGCCA           7320
GGCCACGGCT CACACCAGCA GGGGCCTCTC TCACCCACCT           7360
CCCCTCTCTG CGGTGTAGCC TGGTATTTCT CCAGCTTGGA           7400
AGTTCCTGTT AGAATCTACC ATTGAGCCGC CACCAGCTGA           7440
TACTCCCTTA ACTGCCAAGC ACCCAATACC TGCGCCCAGG           7480
TAAAAGGGAA GGAAACATCT TCCCCCATAG ATTTATTTGT           7520
CTAGGGTCAC ACAGCAGATT CTTCAGCTCC CTGAAAAGGA           7560
GATAATGGTA CAGCACAGCA GTCATATTTG CAAGTGTATC           7600
TGGGGGGTAG GGGCATCTAA ACCTCCCATT GCTACACCTG           7640
GCATGGATCA CCCCATCTAT GATGGAGGCA TGACATTATG           7680
CCTTTTTCGA AACCCATAGA ACTGTATAAC ACAGAGTAAA           7720
CCCTAATGTA AACTATGGAC TTTGGTTAGT AATAATATAT           7760
CAATATTGGT TCACCATTGT TATATCTCTT ATAGAAGGAA           7800
ACTGAAGCTC AGGGAGGATC GGAGTCTCCT CTGAAAGTCT           7840
CTCAGGCCAT AATATTCCCA CCCCTCCTCC CTAGAGAGTG           7880
CAGCCGGGGG TCAGTAGGGG TTGAGGCTGC ACTGAGAGTG           7920
GGCTTCACCT TCACCCCTCC TGCCTCTCCT CCTCAGGAAA           7960
GCGGTACTGT TTTGGAGAAG GCCTGGCCAG AATGGAGCTC           8000
TTTCTCTTCT TCACCACCAT CATGCAGAAC TTTCGCTTCA           8040
AGTCCCCTCA GTCGCCTAAG GATATCGACG TGTCCCCCAA           8080
ACACGTGGGC TTTGCCACGA TCCCACGAAA CTACACCATG           8120
```

| | | | | |
|---|---|---|---|---|
| AGCTTCCTGC | CCCGCTGAGC | GAGGGCTGTG | CTGGTGCAGG | 8160 |
| GCTGGTGGGC | GGGGCCAGGG | AAACGGCCGG | GGCAGGGGCG | 8200 |
| GGGCTTGTGG | GAGGGGCGGG | GCTAAGAATG | GGGGCAGTGG | 8240 |
| GGGAAGGAAG | GGGAGAGGTG | GTTAGAGGGA | ACAGAAGAAA | 8280 |
| CAGAAGGGGC | TCAGTTCACC | TTGATGATGT | CCTTCAGAGC | 8320 |
| TGTGATGAGA | GGAAGGGAAA | CCTTACAGTA | TGCTACAAAG | 8360 |
| AGTAGTAATA | ATAGCAGCTC | TTATCTCCTG | AACAAGTCCC | 8400 |
| TCCCTGTCAG | CTTTGTTCAA | AAAGCGTTGC | ACGCTCACCT | 8440 |
| CACTTATTTG | CCACACACCT | CTACCAATGG | GGGAAAAGTC | 8480 |
| TTCATTCCCC | TTTTTACACG | TGAGAAAGGT | GCGGCTCAGA | 8520 |
| AAGTTGTCTC | TATCTGAAAA | CTCACAAAAC | GCAAGTGTCC | 8560 |
| AGAGGATCTT | GGAACACAGA | TCTGGGCCCA | TAGCCCTCTA | 8600 |
| GATCGATCCT | CACCATAGCA | CCCCTTCTTC | ACGTAAAATA | 8640 |
| GCTTAGTATA | GCATCACATG | GCCTGAACAC | CCCTGGGCCG | 8680 |
| GGGGGTTCCC | CAGAGACCTG | GCGGGCGGCT | GCCCTGCCTA | 8720 |
| CTCTGTACAC | TCGCCTACTC | GGGACGATCC | GGGCACCAGG | 8760 |
| GTGTCACCTG | AGCTCGCTA | | | 8779 |

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: linear ( i i ) MOLECULE TYPE: oligonucleotide ( i x ) FEATURE:
        ( A ) NAME/KEY: HF18
        ( B ) LOCATION:
        ( D ) OTHER INFORMATION: Primer used for CYP2C9
            mutation detection.

( x i ) SEQUENCE DESCRIPTION: SEQ ID NO:5:

| | |
|---|---|
| TGCAAGTGCC TGTTTCAGCA | 20 |

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: linear ( i i ) MOLECULE TYPE: oligonucleotide ( i x ) FEATURE:
        ( A ) NAME/KEY: HF2R
        ( B ) LOCATION:
        ( D ) OTHER INFORMATION: Primer used for CYP2C9
            mutation detection.

( x i ) SEQUENCE DESCRIPTION: SEQ ID NO:6:

| | |
|---|---|
| AGCCTTGGTT TTTCTCAACT C | 21 |

( 2 ) INFORMATION FOR SEQ ID NO:7:

( i ) SEQUENCE CHARACTERISTICS:
  ( A ) LENGTH: 20 base pairs
  ( B ) TYPE: nucleic acid
  ( C ) STRANDEDNESS: unknown
  ( D ) TOPOLOGY: linear ( i i ) MOLECULE TYPE: oligonucleotide ( i x ) FEATURE:
  ( A ) NAME/KEY: J51
  ( B ) LOCATION:
  ( D ) OTHER INFORMATION: Primer used for CYP2A6
      detection.

( x i ) SEQUENCE DESCRIPTION: SEQ ID NO:7:

GGCTTCCTCA TCGACGCACT                                                    20

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: linear ( i i ) MOLECULE TYPE: oligonucleotide ( i x ) FEATURE:
    ( A ) NAME/KEY: J61
    ( B ) LOCATION:
    ( D ) OTHER INFORMATION: Primer used for CYP2A6
        detection.

( x i ) SEQUENCE DESCRIPTION: SEQ ID NO:8:

GGCTTCCTCA TCGACGCACA                                                    20

( 2 ) INFORMATION FOR SEQ ID NO:9:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: linear ( i i ) MOLECULE TYPE: oligonucleotide ( i x ) FEATURE:
    ( A ) NAME/KEY: Primer B
    ( B ) LOCATION:
    ( D ) OTHER INFORMATION: Primer used for CYP2A6
        detection.

( x i ) SEQUENCE DESCRIPTION: SEQ ID NO:9:

AATTCCAGGA GGCAGGGCCT                                                    20

( 2 ) INFORMATION FOR SEQ ID NO:10:

( i ) SEQUENCE CHARACTERISTICS:
    ( A ) LENGTH: 57 base pairs
    ( B ) TYPE: nucleic acid
    ( C ) STRANDEDNESS: unknown
    ( D ) TOPOLOGY: linear ( i i ) MOLECULE TYPE: oligonucleotide ( i x ) FEATURE:
    ( A ) NAME/KEY: F4 primer
    ( B ) LOCATION:
    ( D ) OTHER INFORMATION: Primer used for CYP2A6
        genotyping.

( x i ) SEQUENCE DESCRIPTION: SEQ ID NO:10:

CCCCTTATCC TCCCTTGCTG GCTGTGTCCC AAGCTAGGCA                               40

GGATTCATGG TGGGGCA                                                                                        57

( 2 ) INFORMATION FOR SEQ ID NO:11:

( i ) SEQUENCE CHARACTERISTICS:
          ( A ) LENGTH: 31 base pairs
          ( B ) TYPE: nucleic acid
          ( C ) STRANDEDNESS: unknown
          ( D ) TOPOLOGY: linear ( i i ) MOLECULE TYPE: oligonucleotide ( i x ) FEATURE:
          ( A ) NAME/KEY: fragment of F4
          ( B ) LOCATION:
          ( D ) OTHER INFORMATION: Primer used for CYP2A6
               genotyping.

( x i ) SEQUENCE DESCRIPTION: SEQ ID NO:11:

CCTCCCTTGC TGGCTGTGTC CCAAGCTAGG C                                                                        31

( 2 ) INFORMATION FOR SEQ ID NO:12:

( i ) SEQUENCE CHARACTERISTICS:
          ( A ) LENGTH: 57 base pairs
          ( B ) TYPE: nucleic acid
          ( C ) STRANDEDNESS: unknown
          ( D ) TOPOLOGY: linear ( i i ) MOLECULE TYPE: oligonucleotide ( i x ) FEATURE:
          ( A ) NAME/KEY: R4
          ( B ) LOCATION:
          ( D ) OTHER INFORMATION: Primer used for CYP2A6
               genotyping.

( x i ) SEQUENCE DESCRIPTION: SEQ ID NO:12:

GCCACCACGC CCCTTCCTTT CCGCCATCCT GCCCCAGTC                                                                 40

TTAGCTGCGC CCCTCTC                                                                                        57

( 2 ) INFORMATION FOR SEQ ID NO:13:

( i ) SEQUENCE CHARACTERISTICS:
          ( A ) LENGTH: 31 base pairs
          ( B ) TYPE: nucleic acid
          ( C ) STRANDEDNESS: unknown
          ( D ) TOPOLOGY: linear ( i i ) MOLECULE TYPE: oligonucleotide ( i x ) FEATURE:
          ( A ) NAME/KEY: fragment of R4
          ( B ) LOCATION:
          ( D ) OTHER INFORMATION: Primer used for CYP2A6
               genotyping.

( x i ) SEQUENCE DESCRIPTION: SEQ ID NO:13:

CGCCCCTTCC TTTCCGCCAT CCTGCCCCCA G                                                                        31

( 2 ) INFORMATION FOR SEQ ID NO:14:

( i ) SEQUENCE CHARACTERISTICS:
          ( A ) LENGTH: 54 base pairs
          ( B ) TYPE: nucleic acid
          ( C ) STRANDEDNESS: unknown
          ( D ) TOPOLOGY: linear ( i i ) MOLECULE TYPE: oligonucleotide ( i x ) FEATURE:

(A) NAME/KEY: E3F
(B) LOCATION:
(D) OTHER INFORMATION: Primer used to distinguish CYP2A6v1 from CYP2A6v2.

(xi) SEQUENCE DESCRIPTION: SEQ ID NO:14:

CCTGATCGAC TAGGCGTGGT ATTCAGCAAC GGGGAGCGCG 40

CCAAGCAGCT CCTG 54

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: unknown
(D) TOPOLOGY: linear (ii) MOLECULE TYPE: oligonucleotide (ix) FEATURE:
(A) NAME/KEY: fragment of E3F
(B) LOCATION:
(D) OTHER INFORMATION: Primer used to distinguish CYP2A6v1 from CYP2A6v2.

(xi) SEQUENCE DESCRIPTION: SEQ ID NO:15:

GCGTGGTATT CAGCAACGGG 20

(2) INFORMATION FOR SEQ ID NO:16:

(i) SEQUENCE CHARACTERISTICS:
(A) LENGTH: 57 base pairs
(B) TYPE: nucleic acid
(C) STRANDEDNESS: unknown
(D) TOPOLOGY: linear (ii) MOLECULE TYPE: oligonucleotide (ix) FEATURE:
(A) NAME/KEY: E3R
(B) LOCATION:
(D) OTHER INFORMATION: Primer used to distinguish CYP2A6v1 from CYP2A6v2.

(xi) SEQUENCE DESCRIPTION: SEQ ID NO:16:

CGCGCGGGTT CCTCGTCCTG GGTGTTTTCC TTCTCCTGCC 40

CCCGCACTCG GGATGCG 57

(2) INFORMATION FOR SEQ ID NO:17:

(i) SEQUENCE CHARACTERISTICS:
(A) LENGTH: 21 base pairs
(B) TYPE: nucleic acid
(C) STRANDEDNESS: unknown
(D) TOPOLOGY: linear (ii) MOLECULE TYPE: oligonucleotide (ix) FEATURE:
(A) NAME/KEY: fragment of E3R
(B) LOCATION:
(D) OTHER INFORMATION: Primer used to distinguish CYP2A6v1 from CYP2A6v2.

(xi) SEQUENCE DESCRIPTION: SEQ ID NO:17:

TCGTCCTGGG TGTTTTCCTT C 21